(12) United States Patent
Thomas et al.

(10) Patent No.: US 12,161,639 B2
(45) Date of Patent: Dec. 10, 2024

(54) METHODS OF TREATING PACS1 AND PACS2 SYNDROMES

(71) Applicant: University of Pittsburgh—Of the Commonwealth System of Higher Education, Pittsburgh, PA (US)

(72) Inventors: Gary Thomas, Pittsburgh, PA (US); Laurel Thomas, Pittsburgh, PA (US); Sabrina Villar-Pazos, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 985 days.

(21) Appl. No.: 17/260,713

(22) PCT Filed: Jul. 17, 2019

(86) PCT No.: PCT/US2019/042172
§ 371 (c)(1),
(2) Date: Jan. 15, 2021

(87) PCT Pub. No.: WO2020/018647
PCT Pub. Date: Jan. 23, 2020

(65) Prior Publication Data
US 2021/0290612 A1    Sep. 23, 2021

Related U.S. Application Data

(60) Provisional application No. 62/699,330, filed on Jul. 17, 2018.

(51) Int. Cl.
| | | |
|---|---|---|
| *A61K 31/473* | (2006.01) | |
| *A61K 31/421* | (2006.01) | |
| *A61K 45/06* | (2006.01) | |
| *C12N 15/113* | (2010.01) | |

(52) U.S. Cl.
CPC .......... *A61K 31/473* (2013.01); *A61K 31/421* (2013.01); *A61K 45/06* (2013.01); *C12N 15/113* (2013.01); *C12N 2310/11* (2013.01); *C12N 2310/14* (2013.01)

(58) Field of Classification Search
CPC .... A61K 31/473; A61K 31/421; A61K 45/06; A61K 31/167; A61K 31/27; A61K 31/422; A61K 31/437; A61K 31/47; A61K 31/4709; A61K 31/505; A61K 31/506; C12N 15/113; C12N 2310/11; C12N 2310/14; A61P 25/28; A61P 25/00
USPC ...................................................... 514/279
See application file for complete search history.

(56) References Cited

U.S. PATENT DOCUMENTS

| | | | |
|---|---|---|---|
| 8,101,348 B2 | 1/2012 | Tuschl et al. | |
| 8,901,156 B2 | 12/2014 | Baloglu et al. | |
| 9,572,789 B2 | 2/2017 | Lin et al. | |
| 9,884,850 B2 | 2/2018 | Mazitschek et al. | |
| 2004/0142859 A1 | 7/2004 | Steffan et al. | |
| 2006/0052280 A1 | 3/2006 | Von der Kammer et al. | |
| 2007/0078083 A1 | 4/2007 | Barlow et al. | |
| 2007/0207950 A1 | 9/2007 | Yao et al. | |
| 2008/0021063 A1 | 1/2008 | Kazantsev | |
| 2009/0325862 A1 | 12/2009 | Steinkuhler et al. | |
| 2013/0227717 A1 | 8/2013 | Van Den Bosch et al. | |
| 2017/0044185 A1 | 2/2017 | Ma et al. | |
| 2017/0081667 A1 | 3/2017 | Chen et al. | |

FOREIGN PATENT DOCUMENTS

WO    2018068357 A1    4/2019

OTHER PUBLICATIONS

Aslan et al., "Akt and 14-3-3 control a PACS-2 homeostatic switch that integrates membrane traffic with TRAIL-Induced apoptosis," 2009, Mol Cell., vol. 34, pp. 497-509.
Atkins et al., "HIV-1 Nef binds PACS-2 to assemble a multikinase cascade that triggers major histocompatibility complex class I (MHC-I) down-regulation: analysis using short interfering RNA and knock-out mice," 2008, J Biol Chem., vol. 283, Issue 17, pp. 11772-11784.
Corey, "Chemical modification: the key to clinical application of RNA interference?" 2007, J Clin Invest., vol. 117, Issue 12, pp. 3615-3622.
Deakin et al., "Paxillin inhibits HDAC6 to regulate microtubule acetylation, Golgi structure, and polarized migration," 2014, J Cell Biol., vol. 206, Issue 3, pp. 395-413.
De Oliviera et al., "The mechanism of sirtuin 2-mediated exacerbation of alpha-synuclien toxicity in models of Parkinson disease," 2017, PLoS Biol., vol. 15, Issue 3, p. e20000374.
Fukuda et al., "Rescue of CAMDI deletion-induced delayed radial migration and psychiatric behaviors by HDAC6 inhibitor," 2016, EMBO Rep., vol. 17, Issue 12, pp. 1785-1798.
Gao et al., "The Microtubule-associated Histone Deacetylase 6 (HDAC6) Regulates Epidermal Growth Factor Receptor (EGFR) Endocytic Trafficking and Degradation," 2010, J Biol Chem., vol. 285, Issue 15, pp. 11219-11226.
Jenkins et al., "PACS-1 mediates phosphorylation-depending ciliary trafficking of the cyclic-nucleotide-gated channel in olfactory sensory neurons," 2009, J Neurosci., vol. 29, Issue 34, pp. 10541-10551.
Kaufmann et al., "Dendritic anomalies in disorders associated with mental retardation," 2000, Cereb. Cortex, vol. 10, pp. 981-991.
Krzysiak et al., "An Insulin-Responsive Sensor in the SIRT1 Disordered Region Binds DBC1 and PACS-2 to Control Enzyme Activity," 2018, Mol Cell., vol. 72, pp. 985-998.
Lima et al., "Single-stranded siRNAs activate RNAi in animals," 2012, Cell, vol. 150, pp. 883-894.
Olson et al., "A Recurrent De Novo PACS2 Heterozygous Missense Variant Causes Neonatal-Onset Developmental Epileptic Encephalopathy, Facial Dysmorphism, and Cerebellar Dysgenesis," 2018, Am J Hum Genet., vol. 102, Issue 5, pp. 995-1007.

(Continued)

*Primary Examiner* — Yevgeny Valenrod
(74) *Attorney, Agent, or Firm* — The Webb Law Firm

(57) ABSTRACT

Methods are provided for treatment of PACS1 syndrome and PACS2 syndrome.

25 Claims, 19 Drawing Sheets

Specification includes a Sequence Listing.

(56) References Cited

OTHER PUBLICATIONS

Schermer et al., "Phosphorylation by casein kinase 2 induces PACS-1 binding of nephrocystin and targeting to cilia," 2005, EMBO J., vol. 24, pp. 4415-4424.

Silva et al., "Mitochondrial Metabolism Power SIRT2-Dependent Deficient Traffic Causing Alzheimer's-Disease Related Pathology," 2017, Mol Neurobiol., vol. 54, pp. 4021-4040.

Simmen et al., "PACS-2 controls endoplasmic reticulum-mitochondria communication and Bid-mediated apoptosis," 2005, EMBO J., vol. 24, pp. 717-729.

Thomas et al., "Caught in the act—protein adaptation and the expanding roles of the PACS proteins in tissue homeostasis and disease," 2017, J Cell Sci., vol. 130, pp. 1865-1876.

Valente et al., "Primary cilia in neurodevelopmental disorders," 2014, Nat Rev Neurol., vol. 10, Issue 1, pp. 27-36.

Vogl et al., "Ricolinostat, the First Selective Histone Deacetylase 6 Inhibitor, in Combination with Bortezomib and Dexamethasone for Relapsed or Refractory Multiple Myeloma," 2017, Clin Cancer Res., vol. 23, Issue 13, pp. 3307-3315.

Wan et al., "PACS-1 defines a novel gene family of cytosolic sorting proteins required for trans-Golgi network localization," 1998, Cell, vol. 94, pp. 205-216.

Wang et al., "Recent advances in the discovery of potent and selective HDAC6 inhibitors," 2018, Eur J Med Chem., vol. 143, pp. 1406-1418.

Watts et al., "Silencing disease genes in the laboratory and the clinic," 2012, J Pathol., vol. 226, Issue 2, pp. 365-379.

Wu et al., "Improved siRNA/shRNA Functionality by Mismatched Duplex," PLoS One, 2011, vol. 6, Issue 12, p. e28580.

Yadav et al., "Golgi Positioning," 2011, Cold Spring Harb Perspect Biol., vol. 3, Issue 5, p. a005322.

Yoo et al., "Sodium butyrate, a histone deacetylase inhibitor, ameliorates SIRT2-induced memory impairment, reduction of cell proliferation, and neuroblast differentiation in the dentate gyrus," 2014, Neurol Res., vol. 37 Issue 1, pp. 69-76.

>NP_001308154.1 histone deacetylase 6 isoform a [Homo sapiens]
MSGANRGRGQASSTMTSTGQDSTTTRQRRSRQNPQSPPQDSSVTSKRNIKKGAVPRSIPNLAEVKKKGKM
KKLGQAMEEDLIVGLQGMDLNLEAEALAGTGLVLDEQLNEFHCLWDDSFPEGPERLHAIKEQLIQEGLLD
RCVSFQARFAEKEELMLVHSLEYIDLMETTQYMNEGELRVLADTYDSVYLHPNSYSCACLASGSVLRLVD
AVLGAEIRNGMAIIRPPGHHAQHSLMDGYCMFNHVAVAARYAQQKHRIRRVLIVDWDVHHGQGTQFTFDQ
DPSVLYFSIHRYEQGRFWPHLKASNWSTTGFGQGQGYTINVPWNQVGMRDADYIAAFLHVLLPVALEFQP
QLVLVAAGFDALQGDPKGEMAATPAGFAQLTHLLMGLAGGKLILSLEGGYNLRALAEGVSASLHTLLGDP
CPMLESPGAPCRSAQASVSCALEALEPFWEVLVRSTETVERDNMEEDNVEESEEEGPWEPPVLPILTWPV
LQSRTGLVYDQNMMNHCNLWDSHHPEVPQRILRIMCRLEELGLAGRCLTLTPRPATEAELLTCHSAEYVG
HLRATEKMKTRELHRESSNFDSIYICPSTFACAQLATGAACRLVEAVLSGEVLNGAAVVRPPGHHAEQDA
ACGFCFFNSVAVAARHAQTISGHALRILIVDWDVHHGNGTQHMFEDDPSVLYVSLHRYDHGTFFPMGDEG
ASSQIGRAAGTGFTVNVAWNGPRMGDADYLAAWHRLVLPIAYEFNPELVLVSAGFDAARGDPLGGCQVSP
EGYAHLTHLLMGLASGRIILILEGGYNLTSISESMAACTRSLLGDPPPLLTLPRPPLSGALASITETIQV
HRRYWRSLRVMKVEDREGPSSSKLVTKKAPQPAKPRLAERMTTREKKVLEAGMGKVTSASFGEESTPGQT
NSETAVVALTQDQPSEAATGGATLAQTISEAAIGGAMLGQTTSEEAVGGATPDQTTSEETVGGAILDQTT
SEDAVGGATLGQTTSEEAVGGATLAQTTSEAAMEGATLDQTTSEEAPGGTELIQTPLASSTDHQTPPTSP
VQGTTPQISPSTLIGSLRTLELGSESQGASESQAPGEENLLGEAAGGQDMADSMLMQGSRGLTDQAIFYA
VTPLPWCPHLVAVCPIPAAGLDVTQPCGDCGTIQENWVCLSCYQVYCGRYINGHMLQHHGNSGHPLVLSY
IDLSAWCYYCQAYVHHQALLDVKNIAHQNKFGEDMPHPH >NM_001321225.2 Homo sapiens histone deacetylase 6 (HDAC6), transcript
variant 1, mRNA
CACGGCGCGTCGCGCGGGAAGTCGCGGGGAAAAGGTCGCCAGAAACTTGGTGGAGCGAGCCAAGGGCGGA
GTTTGAGAAAGGGGCTGCGTCCAATGAGTGGAGCGAACCGCGGCAGGGGCCAAGCCTCCTCAACTATGAC
CTCAACCGGCCAGGATTCCACCACAACCAGGCAGCGAAGAAGTAGGCAGAACCCCCAGTCGCCCCCTCAG
GACTCCAGTGTCACTTCGAAGCGAAATATTAAAAAGGGAGCCGTTCCCGCTCTATCCCCAATCTAGCGG
AGGTAAAGAAGAAAGGCAAAATGAAGAAGCTCGGCCAAGCAATGGAAGAAGACCTAATCGTGGGACTGCA
AGGGATGGATCTGAACCTTGAGGCTGAAGCACTGGCTGGCACTGGCTTGGTGTTGGATGAGCAGTTAAAT
GAATTCCATTGCCTCTGGGATGACAGCTTCCCGGAAGGCCCTGAGCGGCTCCATGCCATCAAGGAGCAAC
TGATCCAGGAGGGCCTCCTAGATCGCTGCGTGTCCTTTCAGGCCCGGTTTGCTGAAAAGGAAGAGCTGAT
GTTGGTTCACAGCCTAGAATATATTGATCTGATGGAAACAACCCAGTACATGAATGAGGGAGAACTCCGT
GTCCTAGCAGACACCTACGACTCAGTTTATCTGCATCCGAACTCATACTCCTGTGCCTGCCTGGCCTCAG
GCTCTGTCCTCAGGCTGGTGGATGCGGTCCTGGGGGCTGAGATCCGGAATGGCATGGCCATCATTAGGCC
TCCTGGACATCACGCCCAGCACAGTCTTATGGATGGCTATTGCATGTTCAACCACGTGGCTGTGGCAGCC
CGCTATGCTCAACAGAAACACCGCATCCGGAGGGTCCTTATCGTAGATTGGGATGTGCACCACGGTCAAG
GAACACAGTTCACCTTCGACCAGGACCCCAGTGTCCTCTATTTCTCCATCCACCGCTACGAGCAGGGTAG
GTTCTGGCCCCACCTGAAGGCCTCTAACTGGTCCACCACAGGTTTCGGCCAAGGCCAAGGATATACCATC
AATGTGCCTTGGAACCAGGTGGGGATGCGGGATGCTGACTACATTGCTGCTTTCCTGCACGTCCTGCTGC
CAGTCGCCCTCGAGTTCCAGCCTCAGCTGGTCCTGGTGGCTGCTGGATTTGATGCCCTGCAAGGGGACCC
CAAGGGTGAGATGGCCGCCACTCCGGCAGGGTTCGCCCAGCTAACCCACCTGCTCATGGGTCTGGCAGGA
GGCAAGCTGATCCTGTCTCTGGAGGGTGGCTACAACCTCCGCGCCCTGGCTGAAGGCGTCAGTGCTTCGC
TCCACACCCTTCTGGGAGACCCTTGCCCCATGCTGGAGTCACCTGGTGCCCCTGCCGGAGTGCCCAGGC
TTCAGTTTCCTGTGCTCTGGAAGCCCTTGAGCCCTTCTGGGAGGTTCTTGTGAGATCAACTGAGACCGTG
GAGAGGGACAACATGGAGGAGGACAATGTAGAGGAGAGCGAGGAGGAAGGACCCTGGGAGCCCCTGTGC
TCCCAATCCTGACATGGCCAGTGCTACAGTCTCGCACAGGGCTGGTCTATGACCAAAATATGATGAATCA
CTGCAACTTGTGGACAGCCACCACCCTGAGGTACCCCAGCGCATCTTGCGGATCATGTGCCGTCTGGAG
GAGCTGGGCCTTGCCGGGCGCTGCCTCACCCTGACACCGCGCCCTGCCACAGAGGCTGAGCTGCTCACCT
GTCACAGTGCTGAGTACGTGGGTCATCTCCGGGCCACAGAGAAAATGAAAACCCGGGAGCTGCACCGTGA
GAGTTCCAACTTTGACTCCATCTATATCTGCCCCAGTACCTTCGCCTGTGCACAGCTTGCCACTGGCGCT
GCCTGCCGCCTGGTGGAGGCTGTGCTCTCAGGAGAGGTTCTGAATGGTGCTGCTGTGGTGCGTCCCCCAG
GACACCACGCAGAGCAGGATGCAGCTTGCGGTTTTTGCTTTTTCAACTCTGTGGCTGTGGCTGCTCGCCA
TGCCCAGACTATCAGTGGGCATGCCCTACGGATCCTGATTGTGGATTGGGATGTCCACCACGGTAATGGA
ACTCAGCACATGTTTGAGGATGACCCCAGTGTGCTATATGTGTCCCTGCACCGCTATGATCATGGCACCT

FIG. 16A

```
TCTTCCCCATGGGGGATGAGGGTGCCAGCAGCCAGATCGGCCGGGCTGCGGGCACAGGCTTCACCGTCAA
CGTGGCATGGAACGGGCCCCGCATGGGTGATGCTGACTACCTAGCTGCCTGGCATCGCCTGGTGCTTCCC
ATTGCCTACGAGTTTAACCCAGAACTGGTGCTGGTCTCAGCTGGCTTTGATGCTGCACGGGGGGATCCGC
TGGGGGGCTGCCAGGTGTCACCTGAGGGTTATGCCCACCTCACCCACCTGCTGATGGGCCTTGCCAGTGG
CCGCATTATCCTTATCCTAGAGGGTGGCTATAACCTGACATCCATCTCAGAGTCCATGGCTGCCTGCACT
CGCTCCCTCCTTGGAGACCCACCACCCCTGCTGACCCTGCCACGGCCCCCACTATCAGGGGCCCTGGCCT
CAATCACTGAGACCATCCAAGTCCATCGCAGATACTGGCGCAGCTTACGGGTCATGAAGGTAGAAGACAG
AGAAGGACCCTCCAGTTCTAAGTTGGTCACCAAGAAGGCACCCCAACCAGCCAAACCTAGGTTAGCTGAG
CGGATGACCACACGAGAAAAGAAGGTTCTGGAAGCAGGCATGGGGAAAGTCACCTCGGCATCATTTGGGG
AAGAGTCCACTCCAGGCCAGACTAACTCAGAGACAGCTGTGGTGGCCCTCACTCAGGACCAGCCCTCAGA
GGCAGCCACAGGGGGAGCCACTCTGGCCCAGACCATTTCTGAGGCAGCCATTGGGGGAGCCATGCTGGGC
CAGACCACCTCAGAGGAGGCTGTCGGGGGAGCCACTCCGGACCAGACCACCTCAGAGGAGACTGTGGGAG
GAGCCATTCTGGACCAGACCACCTCAGAGGATGCTGTTGGGGGAGCCACGCTGGGCCAGACTACCTCAGA
GGAGGCTGTAGGAGGAGCTACACTGGCCCAGACCACCTCGGAGGCAGCCATGGAGGGAGCCACACTGGAC
CAGACTACGTCAGAGGAGGCTCCAGGGGGCACCGAGCTGATCCAAACTCCTCTAGCCTCGAGCACAGACC
ACCAGACCCCCCCAACCTCACCTGTGCAGGGAACTACACCCCAGATATCTCCCAGTACACTGATTGGGAG
TCTCAGGACCTTGGAGCTAGGCAGCGAATCTCAGGGGGCCTCAGAATCTCAGGCCCCAGGAGAGGAGAAC
CTACTAGGAGAGGCAGCTGGAGGTCAGGACATGGCTGATTCGATGCTGATGCAGGGATCTAGGGGCCTCA
CTGATCAGGCCATATTTTATGCTGTGACACCACTGCCCTGGTGTCCCCATTTGGTGGCAGTATGCCCCAT
ACCTGCAGCAGGCCTAGACGTGACCCAACCTTGTGGGACTGTGGAACAATCCAAGAGAATTGGGTGTGT
CTCTCTTGCTATCAGGTCTACTGTGGTCGTTACATCAATGGCCACATGCTCCAACACCATGGAAATTCTG
GACACCCGCTGGTCCTCAGCTACATCGACCTGTCAGCCTGGTGTTACTACTGTCAGGCCTATGTCCACCA
CCAGGCTCTCCTAGATGTGAAGAACATCGCCCACCAGAACAAGTTTGGGGAGGATATGCCCCACCCACAC
TAAGCCCCAGAATACGGTCCCTCTTCACCTTCTGAGGCCCACGATAGACCAGCTGTAGCTCATTCCAGCC
TGTACCTTGGATGAGGGGTAGCCTCCCACTGCATCCCATCCTGAATATCCTTTGCAACTCCCCAAGAGTG
CTTATTTAAGTGTTAATACTTTTAAGAGAACTGCGACGATTAATTGTGGATCTCCCCCTGCCCATTGCCT
GCTTGAGGGGCACCACTACTCCAGCCCAGAAGGAAAGGGGGCAGCTCAGTGGCCCCAAGAGGGAGCTGA
TATCATGAGGATAACATTGGCGGGAGGGGAGTTAACTGGCAGGCATGGCAAGGTTGCATATGTAATAAAG
TACAAGCTGTTAAAAAA
```

FIG. 16B

>NP_036369.2 NAD-dependent protein deacetylase sirtuin-2 isoform 1 [Homo sapiens]
MAEPDPSHPLETQAGKVQEAQDSDSDSEGGAAGGEADMDFLRNLFSQTLSLGSQKERLLDELTLEGVARY
MQSERCRRVICLVGAGISTSAGIPDFRSPSTGLYDNLEKYHLPYPEAIFEISYFKKHPEPFFALAKELYP
GQFKPTICHYFMRLLKDKGLLLRCYTQNIDTLERIAGLEQEDLVEAHGTFYTSHCVSASCRHEYPLSWMK
EKIFSEVTPKCEDCQSLVKPDIVFFGESLPARFFSCMQSDFLKVDLLLVMGTSLQVQPFASLISKAPLST
PRLLINKEKAGQSDPFLGMIMGLGGGMDFDSKKAYRDVAWLGECDQGCLALAELLGWKKELEDLVRREHA
SIDAQSGAGVPNPSTSASPKKSPPPAKDEARTTEREKPQ >NM_012237.4 Homo sapiens sirtuin 2 (SIRT2), transcript variant 1, mRNA
AGTCGGTGACAGGACAGAGCAGTCGGTGACGGGACACAGTGGTTGGTGACGGGACAGAGCGGTCGGTGAC
AGCCTCAAGGGCTTCAGCACCGCGCCCATGGCAGAGCCAGACCCCTCTCACCCTCTGGAGACCCAGGCAG
GGAAGGTGCAGGAGGCTCAGGACTCAGATTCAGACTCTGAGGGAGGAGCCGCTGGTGGAGAAGCAGACAT
GGACTTCCTGCGGAACTTATTCTCCCAGACGCTCAGCCTGGGCAGCCAGAAGGAGCGTCTGCTGGACGAG
CTGACCTTGGAAGGGGTGGCCCGGTACATGCAGAGCGAACGCTGTCGCAGAGTCATCTGTTTGGTGGGAG
CTGGAATCTCCACATCCGCAGGCATCCCCGACTTTCGCTCTCCATCCACCGGCCTCTATGACAACCTAGA
GAAGTACCATCTTCCCTACCCAGAGGCCATCTTTGAGATCAGCTATTTCAAGAAACATCCGGAACCCTTC
TTCGCCCTCGCCAAGGAACTCTATCCTGGGCAGTTCAAGCCAACCATCTGTCACTACTTCATGCGCCTGC
TGAAGGACAAGGGGCTACTCCTGCGCTGCTACACGCAGAACATAGATACCCTGGAGCGAATAGCCGGGCT
GGAACAGGAGGACTTGGTGGAGGCGCACGGCACCTTCTACACATCACACTGCGTCAGCGCCAGCTGCCGG
CACGAATACCCGCTAAGCTGGATGAAAGAGAAGATCTTCTCTGAGGTGACGCCCAAGTGTGAAGACTGTC
AGAGCCTGGTGAAGCCTGATATCGTCTTTTTTGGTGAGAGCCTCCCAGCGCGTTTCTTCTCCTGTATGCA
GTCAGACTTCCTGAAGGTGGACCTCCTCCTGGTCATGGGTACCTCCTTGCAGGTGCAGCCCTTTGCCTCC
CTCATCAGCAAGGCACCCCTCTCCACCCCTCGCCTGCTCATCAACAAGGAGAAAGCTGGCCAGTCGGACC
CTTTCCTGGGGATGATTATGGGCCTCGGAGGAGGCATGGACTTTGACTCCAAGAAGGCCTACAGGGACGT
GGCCTGGCTGGGTGAATGCGACCAGGGCTGCCTGGCCCTTGCTGAGCTCCTTGGATGGAAGAAGGAGCTG
GAGGACCTTGTCCGGAGGGAGCACGCCAGCATAGATGCCCAGTCGGGGGCGGGGGTCCCCAACCCCAGCA
CTTCAGCTTCCCCCAAGAAGTCCCCGCCACCTGCCAAGGACGAGGCCAGGACAACAGAGAGGGAGAAACC
CCAGTGACAGCTGCATCTCCCAGGCGGGATGCCGAGCTCCTCAGGGACAGCTGAGCCCCAACCGGGCCTG
GCCCCCTCTTAACCAGCAGTTCTTGTCTGGGGAGCTCAGAACATCCCCCAATCTCTTACAGCTCCCTCCC
CAAAACTGGGGTCCCAGCAACCCTGGCCCCCAACCCCAGCAAATCTCTAACACCTCCTAGAGGCCAAGGC
TTAAACAGGCATCTCTACCAGCCCCACTGTCTCTAACCACTCCTGGGCTAAGGAGTAACCTCCCTCATCT
CTAACTGCCCCCACGGGGCCAGGGCTACCCCAGAACTTTTAACTCTTCCAGGACAGGGAGCTTCGGGCCC
CCACTCTGTCTCCTGCCCCCGGGGCCTGTGGCTAAGTAAACCATACCTAACCTACCCCAGTGTGGGTGT
GGGCCTCTGAATATAACCCACACCCAGCGTAGGGGAGTCTGAGCCGGGAGGGCTCCCGAGTCTCTGCCT
TCAGCTCCCAAAGTGGGTGGTGGGCCCCCTTCACGTGGGACCCACTTCCCATGCTGGATGGGCAGAAGAC
ATTGCTTATTGGAGACAAATTAAAAACAAAAACAACTAACAA

*FIG. 17*

>NP_060496.2 phosphofurin acidic cluster sorting protein 1 [Homo sapiens]
MAERGGAGGGPGGAGGGSGQRGSGVAQSPQQPPPQQQQQQPPQQPTPPKLAQATSSSSSTSAAAASSSSS
STSTSMAVAVASGSAPPGGPGPGRTPAPVQMNLYATWEVDRSSSSCVPRLFSLTLKKLVMLKEMDKDLNS
VVIAVKLQGSKRILRSNEIVLPASGLVETELQLTFSLQYPHFLKRDANKLQIMLQRRKRYKNRTILGYKT
LAVGLINMAEVMQHPNEGALVLGLHSNVKDVSVPVAEIKIYSLSSQPIDHEGIKSKLSDRSPDIDNYSEE
EEESFSSEQEGSDDPLHGQDLFYEDEDLRKVKKTRRKLTSTSAITRQPNIKQKFVALLKRFKVSDEVGFG
LEHVSREQIREVEEDLDELYDSLEMYNPSDSGPEMEETESILSTPKPKLKPFFEGMSQSSSQTEIGSLNS
KGSLGKDTTSPMELAALEKIKSTWIKNQDDSLTETDTLEITDQDMFGDASTSLVVPEKVKTPMKSSKTDL
QGSASPSKVEGVHTPRQKRSTPLKERQLSKPLSERTNSSDSERSPDLGHSTQIPRKVVYDQLNQILVSDA
ALPENVILVNTTDWQGQYVAELLQDQRKPVVCTSTVEVQAVLSALLTRIQRYCNCNSSMPRPVKVAAVG
GQSYLSSILRFFVKSLANKTSDWLGYMRFLIIPLGSHPVAKYLGSVDSKYSSSFLDSGWRDLFSRSEPPV
SEQLDVAGRVMQYVNGAATTHQLPVAEAMLTCRHKFPDEDSYQKFIPFIGVVKVGLVEDSPSTAGDGDDS
PVVSLTVPSTSPPSSSGLSRDATATPPSSPSMSSALAIVGSPNSPYGDVIGLQVDYWLGHPGERRREGDK
RDASSKNTLKSVFRSVQVSRLPHSGEAQLSGTMAMTVVTKEKNKKVPTIFLSKKPREKEVDSKSQVIEGI
SRLICSAKQQQTMLRVSIDGVEWSDIKFFQLAAQWPTHVKHFPVGLFSGSKAT >NM_018026.4 Homo sapiens phosphofurin acidic cluster sorting protein 1
(PACS1), mRNA
ACCCGTGTCGGCCTCGCGAGCCGCAACAGGCAGCGGCGGTCGAGCGCGAGGCCCGCGCGCCCAGAGGCCC
CGCGCGTGCGTGCAGCTCGCTGGCTGCTCGCGCTCGGGCAGGCGGGCTGAGGAGGCTGCCGCGCCCCGC
CGCCGCCGCCGCGGGGGAAGCCTGGGAGCCAGATCGGCGTCGCCTCGGCCTCCGTAACCCCCGCCTAGCC
GGGCCATGGCGGAACGCGGAGGGGCGGGCGGTGGTCCCGGAGGCGCCGGGGGCGGCAGCGGCCAGCGGGG
ATCCGGGGTCGCCCAGTCCCCTCAGCAGCCGCCGCCGCAGCAGCAGCAGCAGCCGCCGCAGCAGCCG
ACGCCCCCAAGCTGGCCCAGGCCACCTCGTCGTCCTCGTCCACCTCGGCGGCGGCTGCCTCCTCCTCGT
CCTCGTCTACCTCCACCTCCATGGCCGTGGCGGTGGCCTCGGGCTCCGCGCCTCCCGGTGGCCCGGGGCC
AGGCCGCACCCCCGCCCCGGTGCAGATGAACCTGTACGCCACCTGGGAGGTGGACCGGAGCTCGTCCAGC
TGCGTGCCTAGGCTATTCAGCTTGACCCTGAAGAAACTCGTCATGCTAAAAGAAATGGACAAAGATCTTA
ACTCAGTGGTCATCGCTGTGAAGCTGCAGGGTTCAAAAAGAATTCTTCGCTCCAACGAGATCGTCCTTCC
AGCTAGTGGACTGGTGGAAACAGAGCTCCAATTAACCTTCTCCCTTCAGTACCCTCATTTCCTTAAGCGA
GATGCCAACAAGCTGCAGATCATGCTGCAAAGGAGAAAACGTTACAAGAATCGGACCATCTTGGGCTATA
AGACCTTGGCCGTGGGACTCATCAACATGGCAGAGGTGATGCAGCATCCTAATGAAGGCGCACTGGTGCT
TGGCCTACACAGCAACGTGAAGGATGTCTCTGTGCCTGTGGCAGAAATAAAGATCTACTCCCTGTCCAGC
CAACCCATTGACCATGAAGGAATCAAATCCAAGCTTTCTGATCGTTCTCCTGATATTGACAATTATTCTG
AGGAAGAGGAAGAGAGTTTCTCATCAGAACAGGAAGGCAGTGATGATCCATTGCATGGGCAGGACTTGTT
CTACGAAGACGAAGATCTCCGGAAAGTGAAGAAGACCCGGAGGAAACTAACCTCAACCTCTGCCATCACA
AGGCAACCTAACATCAAACAGAAGTTTGTGGCCCTCCTGAAGCGGTTTAAAGTTTCAGATGAGGTGGGCT
TTGGGCTGGAGCATGTGTCCCGCGAGCAGATCCGGGAAGTGGAAGAGGACTTGGATGAATTGTATGACAG
TCTGGAGATGTACAACCCCAGCGACAGTGGCCCTGAGATGGAGGAGACAGAAAGCATCCTCAGCACGCCA
AAGCCCAAGCTCAAGCCTTTCTTTGAGGGGATGTCGCAGTCCAGCTCCCAGACGGAGATTGGCAGCCTCA
ACAGCAAAGGCAGCCTCGGAAAAGACACCACCAGCCCTATGGAATTGGCTGCTCTAGAAAAAATTAAATC
TACTTGGATTAAAAACCAAGATGACAGCTTGACTGAAACAGACACTCTGGAAATCACTGACCAGGACATG
TTTGGAGATGCCAGCACGAGTCTGGTTGTGCCGGAGAAAGTCAAAACTCCCATGAAGTCCAGTAAAACGG
ATCTCCAGGGCTCTGCCTCCCCCAGCAAAGTGGAGGGGGTGCACACACCCCGGCAGAAGAGGAGCACGCC
CCTGAAGGAGCGGCAGCTCTCCAAGCCCCTAAGTGAGAGGACCAACAGTTCCGACAGCGAGCGCTCCCCA
GATCTGGGCCACAGCACGCAGATTCCAAGAAAGGTGGTGTATGACCAGCTCAATCAGATCCTGGTGTCAG
ATGCAGCCCTCCCAGAAAATGTCATTCTGGTGAACACCACTGACTGGCAGGGCCAGTATGTGGCTGAGCT
GCTCCAGGACCAGCGGAAGCCTGTGGTGTGCACCTGCTCCACCGTGGAGGTCCAGGCCGTGCTGTCCGCC
CTGCTCACCCGGATCCAGCGCTACTGCAACTGCAACTCTTCCATGCCGAGGCCAGTGAAGGTGGCTGCTG
TGGGAGGCCAGAGCTACCTGAGCTCCATCCTCAGGTTCTTTGTCAAGTCCCTGGCCAACAAGACCTCCGA
CTGGCTTGGCTACATGCGCTTCCTCATCATCCCCCTCGGTTCTCACCCTGTGGCCAAATACTTGGGGTCA
GTCGACAGTAAATACAGTAGTTCCTTCCTGGATTCTGGTTGGAGAGATCTGTTCAGTCGCTCGGAGCCAC
CAGTGTCAGAGCAACTGGACGTGGCAGGGCGGGTGATGCAGTACGTCAACGGGGCAGCCACGACACACCA
GCTTCCCGTGGCCGAAGCCATGCTGACTTGCCGGCATAAGTTCCCTGATGAAGACTCCTATCAGAAGTTT
ATTCCCTTCATTGGCGTGGTGAAGGTGGGTCTGGTTGAAGACTCTCCCTCCACAGCAGGCGATGGGGACG

FIG. 18A

```
ATTCTCCTGTGGTCAGCCTTACTGTGCCCTCCACATCACCACCCTCCAGCTCGGGCCTGAGCCGAGACGC
CACGGCCACCCCTCCCTCCTCCCCATCTATGAGCAGCGCCCTGGCCATCGTGGGGAGCCCTAATAGCCCA
TATGGGGACGTGATTGGCCTCCAGGTGGACTACTGGCTGGGCCACCCCGGGGAGCGGAGGAGGGAAGGCG
ACAAGAGGGACGCCAGCTCGAAGAACACCCTCAAGAGTGTCTTCCGCTCAGTGCAGGTGTCCCGCCTGCC
CCATAGTGGGGAGGCCCAGCTTTCTGGCACCATGGCCATGACTGTGGTCACCAAAGAAAAGAACAAGAAA
GTTCCCACCATCTTCCTGAGCAAGAAACCCGAGAAAAGGAGGTGGATTCTAAGAGCCAGGTCATTGAAG
GCATCAGCCGCCTCATCTGCTCAGCCAAGCAGCAGCAGACTATGCTGAGAGTGTCCATCGATGGGGTCGA
GTGGAGTGACATCAAGTTCTTCCAGCTGGCAGCCCAGTGGCCCACCCATGTCAAGCACTTTCCAGTGGGA
CTCTTCAGTGGCAGCAAGGCCACCTGAGGCCCTGTCTCCCAGCCACTTTCCCTCCTGGCACTGCCACCAG
CCTCACCGCCTGCGGGCAGGGGGAGGCCAGCAGGCCCGGGCCCAGCACCCCTTCCCTGGCACCAGGGTCT
GCCTCTCACTCGCCCAGGTCCCGAAGGACACTGCCACAGGGACGCCTTCCCTCCCCTCCCCTCCAGCCCA
CCCCTGCACAGCCCCTCCTCCTTCCCGCTTTTCCCCTTCTCCCTCCTGCTCCAGGCCCAAGGCGTGTTGG
TTTTGCCTTCTGGTGCCCATAGTCCCCTGGACTGAGTCCCCAGGCCTTCCTTCACCCGACTTCCAAACT
CTTCCTTGTGGTATCAGTTTCCTTCTCGGAAATGAGAAAGCTGGAATCCTGGTCCCCAGCAGGAGAGCCT
AGTCCTCCCCCAGCCCCTCCAGCCACCAGGGTGTCCTCTAGGATGCAGCTGCCAGATCCACTCACTCTGC
TGCCTCCAGCAGGACCCAAGGCCACTTTCAACTCTTATGGGGTTCTCCACCTGCCCCAGAGCTTCTCAAG
GGAGGGTAAGGGGGCACCCTGAGCCCACAGGACCCCTACTTCACAGCTCACAGGGGCAGGAGGCAGCTCC
CCTGCCTCCAGGACCCTGTTGCTATGGTGACACAGCGTTTCTAGGACAGAGGGGCCTCCCAGTCTCCCCC
CACCACCCGTGCACGACTTCCTCACCACCCCCAGGTTCCCTGCAGATGTCGTGTGTGTCCTGAGTGTTTC
TTTGGTTCTTTGCACGCCAAGTCTCTTGGTTGTACCATGTGACACACCCTGTGCACTGGTCGCTGTCTTC
GTGGCTTCCACCCTTGTTAATGATGCTCCTGCCTCTGCCTCCCAGCCCCTCACCCAGCACAGCTCTGCCT
GGACTTGGAGAGATGGGAGGCAGACCCCCACCACCATACATGCTGTCTGTGGCCCCTCAGACATTCTGTT
TCATCTCCCATTCATCTCCCTCCTCCCACCGTGTCAGTTTTCTGCCTTTCCCTGCTCTGTTCTTCCCCC
TCCTTAGGCCCCAGCCTGGGCCCAGACCCATCCTCCCAGCCAGGTTTCCCTCCAGCAGGCTCCTTCCCTC
CCTGTCACCTCCCTCTCACCAACCCGGGGTCTGAGCCCCTCATTCCTGACCGTCCGTGTTCTCAGGAGTG
GTTGAGGACACAGGGCCCCAGCCCAGCCCTCTGCACCCCCAGCCCGGCCATCTGCGCCCACAGCCCCT
TTGGAGCTTTTCTCTTGTCCTCTCACTCCTTCCCAGAAGTTTTTGCACAGAACTTCATTTTGAAAGTGTT
TTTCTCATTCTCCATACCTCCCCCAAGCTCTCCTCCAGCCCTTCCCAGGGCTCAGCCCTGCTGTCCTGAG
CGTCTCCTGGGCCAGAGAGAGGAGATGGGGGTGGGAGGGACTGAGTTGATGTTGGGTTTTTCATTCAATA
AATTGGTGATTTCTTACCGAC
```

FIG. 18B

>sp|Q86VP3|PACS2_HUMAN Phosphofurin acidic cluster sorting protein 2
OS=Homo sapiens OX=9606 GN=PACS2 PE=1 SV=3
MAERGRLGLPGAPGALNTPVPMNLFATWEVDGSSPSCVPRLCSLTLKKLVVFKELEKELI
SVVIAVKMQGSKRILRSHEIVLPPSGQVETDLALTFSLQYPHFLKREGNKLQIMLQRRKR
YKNRTILGYKTLAAGSISMAEVMQHPSEGGQVLSLCSSIKEAPVKAAEIWIASLSSQPID
HEDSTMQAGPKAKSTDNYSEEEYESFSSEQEASDDAVQGQDLDEDDFDVGKPKKQRRSIV
RTTSMTRQQNFKQKVVALLRRFKVSDEVLDSEQDPAEHIPEAEEDLDLLYDTLDMEHPSD
SGPDMEDDDSVLSTPKPKLRPYFEGLSHSSSQTEIGSIHSARSHKEPPSPADVPEKTRSL
GGRQPSDSVSDTVALGVPGPREHPGQPEDSPEAEASTLDVFTERLPPSGRITKTESLVIP
STRSEGKQAGRRGRSTSLKERQAARPQNERANSLDNERCPDARSQLQIPRKTVYDQLNHI
LISDDQLPENIILVNTSDWQGQFLSDVLQRHTLPVVCTCSPADVQAAFSTIVSRIQRYCN
CNSQPPTPVKIAVAGAQHYLSAILRLFVEQLSHKTPDWLGYMRFLVIPLGSHPVARYLGS
VDYRYNNFFQDLAWRDLFNKLEAQSAVQDTPDIVSRITQYIAGANCAHQLPIAEAMLTYK
QKSPDEESSQKFIPFVGVVKVGIVEPSSATSGDSDDAAPSGSGTLSSTPPSASPAAKEAS
PTPPSSPSVSGGLSSPSQGVGAELMGLQVDYWTAAQPADRKRDAEKKDLPVTKNTLKCTF
RSLQVSRLPSSGEAAATPTMSMTVVTKEKNKKVMFLPKKAKDKDVESKSQCIEGISRLIC
TARQQQNMLRVLIDGVECSDVKFFQLAAQWSSHVKHFPICIFGHSKATF >NM_001100913.3 Homo sapiens phosphofurin acidic cluster sorting protein 2
(PACS2), transcript variant 1, mRNA
GCAGCTCGTCGCCGCCCGCGGGCCTGTCCGACGCCGGGCCCGGCCCGTCCCCTCCGCCGCCCGGCAGCC
ATGTGACCGCGCCGCCGCCCTCCGCGCGCCCGGCCCGCCCGCCGCGCGTCCGCGGCCCGGCCGCAGCCCC
AGGCCGCCGAGGGAGCGGCGGGGCCGGCGCCATGGCCGAGCGAGGCCGCCTCGGCCTCCCCGGCGCGCCC
GGCGCGCTCAACACGCCCGTGCCCATGAACCTGTTCGCCACCTGGGAGGTGGACGGCTCCAGCCCCAGCT
GCGTGCCCAGGTTGTGCAGCCTGACTCTGAAGAAGCTGGTGGTCTTCAAGGAGCTGGAGAAGGAGCTGAT
CTCCGTGGTGATCGCTGTCAAGATGCAGGGCTCCAAACGAATCCTGCGGTCCCATGAGATTGTGCTGCCC
CCCAGTGGACAAGTGGAGACAGACCTGGCCCTGACCTTCTCCTTGCAGTATCCTCACTTCTTGAAGAGGG
AAGGCAACAAGCTTCAGATCATGCTGCAGCGCAGAAAGCGCTACAAGAACAGAACCATCCTGGGCTACAA
GACGCTGGCCGCGGGCTCCATCAGCATGGCTGAGGTGATGCAACACCCGTCTGAAGGTGGCCAGGTGCTG
AGCCTCTGCAGCAGCATCAAGGAGGCCCCCGTCAAGGCGGCCGAGATCTGGATCGCCTCCCTGTCCAGCC
AGCCCATTGACCACGAAGACAGCACCATGCAGGCCGGCCCCAAGGCCAAGTCCACGGATAACTACTCCGA
GGAGGAGTATGAGAGCTTCTCCTCCGAGCAGGAGGCCAGTGACGACGCCGTGCAGGGGCAGGACTTGGAC
GAGGACGACTTTGACGTGGGGAAGCCGAAGAAGCAGCGGAGATCGATTGTAAGAACGACGTCCATGACCA
GGCAACAGAACTTCAAGCAGAAAGTGGTAGCGCTGCTGCGGAGGTTCAAAGTGTCCGACGAGGTCCTGGA
CTCGGAGCAGGACCCTGCGGAGCACATCCCCGAGGCAGAGGAGGACCTGGACCTCCTGTATGACACCCTG
GACATGGAGCACCCCAGCGACAGCGGCCCCGACATGGAGGATGACGACAGCGTCCTCAGCACCCCCAAGC
CGAAGCTGCGGCCATACTTTGAAGGCCTGTCGCACTCGAGCTCGCAGACGGAGATTGGGAGCATCCACAG
CGCCCGCAGCCACAAGGAGCCCCCAAGCCCGGCTGACGTGCCCGAGAAGACGCGGTCCCTGGGAGGCAGG
CAGCCGAGCGACAGTGTCTCTGACACGGTGGCCCTCGGTGTGCCAGGCCCGAGGGAGCACCCTGGACAGC
CTGAGGACAGCCCCGAGGCTGAGGCCTCCACCCTGGATGTGTTCACGGAGAGGCTGCCGCCCAGCGGGAG
GATCACCAAGACAGAGTCCCTTGTCATCCCCTCCACCAGGTCCGAGGGGAAGCAGGCTGGCCGACGGGGC
CGGAGCACATCCTTGAAGGAGCGGCAGGCAGCACGGCCCCAGAATGAGCGGGCCAACAGCCTGGACAACG
AGCGCTGCCCGGACGCCCGGAGCCAGCTACAGGTGCAGCTGCAGATCCCCAGGAAGACTGTGTATGACCA
GCTCAACCACATCCTCATCTCCGATGACCAGCTTCCCGAAAACATCATCCTTGTCAACACCTCGGACTGG
CAGGGGCAGTTCCTCTCCGACGTCCTGCAGAGGCACACGCTCCCCGTGGTGTGCACGTGCTCTCCTGCGG
ACGTCCAGGCGGCCTTCAGCACCATCGTCTCACGGATACAGAGATACTGCAACTGCAATTCCCAGCCCCC
GACCCCCGTGAAGATCGCCGTGGCGGGAGCGCAGCATTACCTCAGTGCCATCCTGCGGCTCTTTGTGGAG
CAGCTGTCCCACAAGACACCCGACTGGCTCGGCTACATGCGCTTCCTGGTCATCCCACTGGGCTCCCACC
CCGTGGCCAGGTACCTAGGCTCCGTGGACTACCGCTACAACAACTTCTTCCAGGACCTGGCCTGGAGAGA
CCTGTTCAACAAGCTGGAGGCCCAGAGTGCGGTACAGGACACGCCAGACATTGTGTCACGCATCACGCAG
TACATCGCAGGGGCCAACTGTGCCCACCAGCTCCCCATCGCAGAGGCCATGCTGACCTACAAGCAGAAGA
GGAAAAAGCATTTTCATTTTGACTTTACCCTAAGCCCTGACGAAGAGTCCTCCCAAAAGTTCATTCCCTT
TGTCGGGGTTGTGAAGGTTGGAATTGTGGAGCCATCCTCGGCCACATCAGGCGACTCGGACGACGCGGCC
CCCTCGGGCTCTGGCACGCTCTCCTCCACCCCGCCGTCCGCATCTCCTGCGGCCAAGGAGGCCTCACCCA
CCCCGCCCTCCTCCCCGTCGGTGAGCGGAGGCCTGTCCTCCCCCAGCCAGGGTGTCGGCGCCGAGCTGAT
GGGGCTGCAGGTGGACTACTGGACGGCAGCACAGCCTGCGGACAGGAAGAGGGACGCCGAGAAGAAGGAC

FIG. 19A

```
CTGCCTGTCACCAAAAACACGCTCAAGTGCACTTTCCGGTCCCTCCAGGTCAGCAGGCTGCCCAGCAGCG
GCGAGGCTGCAGCCACGCCCACCATGTCCATGACCGTGGTCACCAAGGAGAAGAACAAGAAGGTGATGTT
TCTGCCCAAGAAAGCGAAGGACAAGGACGTGGAGTCTAAGAGCCAGTGCATTGAGGGCATCAGCCGGCTC
ATCTGCACTGCCAGGCAGCAGCAGAACATGCTGCGGGTCCTCATCGACGGCGTGGAGTGCAGCGACGTCA
AGTTCTTCCAGCTGGCCGCGCAGTGGTCCTCGCACGTGAAGCACTTCCCCATCTGCATCTTCGGACACTC
CAAGGCCACCTTCTAGCCCCACCCACCAGGGGGCCCACCTCCTGCCCCATGCTGTGAGGGGCCCAGCTGC
ATTTCTGTTAACATTTCAGTTTACTACAGAGACAGACGCTTAAAACACAAAGAGAAACAGTCTTAAGTAT
GAATGTGCTCACAACGTGGAAACTAACGGGGGAGCTCCTGCCAGGAGCCGAATAACTGCTCTGCTTATTA
ACCCGAACGTTCGGCCCGGGGCTGGGAAGCCAGAAGGACGATGCTGAGCCATGGATCGCGGAAGGCGTCC
TCTGGCCTCAGGAGCCACCCAGAGCCTCACAGGCTGAGTTCTTGCCTCTGTGTCCTGTCCTTCCTGGAAG
TCAGGACTCTGCTTCCTCAGGGAGCCCGGGGAAGGCGGAGCTCAGTGGCCACAGGCCGAGGGCCATGGGG
CCGCTCAGTCCCGTTGGGGTTGTCCTGAGTTGAGCCTGGGGGGGCCGTCCTGCCCGCCTAAGAGATGCCC
CCAGCACCGCACACTCGTGGTTCCCAATAAACTCCTGCCTGCGGCGGAGGTTTTATAGCAGCAGATATTT
TTAATGCTTTTCAATACATGTTCTAATGTAGCTGCCAAACATGTTGCTCTTCTGAAGTCCCCCTGGGGCT
GGGCAGAGCCAGCAGAGCCTGCCCCCACTTCCCCAGCCCCTGCCCCACCCCGCCTCACACCTTCCCCACT
CTCAGGCTGTTCTTGAAACACCATGAGGCTTCTGCGTGTAGTCCCTGCCCCAAACTTAGCAAGCACAGGG
GCCTCCACAGCCCAGGTGGCCCCAGAAAATGTTCCAGAGCCCAGCTTGGTACATAGTGAGATGCTGCTGG
GGTTGGCCTGAGGTGGGGCCACTTCCTCCACCCCAGTGGGTATGTCTGAGGTCAGCCATGGGGATATCT
GGGTTGAGATTCAGGTTTTGGTGAATATGGGGCAGGCGTCCAGATGTGTTTGTGTCACCTGCTGCAACGC
TGTAGCCAATGAAGATTCCAGCGGGATGGCCTGACCAGCGGGGCCGGCACTTTGGAGCCGTGGGTGCAGC
CAGGTACCCCGTGCAGGGCCTGGGAGGCTCTCCAGGCCACAGTCCTCAGAGCGTGTTGGGTCCCATGTTG
TGTGTGGGTTCCATGCCCTCCACACAGCAGGAGAGGGCTTCCCTGACCACACCTGCCCCCTCAGTCCTGC
TTCTCCCCAGTAAGCCTGCACTGTGGGGTCTCCATAGGAGGAGCTGGGGAAGCTGGGGCCCTCCCAGGGG
TCCTGATCGACCCTGGGGGCTCTTGGCCTGGTTTCGTAAGATGGAGCACTGCAAAAGGCCATGCTCAGAA
AGCAAACGCAGGGCAGGGTGGGCCTCGAGCCGGGGCTGGAGGGGTCTCCACCCTTGCTGGCCTGAGAGAT
GGCCCACATTTCTTACTTGTGACCGCCCTGCTCTTCCTGGCCGCCCCCCCAGGTGGCTGAACAGGGTGA
TTTTGTTGTGGTGAGGGGCCAGGATGTGGCCTGGTGTGCAGCCTCAGCTCCCTGGGTTCAGGCCTCAGAG
GTAGCCTGTGTGCAGGAGGCAGAGCCCCAGCCCCTCCCAGCCAGAGCCCCTCCACACCAGGGACTCCTCC
TTCACCTGGGACCAGGAGCCTGGGGCACACCCCAGGGTGGGGAGAGGGTAGGAAGGTCTCCCATTGAAT
CCTGGCTTCAGGCTCTGCCCCGAGAAGTGTCTGCGGTGAGGGTGTGAGCCCCGGGCTGATGGCCTCTGAC
CCCGGCAACAGGTGGGACCCTGACTGACTCGTTCAGCTGCCCCCAAGCTGGGCTGCAGAGCATCTGTTTT
TCTGCTCTCCAGTTTCTTTTCTTTTTTTTTTTTTTTTTTTTTGAGATGGAGTCTTGCTCTGTTGCCCAGG
CTGGAGTGCAGTGGCATGATCTCAGCTCACTGCAGCCTCCGTCTCCCAGGTTCAAGCAGTTCTCCTGCCT
CAGCCTCCCGAGTAGCTGGGATTACAGGCGTGTGCCACCACACCTGGCTATTTTTTTGTATTTTTAGTA
GAGATGGGGTTTTGCCATGTTGGCCAGGCTGGTCTTGAACTCCTGACCTCAAGTGATCCACCCGCCTCGG
CCTCCCAAAGTGCTGGGATTACAGGCGTGAGTCACCGCGTCCTGCCTGCTCTTCCTGTTTCTTTCCCAAG
GGTCACACTCAGTAGGGAGATGAAGGTGGAAACATCCTTGCTGTGGCTTTCTGGCCTCAGAGCAGGTTTT
AGAGGAAGGGGCCACAGGCTGCCTAGTGCATCCTGGCTGTGGGCAGCCCCTTTCCTGGAGCCCTCCTGCC
TACCCCGTACCTCCCATCTGGCTGCACAGCTCCATCCTTAGCCACGCAAGGGGAGAACATGGGCAGAGTC
TCCATCCAGCAGCTGGGGGTTCTGGTGGCACTCCCTGTGCCCCTGCTGCTGCTGGGCTGTGGGTCTGCCC
TGCACCCAGGAGCCCCACGGTCCATCCCCCACACCATGCCCAGCACCAGGGAGGTTGGGCAGACAAGACC
TGGGCCATGCCAGCCCTCTGTGCCTCGGTTTTCCCACTGGTTACACAGGATGGTCGCATTTTCCCTGCCT
ACCTCACAGAGCTGTTCTGAGGGTGCATGGAGGAGCACTCTGTCCCACCAAGGACAACTAGAAACCAAAG
CCATCTGACAGCCAGTGCGGTAAGGGCGGGGGATGTGTGTGAGGTGTGCACACCCCCGAGAACCTGG
CCCTGGACTGGCCTCACAGGACAGGAGGCAGCCCCTTGTAGAGCTAGGGCTCAGCCCCATCAGTCTCAAA
GGTTAAGCCACCAGTCACCACCGAGGCACCCTCAGGCCTGGTGGCCACTGTCCACTATTACGTAGACAG
ACCCCACCCTCACCCAGGCCAGCTGTGGGCCAGTCCCGCCCTGCAATCTGGTCTGCTGCCTTCCTCTTCC
ATGTTGGTCCCCTTGGCCACTGTCTCTGGGCATGCAAGCCAGTGTCCTGGTTCAGTGCCTCGGCCAGAGC
TGGGGCAGGAGAGGGGCCTCTGGGTGAGAGCTGGGGGTGTCTCTGCAGGGTACTGGCAGCCTTGCCACAC
TGTCCTCATTCCCAGATGGAAAGACCTGAGTGCCTCTCGCCTTCCTCCGGGAATGAATTCCTCATGAAAA
TGACCAGGCCACTTCTTCCGAGGGCCAGGCCGCCCCCTCCCCGAGACCTGTCCTGCCGTCCGCGGGTGTG
TGGCCTGTAGGGGACTGAGAGCTGGGCTTGCTGGGCACCTCTGGAATCTGACCCTGTGGGCCAAAGAAGC
ACCACTGTAGTTTCTGCAGACCCCCATGCGGTTCATTGTGCATTGTTTGGTTTCTAGGATGTATGTGTTG
CTAGTTTTTTTTAATGAAACCCTGGATTAATGTAAATAGCTTTTTGGGGAACGGATTCTAATGTCACGTA
TGTGACCGTGTGGACTATTTCAAGGTGCTGATGCAACACTAATAAACCTGGAGGGGCCGGC
```

*FIG. 19B*

METHODS OF TREATING PACS1 AND PACS2 SYNDROMES

CROSS REFERENCE TO RELATED APPLICATIONS

This application is the United States national phase of International Application No. PCT/US2019/042172 filed Jul. 17, 2019, and claims the benefit of U.S. Provisional Patent Application No. 62/699,330, filed Jul. 17, 2018, the disclosures of which are hereby incorporated by reference in their entirety.

The Sequence Listing associated with this application is filed in electronic format via EFS-Web and is hereby incorporated by reference into the specification in its entirety. The name of the text filed containing the Sequence Listing is 6527_2007000_ST25.txt. The size of the text file is 53,084 bytes, and the text filed was created Jan. 13, 2021.

Neurodevelopmental disorders are an amalgam of neuropsychiatric phenotypes characterized by developmental delay, intellectual disability, autistic features, and epilepsy. The underlying genetic causes are frequently complex and allelically diverse, and further confounded by the grouping of CNS diseases based on their end-stage symptoms instead of an ensemble of discrete genetic and pathological subgroups. Consequently, the biological pathways that become dysregulated to drive these disorders remain poorly understood, hampering effective therapeutic intervention.

Next-generation sequencing methods marked a significant advance in our ability to understand and treat neurodevelopmental disorders. In particular, trio sequencing methods identified recurrent de novo missense mutations in a handful of genes that cause neurodevelopmental disorders, presumably due to a gain-of-function effect. One of these gene is PACS1 (phosphofurin acidic cluster sorting protein-1), in which a recurrent de novo missense mutation, c.607C>T (p.Arg203Trp (PACS1R203W), see FIG. 1), which occurs in the critical PACS1 cargo(furin) binding region (FBR) (Thomas, G., Aslan, J. E., Thomas, L., Shinde, P., Shinde, U., and Simmen, T. (2017). Caught in the act-protein adaptation and the expanding roles of the PACS proteins in tissue homeostasis and disease. J Cell Sci 130, 1865-1876). This mutation was identified in a series of patients that share an overlapping phenotype, including developmental delay, intellectual disability, seizures and characteristic craniofacial dysmorphisms. This syndrome is referred to as PACS1 syndrome (also known as Schuurs-Hoeijmakers Syndrome). A second member of these newly identified genes is PACS2, which incurs a recurrent de novo mutation at c.625G>A (p.Glu209Lys (PACS2E209K), which is located in an autoregulatory segment within the middle region (MR, see also FIG. 1). Children carrying this mutation suffer from several characteristics described for PACS1 Syndrome, in addition to profound cerebellar dysgenesis. The mechanism(s) by which PACS1R203W and PACS2E209K cause PACS1 or PACS2 Syndromes is unknown and there are currently no curative treatments.

PACS1 and PACS2 act as multi-functional homeostatic regulators using both in vitro and in vivo systems (Thomas, G., et al. (2017). J Cell Sci 130, 1865-1876 and Wan, L., Molloy, S. S., Thomas, L., Liu, G., Xiang, Y., Rybak, S. L., and Thomas, G. (1998). PACS-1 defines a novel gene family of cytosolic sorting proteins required for trans-Golgi network localization. Cell 94, 205-216). PACS-1 has central roles in both the cytoplasm and nucleus. In the cytoplasm, PACS-1 modulates the trafficking of client proteins, including receptors, proteases and ion channels between endosomes and the trans-Golgi Network (TGN). In epithelial cells and neurons, PACS1 mediates trafficking of proteins to the primary cilium (Jenkins, P. M., Zhang, L., Thomas, G., and Martens, J. R. (2009). PACS-1 mediates phosphorylation-dependent ciliary trafficking of the cyclic-nucleotide-gated channel in olfactory sensory neurons. J Neurosci 29, 10541-10551 and Schermer, B., Hopker, K., Omran, H., Ghenoiu, C., Fliegauf, M., Fekete, A., Horvath, J., Kottgen, M., Hackl, M., Zschiedrich, S., et al. (2005). Phosphorylation by casein kinase 2 induces PACS-1 binding of nephrocystin and targeting to cilia. EMBO J 24, 4415-4424). Cytoplasmic PACS2 modulates endosomal trafficking and communication between the ER and mitochondria (Aslan, J. E., You, H., Williamson, D. M., Endig, J., Youker, R. T., Thomas, L., Shu, H., Du, Y., Milewski, R. L., Brush, M. H., et al. (2009). Akt and 14-3-3 control a PACS-2 homeostatic switch that integrates membrane traffic with TRAIL-induced apoptosis. Mol Cell 34, 497-509; Atkins, K. M., Thomas, L., Youker, R. T., Harriff, M. J., Pissani, F., You, H., and Thomas, G. (2008). HIV-1 Nef binds PACS-2 to assemble a multikinase cascade that triggers major histocompatibility complex class I (MHC-I) down-regulation: analysis using short interfering RNA and knock-out mice. J Biol Chem 283, 11772-11784; and Simmen, T., Aslan, J. E., Blagoveshchenskaya, A. D., Thomas, L., Wan, L., Xiang, Y., Feliciangeli, S. F., Hung, C. H., Crump, C. M., and Thomas, G. (2005). PACS-2 controls endoplasmic reticulum-mitochondria communication and Bid-mediated apoptosis. EMBO J 24, 717-729). In the nucleus, the PACS proteins regulate the action of SIRT1 and other histone deacetylases (HDACs) to modulate gene expression and DNA replication repair (Krzysiak, T. C., Thomas, L., Choi, Y. J., Auclair, S., Qian, Y., Luan, S., Krasnow, S. M., Thomas, L. L., Koharudin, L. M. I., Benos, P. V., et al. (2018). An Insulin-Responsive Sensor in the SIRT1 Disordered Region Binds DBC1 and PACS-2 to Control Enzyme Activity. Mol Cell 72, 985-998 e987, and unpublished findings).

Genetic, biochemical and cell biology studies reveal PACS1 R203W and PACS2E209K dysregulate centrosome function, altering Golgi positioning, microtubule organization and the integrity of the primary cilium. PACS1R203W acts as a gain-of-function mutation that increases the interaction between PACS-1 and HDAC6, which is a cytoplasmic class IIb deacetylase that modulates neuronal plasticity and is a regulator of both microtubule and centrosomal/ciliary function. Altered HDAC6 function impedes neural development, resulting in neuropsychiatric behaviors-processes that can be corrected by treatment of animals with therapeutic HDAC6 inhibitors (Fukuda, T., Nagashima, S., Abe, T., Kiyonari, H., Inatome, R., and Yanagi, S. (2016). Rescue of CAMDI deletion-induced delayed radial migration and psychiatric behaviors by HDAC6 inhibitor. EMBO Rep 17, 1785-1798). By contrast, PACS2E209K dysregulates SIRT2, a class III deacetylase that is emerging as a target in neurologic disorders (de Oliveira, R. M., Vicente Miranda, H., Francelle, L., Pinho, R., Szego, E. M., Martinho, R., Munari, F., Lazaro, D. F., Moniot, S., Guerreiro, P., et al. (2017). The mechanism of sirtuin 2-mediated exacerbation of alpha-synuclein toxicity in models of Parkinson disease. PLOS Biol 15, e2000374 and Silva, D. F., Esteves, A. R., Oliveira, C. R., and Cardoso, S. M. (2017). Mitochondrial Metabolism Power SIRT2-Dependent Deficient Traffic Causing Alzheimer's-Disease Related Pathology. Mol Neurobiol 54, 4021-4040).

SUMMARY

In one aspect or embodiment of the subject matter disclosed herein, a method of treating PACS1 Syndrome in a patient is provided. The method comprises administering to the patient an amount of an HDAC6 inhibitor effective to treat PACS1 Syndrome in a patient, or knocking down PACS1 or HDAC6 expression in the patient.

In another aspect or embodiment, a method of restoring Golgi morphology in a cell, such as a human cell, having a mutation in a PACS1 gene, such as PACS1 (Arg203Trp) PACS1$^{R203W}$, (e.g., SEQ ID NO: 5) mutation is provided. The method comprises administering to the patient an amount of an HDAC6 inhibitor effective to treat PACS1 Syndrome in a patient, or knocking down PACS1 or HDAC6 expression in the patient.

In another aspect or embodiment, a method of treating PACS2 Syndrome in a patient is provided. The method comprises administering to the patient an amount of a SIRT2 inhibitor effective to treat PACS2 Syndrome in a patient, or knocking down PACS2 or SIRT2 expression in the patient.

According to yet another aspect or embodiment of the invention, a method of restoring Golgi morphology in a cell having a mutation in a PACS2 gene, such as a PACS2 (Glu209Lys) (e.g., PACS2E$^{209K}$, SEQ ID NO: 7) mutation is provided. The method comprises administering to the patient an amount of a SIRT2 inhibitor effective to treat PACS2 Syndrome in a patient, or knocking down PACS2 or SIRT2 expression in the cell.

BRIEF DESCRIPTION OF THE DRAWINGS

(FIG. 8A) Control fibroblasts (Coriell #127160) and PACS1$^{R203W}$ fibroblasts (Coriell #127159) were treated with either a non-specific control siRNA or siRNAs specific for PACS1 or HDAC6. After 48 hrs, cells were fixed with 4% paraformaldehyde, stained for Giantin and then processed for confocal microscopy. (FIG. 8B). The number of dispersed Golgi mini stacks was quantified in at least 20 cells for each cell condition (Nikon Elements package). Data was analyzed using one-way Anova. Error bars represent SEM.

FIG. 10B, effects of tubacin, TSA, ACY-1215 and SW-100 on restoration of Golgi positioning. Data was analyzed using one-way Anova. Error bars represent SEM. n=48 cells from three independent experiments.

(FIG. 13A) Control (Coriell 127160) or PACS2$^{E209K}$ patient (Olson et al., 2018) dermal fibroblasts were treated with either a non-specific control siRNA or siRNAs specific for PACS2, SIRT2 or HDAC6. After 48 hrs, cells were fixed with 4% paraformaldehyde, stained for Giantin and then processed for confocal microscopy. (FIG. 13B). The number of dispersed Golgi mini stacks was quantified in at least 20 cells for each cell condition (Nikon Elements package). Data was analyzed using one-way Anova. Error bars represent SEM.

FIGS. 16A and 16B provide, continuous between figures, non-limiting examples of HDAC6 protein and mRNA sequences (SEQ ID NOS: 1 and 2, respectively).

FIG. 17 provides non-limiting examples of human SIRT2 protein and mRNA sequences (isoform 1) (SEQ ID NOS: 3 and 4, respectively).

FIGS. 18A and 18B provide, continuous between figures, non-limiting examples of PACS1 protein and mRNA sequences (SEQ ID NOS: 5 and 6, respectively), with R203 and 607C highlighted.

FIGS. 19A and 19B provide, continuous between figures, non-limiting examples of PACS2 protein and mRNA sequences (SEQ ID NOS: 7 and 8, respectively), with E209 and 625G highlighted.

DETAILED DESCRIPTION

Figure 1:
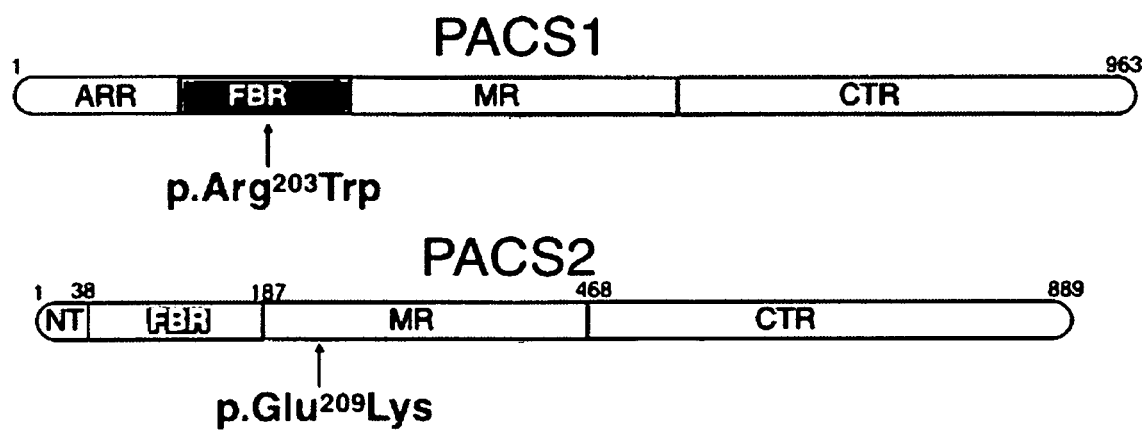
FIG. 1: Schematic of PACS1 and PACS2. ARR, atrophin 1-related region (PACS1 only); NT, N-terminal region (PACS2 only); FBR, cargo(furin) binding region; MR, middle region; CTR, C-terminal region. The Arg203Trp and Glu209Lys disease-causing mutations are located in the critical PACS1 FBR and PACS2 MR, respectively.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more. Patent publications cited below are hereby incorporated herein by reference in their entirety to the extent of their technical disclosure and consistency with the present specification.

As used herein, the terms "comprising," "comprise" or "comprised," and variations thereof, are open ended and do not exclude the presence of other elements not identified. In contrast, the term "consisting of" and variations thereof is intended to be closed and excludes additional elements in anything but trace amounts.

As used herein, the term "patient" or "subject" refers to members of the animal kingdom including but not limited to human beings and "mammal" refers to all mammals, including, but not limited to human beings.

As used herein, the "treatment" or "treating" of PACS1 Syndrome or PACS2 syndrome means administration to a patient by any suitable dosage regimen, procedure and/or administration route of a composition, device, or structure with the object of achieving a desirable clinical/medical end-point, including but not limited to, for PACS1 preventing, reducing, and/or eliminating any symptom of PACS1 Syndrome or PACS2 syndrome, such as, for PACS1 syndrome, developmental delay, intellectual disability, seizures, or characteristic craniofacial dysmorphisms, or, for PACS2 syndrome developmental delay, intellectual disability, seizures, characteristic craniofacial dysmorphisms liver damage, and/or cerebellar dysgenesis. An amount of any reagent or therapeutic agent, administered by any suitable route, effective to treat a patient is an amount capable of preventing, reducing, and/or eliminating any symptom of PACS1 Syndrome or PACS2 syndrome, such as developmental delay, intellectual disability, seizures, characteristic craniofacial dysmorphisms liver damage, and/or cerebellar dysgenesis as liver damage, and/or reducing or decreasing, for PACS1 syndrome, HDAC6 expression or activity, and for PACS2 syndrome, SIRT2 activity. The effective amount of each inhibitor may range from 1 pg per dose to 10 g per dose, including any amount there between, such as 1 ng, 1 µg, 1 mg, 10 mg, 100 mg, or 1 g per dose. The therapeutic agent may be administered by any effective route, and, for example, may be administered as a single bolus, at regular or irregular intervals, in amounts and intervals as dictated by any clinical parameter of a patient, or continuously.

The compositions described herein can be administered by any effective route, such as parenteral, e.g., intravenous, intramuscular, subcutaneous, intradermal, etc., formulations of which are described below and in the below-referenced publications, as well as is broadly-known to those of ordinary skill in the art.

Active ingredients, such as nucleic acids or analogs thereof, may be compounded or otherwise manufactured into a suitable composition for use, such as a pharmaceutical dosage form or drug product in which the compound is an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Useful dosage forms include: intravenous, intramuscular, or intraperitoneal solutions, oral tablets or liquids, topical ointments or creams and transdermal devices (e.g., patches). In one embodiment, the compound is a sterile solution comprising the active ingredient (drug, or compound), and a solvent, such as water, saline, lactated Ringer's solution, or phosphate-buffered saline (PBS). Additional excipients, such as polyethylene glycol, emulsifiers, salts and buffers may be included in the solution.

Suitable dosage forms may include single-dose, or multiple-dose vials or other containers, such as medical syringes, containing a composition comprising an active ingredient useful for treatment of PACS1 Syndrome or PACS2 syndrome as described herein.

Pharmaceutical formulations adapted for parenteral administration include aqueous and non-aqueous sterile injection solutions which may contain, for example and without limitation, anti-oxidants, buffers, bacteriostats, lipids, liposomes, emulsifiers, also suspending agents and rheology modifiers. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets.

Therapeutic compositions typically must be sterile and stable under the conditions of manufacture and storage. For example, sterile injectable solutions can be prepared by incorporating the active agent in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A "therapeutically effective amount" refers to an amount of a drug product or active agent effective, at dosages and for periods of time necessary, to achieve the desired therapeutic result. An "amount effective" for treatment of a condition is an amount of an active agent or dosage form, such as a single dose or multiple doses, effective to achieve a determinable end-point. The "amount effective" is preferably safe—at least to the extent the benefits of treatment outweighs the detriments, and/or the detriments are acceptable to one of ordinary skill and/or to an appropriate regulatory agency, such as the U.S. Food and Drug Administration. A therapeutically effective amount of an active agent may vary according to factors such as the disease state, age, sex, and weight of the individual, and the ability of the active agent to elicit a desired response in the individual. A "prophylactically effective amount" refers to an amount effective, at dosages and for periods of time necessary, to achieve a desired prophylactic result. Typically, since a prophylactic dose is used in subjects prior to or at an earlier stage of disease, the prophylactically effective amount may be less than the therapeutically effective amount.

Dosage regimens may be adjusted to provide the optimum desired response (e.g., a therapeutic or prophylactic response). For example, a single bolus may be administered, several divided doses may be administered over time, or the composition may be administered continuously or in a pulsed fashion with doses or partial doses being administered at regular intervals, for example, every 10, 15, 20, 30, 45, 60, 90, or 120 minutes, every 2 through 12 hours daily, or every other day, etc., be proportionally reduced or increased as indicated by the exigencies of the therapeutic situation. In some instances, it may be especially advantageous to formulate compositions, such as parenteral or inhaled compositions, in dosage unit form for ease of administration and uniformity of dosage. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

Provided herein is a method of treating PACS1 syndrome in a patient that comprises decreasing expression of PACS1 or HDAC6 or inhibits HDAC6 in a patient a patient, and in one example, in a patient's central nervous system, such as the brain and/or spinal cord. There are a number of ways to decrease expression or activity of PACS1 or HDAC6 in a patient, including, for example, and without limitation: RNA interference and antisense technology. HDAC6 can be inhibited through use of, for example, small molecules or reagents that interfere with HDAC6 activity, such as decoys, binding reagents, antagonists, etc. Treatment of a patient results in a decrease in one or more symptoms of PACS1 syndrome, such developmental delay, intellectual disability, seizures, and/or characteristic craniofacial dysmorphisms.

Provided herein is a method of treating PACS2 syndrome in a patient that comprises decreasing expression of PACS2 or SIRT2 or inhibiting activity of SIRT2 in a patient a patient, and in one example, in a patient's central nervous system, such as the brain and/or spinal cord. There are a number of ways to decrease expression or activity of PACS2 or SIRT2 in a patient, including, for example, and without limitation: RNA interference or antisense technology. SIRT2 may be inhibited through use of, for example, small molecules or reagents that interfere with SIRT2 activity, such as decoys, binding reagents, antagonists, etc. Treatment of a patient results in a decrease in one or more symptoms of PACS2 syndrome, such developmental delay, intellectual disability, seizures, characteristic craniofacial dysmorphisms liver damage, and/or cerebellar dysgenesis.

Also provided herein are methods of restoring Golgi morphology in a cell having a mutation in a PACS1 gene, such as PACS1 (Arg203Trp) mutation, or a mutation in a PACS2 gene, such as a PACS2 (Glu209Lys) mutation. The method of restoring Golgi morphology in a cell having a mutation in a PACS1 gene, such as PACS1 (Arg203Trp) mutation, comprising administering to the patient an amount of an HDAC6 inhibitor effective to treat PACS1 Syndrome in a patient, or knocking down PACS1 or HDAC6 expression in the patient. The method of restoring Golgi morphology in a cell having a mutation in a PACS2 gene, such as a PACS2 (Glu209Lys) mutation, comprises administering to the patient an amount of a SIRT2 inhibitor effective to treat PACS2 Syndrome in a patient, or knocking down PACS2 or SIRT2 expression in the cell. As described herein, Golgi morphology is disrupted by mutation of the PACS1 gene, such as a PACS1 (Arg203Trp) mutation, and by mutation of the PACS2 gene, such as a PACS2 (Glu209Lys) mutation. As indicated herein, among other effects, PACS1$^{R203W}$ and PACS2$^{E209K}$ dysregulate centrosome function, altering Golgi positioning, microtubule organization, and the integrity of the primary cilium. As such, restoring Golgi morphology includes restoring or correcting Golgi positioning, microtubule organization, and the integrity of the primary cilium.

A "selective inhibitor" of a protein, such as "a selective inhibitor of HDAC6" or "a selective inhibitor of SIRT2" specifically inhibits activity or expression of the specified protein as compared to other members of the same family of proteins, such as, for HDAC6, other HDAC proteins (e.g., HDAC1, HDAC2, HDAC3, HDAC4, HDAC5, HDAC7, HDAC8, HDAC9, HDAC10, or sirtuins), and for SIRT2, other HDAC proteins including sirtuins (e.g., SIRT1, SIRT3, SIRT4, SIRT5, SIRT7, or SIRT7). Specificity can be determined by any appropriate method. Specificity to a stated protein need not be complete, but is preferably significant so as to avoid affecting biochemical, cellular, or physiological processes other than the target processes of the mutant enzyme in the case of PACS1 or PACS2 syndromes.

By "target-specific" or reference to the ability of one compound to bind another target compound specifically, it is meant that the compound binds to the target compound to the exclusion of others in a given reaction system, e.g., in vitro, or in vivo, to acceptable tolerances, permitting a sufficiently specific diagnostic or therapeutic effect according to the standards of a person of skill in the art, a medical community, and/or a regulatory authority, such as the U.S. Food and Drug Agency (FDA), in aspects, in the context of targeting HDAC6, SIRT2, PACS1, or PACS2, and downregulating HDAC6, SIRT2, PACS1, or PACS2 activity, and effectively treating PACS1 syndrome or PACS2 syndrome, as described herein.

Histone deacetylase 6 (HDAC6) is a class II histone deacetylase (OMIM®-Online Mendelian Inheritance in Man® (OMIM) 300272; NCBI GeneID: 10013; GCID: GC0XP048801). Exemplary amino acid (Genbank Reference No. NP_001308154.1) and mRNA (Genbank Reference No. NM_001321225.2) sequences are provided in FIGS. 16A and 16B.

Sirtuin 2 (SIRT2) is an NAD-dependent deacetylase that mediates deacetylation of tubulin (OMIM 604480; NCBI GeneID: 22933; GCID:GC19M038878). During the cell cycle, SIRT2 regulates mitotic structures, including the centrosome, mitotic spindle, and midbody. Exemplary amino acid (Genbank Reference No. NP_036369.2) and mRNA (Genbank Reference No. NM_012237.4) sequences are provided in FIG. 17.

Phosphofurin acidic cluster sorting protein 1 (PACS1) is a trans-Golgi-membrane traffic regulator that directs protein cargo and several viral envelope proteins (OMIM 607492; NCBI GeneID: 55690; GCID:GC11P066088). It is upregulated during human embryonic brain development and has low expression after birth. Exemplary amino acid (Genbank Reference No. NP_060496.2) and mRNA (Genbank Reference No. NM_018026.4) sequences are provided in FIGS. 18A and 18B, with R203 and 607C highlighted. Additional sequences, including UniProt Reference Nos. Q6VY07-1 (isoform 1) and Q6VY07-2 (isoform 2), are broadly-known. Reagents useful for knocking down PACS1 expression may be determined using sequences different from those provided herein, for example Dharmacon siGENOME siRNA pool (M-006697-01-0020) targets targets mRNAs of four different GenBank Accession Nos. In aspects, where an RNAi reagent or antisense oligonucleotide overlaps with c.607C>T (PACS1$^{R203W}$), it includes the appropriate base substitution, A or T/U, at that position, depending on the strand.

The phosphofurin acidic cluster sorting protein 2 (PACS2) gene encodes a multifunctional sorting protein involved in nuclear gene expression and pathway traffic regulation (OMIM 610423; NCBI GeneID: 23241; GCID: GC14P105300). Exemplary amino acid (UniProt Reference No.: Q86VP3) and mRNA (Genbank Reference No. NM_001100913.3) sequences are provided in FIGS. 19A and 19B, with E209 and 625G highlighted. Additional sequences, including Genbank Reference No. NP_001094383.2, and UniProt Reference Nos. Q86VP3-2 (isoform 2), Q86VP3-3, and Q86VP3-4, NM_015197 (isoform 2), NM_001243127.3 (isoform 3), are broadly-known. Reagents useful for knocking down PACS2 expression may be determined using sequences different from those provided herein, for example Dharmacon siGENOME siRNA pool (M-022015-01-0020) targets mRNAs of 15 different GenBank Accession Nos. In aspects, where an RNAi reagent or antisense oligonucleotide overlaps with c.625G>A (PACS2$^{E209K}$), it includes the appropriate base substitution, A or T/U, at that position, depending on the strand.

Figure 14:
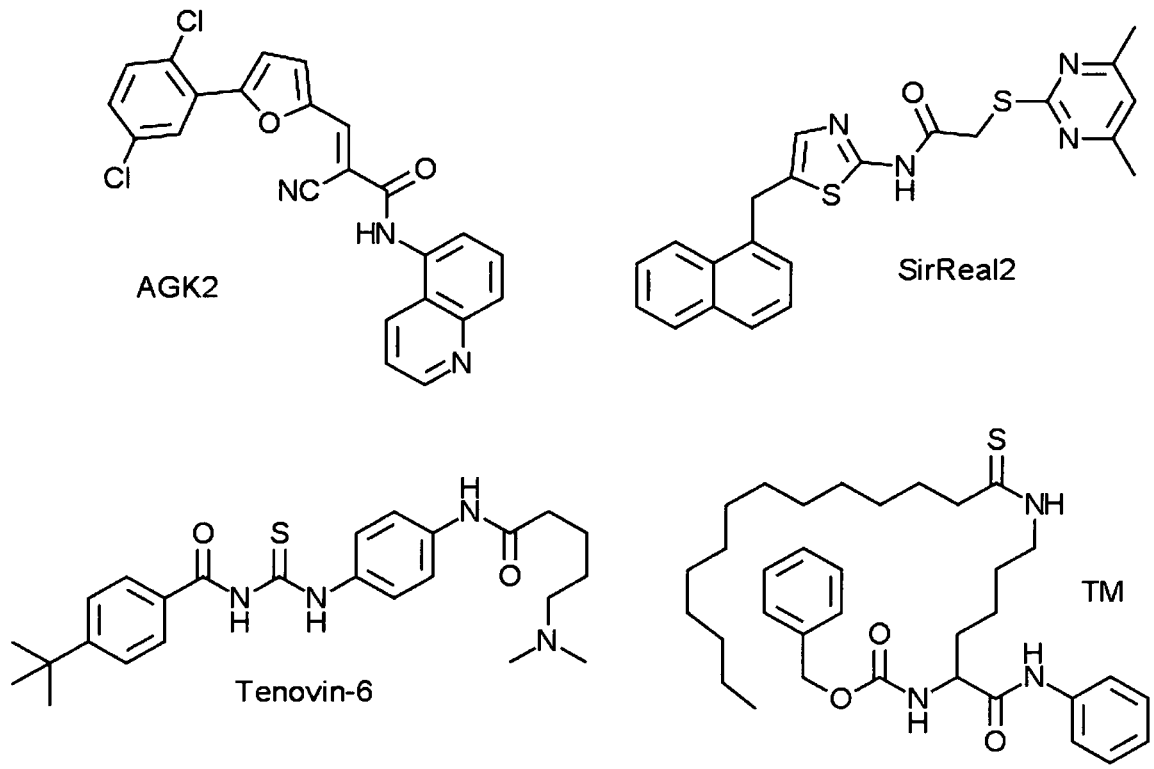
FIG. 14 provides structures for exemplary selective SIRT2 inhibitors.

Selective SIRT2 inhibitors are broadly-known, for example as disclosed in U.S. Pat. No. 9,572,789 B2, disclosing SIRT2 modulators including TM; International Patent Application Publication No. WO 2018/068357 A1; and United States Patent Application Publication No. 2008/0021063 A1, disclosing SIRT2 modulators including AGK2. Non-limiting examples of SIRT2 inhibitors are shown in FIG. 14, including: AGK2, SirReal2, Tenovin-6, and TM.

Figure 15:
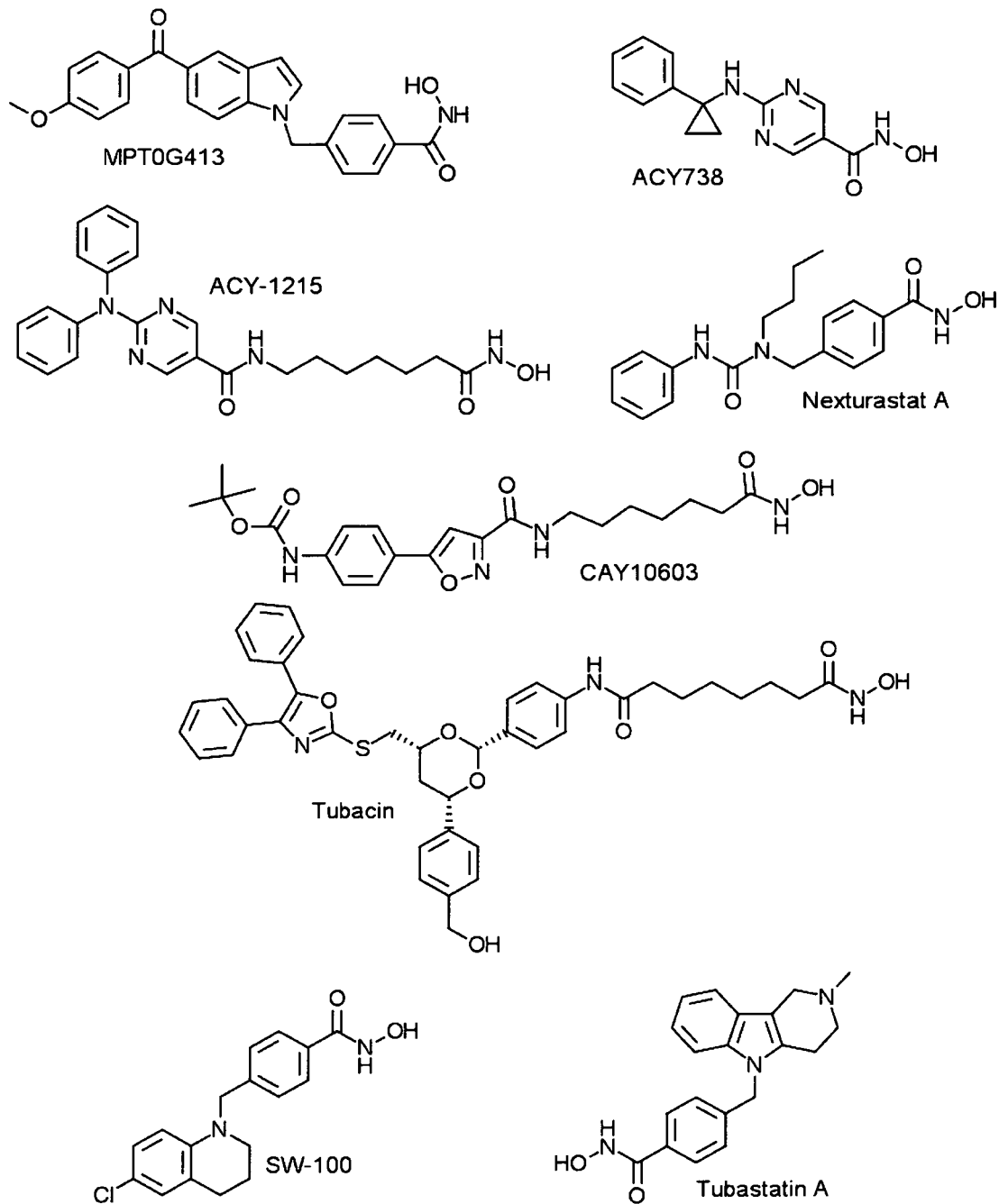
FIG. 15 provides structures for exemplary selective HDAC6 inhibitors and Tubastatin A.

Selective HDAC6 inhibitors are broadly-known, for example, as disclosed in United States Patent Publication No. 20070207950 A1, U.S. Pat. No. 8,901,156 B2 and 9,884,850 B2, and Wang, X. X., Wan, R. Z., and Liu, Z. P. (2018). Recent advances in the discovery of potent and selective HDAC6 inhibitors. Eur J Med Chem 143, 1406-1418. Non-limiting examples of selective HDAC6 inhibitors are shown in FIG. 15, including MPTOG413, Ricolinostat (ACY-1215), Nexturastat A, CAY10603, ACY-738, Tubacin, SW-100, and Tubastatin A.

As indicated above, amino acid and mRNA sequences for human HDAC6, human SIRT2, human PACS1, and human PACS2 are provided in FIGS. 16-19. For each gene, various mRNA and protein isoforms and polymorphisms may exist. As such, by HDAC6, SIRT2, PACS1, or PACS2, it is meant not only human HDAC6, SIRT2, PACS1, or PACS2, but HDAC6, SIRT2, PACS1, or PACS2 from any vertebrate or mammalian source, including, but not limited to, human, bovine, chicken, rodent, mouse, rat, porcine, ovine, primate, monkey, and guinea pig, unless specified otherwise. The term also refers to fragments, variants, alleles, and isoforms of native HDAC6, SIRT2, PACS1, or PACS2 that maintain at least one in vivo or in vitro activity of HDAC6, SIRT2, PACS1, and PACS2, respectively, in the context of the present disclosure, including, without limitation, the PACS1 variant c.607C>T (PACS1$^{R203W}$) and the PACS2 variant c.625G>A (PACS2$^{E209K}$), present in any transcript variant of PACS1 or PACS2, respectively. The term encompasses full-length unprocessed precursor forms of HDAC6, SIRT2, PACS1, or PACS2, as well as mature forms resulting from further processing, e.g., from post-translational processing. In one aspect, where an RNAi agent is used to knock down expression of an mRNA product of HDAC6, SIRT2, PACS1, or PACS2, the target portion of the sequence will be at least long enough to serve as a substrate for iRNA-directed cleavage at or near that portion of the nucleotide sequence of an mRNA molecule formed during the transcription of an HDAC6, SIRT2, PACS1, or PACS2 gene.

Mutations, sequence variants, polymorphisms, and alleles are identified in the context of the numbering of sequences provided herein, such as SEQ ID NOS: 1-8, with amino acid sequences being counted from base 1, and nucleotide sequences being counted from the first base of the start (ATG) codon. Reference to a sequence provided herein, such as PACS1$^{R203W}$, or c.607C>T, is to identify a specific base or amino acid, or a specific base or amino acid substitution, the numbering of which, in reference to any given sequence, may vary depending on the sequence numbering scheme for any particular sequence. For example, the numbering of bases in SEQ ID NO: 6 has c.607C>T at base 822, with the referenced base, 607C being counted from the start codon, beginning at base 216. As such, base 822 of SEQ ID NO: 6 is the same as PACS1 607C.

Expression of a gene refers to the conversion of a DNA sequence of a gene, e.g., the HDAC6, SIRT2, PACS1, or PACS2 gene, to an active, mature gene product such as a polypeptide/protein, or a functional nucleic acid, and includes, for example, transcription, post-transcriptional modification (e.g., splicing) translation, and post-translational processing and/or modification of a protein. Expression of a gene can be reduced by any effective mechanism at any stage of the gene expression process, such as by affecting transcriptional activation, transcription, post-transcriptional RNA processing, translation, and post-translational processing or modification. Activity of a gene product, such as HDAC6, SIRT2, PACS1, or PACS2, may be decreased not only by decreasing expression of the active protein product, but by affecting the mature protein product, or a downstream or upstream protein in a biological pathway affected by activity of, or affecting the activity of HDAC6, SIRT2, PACS1, or PACS2, such as a metabolic pathway, a signaling pathway, or a gene regulation pathway.

In aspects, antisense reagents also may be used to knock down HDAC6, SIRT2, PACS1, or PACS2 expression, to treat PACS1 or PACS2.

In aspects, RNA interference (RNAi) reagents, such as a siRNA, a shRNA, or a miRNA, as are broadly-known, may be used to knock down HDAC6, SIRT2, PACS1, or PACS2 expression. An exemplary siRNA oligomer for targeting HDAC6 is 5'-GCUGCACCGUGAGAGUUCCAACUUU-3' (SEQ ID NO: 9)(Gao, Y. et al., The Microtubule-associated Histone Deacetylase 6 (HDAC6) Regulates Epidermal Growth Factor Receptor (EGFR) Endocytic Trafficking and Degradation, J. Biol. Chem. 285:11219-11226). Additional useful RNAi reagents include, for example and without limitation, Dharmacon siGENOME siRNAs specific for PACS1 (M-006697-01-0020), HDAC6 (M-003499-00-0020), PACS2 (M-022015-01-0020), and SIRT2 (M-004826-02-0020).

A "gene" is a sequence of DNA or RNA which codes for a molecule, such as a protein or a functional RNA, such as a non-coding RNA that has a function. Complementary refers to the ability of polynucleotides (nucleic acids) to hybridize to one another, forming inter-strand base pairs. Base pairs are formed by hydrogen bonding between nucleotide units in antiparallel polynucleotide strands. Complementary polynucleotide strands can base pair (hybridize) in the Watson-Crick manner (e.g., A to T, A to U, C to G), or in any other manner that allows for the formation of duplexes. When using RNA as opposed to DNA, uracil rather than thymine is the base that is complementary to adenosine. Two sequences comprising complementary sequences can hybridize if they form duplexes under specified conditions, such as in water, saline (e.g., normal saline, or 0.9% w/v saline) or phosphate-buffered saline), or under other stringency conditions, such as, for example and without limitation, 0.1×SSC (saline sodium citrate) to 10×SSC, where 1×SSC is 0.15M NaCl and 0.015M sodium citrate in water. Hybridization of complementary sequences is dictated, e.g., by salt concentration and temperature, with the melting temperature (Tm) lowering with increased mismatches and increased stringency. Perfectly matched sequences are said to be fully complementary, or have 100% sequence identity (gaps are not counted and the measurement is in relation to the shorter of the two sequences). A sequence that specifically hybridizes to another typically has at least 80%, 85%, 90%, 95%, or 99% sequence identity with the other sequence.

Gene expression is the process by which information from a gene is used in the synthesis of a functional gene product, e.g., a protein or functional RNA. Gene expression involves various steps, including transcription, translation, and post-translational modification of a protein, as is broadly-known.

RNA levels in a cell, e.g., mRNA levels, can be controlled post-transcriptionally. Native mechanisms, including: endogenous gene silencing mechanisms, interference with translational mechanisms, interference with RNA splicing mechanisms, and destruction of duplexed RNA by RNAse H, or RNAse H-like activity. As is broadly-recognized by those of ordinary skill in the art, these endogenous mechanisms can be exploited to decrease or silence mRNA activity in a cell or organism in a sequence-specific, targeted manner. Antisense technology typically involves administration of a single-stranded antisense oligonucleotide (ASO) that is chemically-modified, e.g., as described herein, for bio-stability, and is administered in sufficient amounts to effectively penetrate the cell and bind in sufficient quantities to target mRNAs in cells. RNA interference (RNAi) harnesses an endogenous and catalytic gene silencing mechanism, which means that once, e.g., a microRNA, or double-stranded siRNA has been delivered into the cytosol, they are efficiently recognized and stably incorporated into the RNA-induced silencing complex (RiSC) to achieve prolonged gene silencing. Either antisense technology or RNAi may be used effectively to knock-down or silence expression of a gene or gene product, such as HDAC6, SIRT2, PACS1, or PACS2 (see, e.g., Watts, J. K., et al. Gene silencing by siRNAs and antisense oligonucleotides in the laboratory and the clinic (2012) 226(2):365-379). It should be noted that siRNAs and/or ASOs targeting HDAC6, SIRT2, PACS1, or PACS2 are commercially available from sources such as Dharmacon or Thermo Fisher Scientific, among many other sources, or are readily determined and synthesized based on broadly-known algorithms and calculators using an appropriate mRNA/cDNA sequence as input, such as, without limitation, SEQ ID NOS: 2, 4, 6, or 8, or the additional isoforms referenced herein. One siRNA, or multiple siRNAs targeting different portions of a target mRNA may be used.

The terms "IRNA," "RNAi agent," "RNAi agent," and "RNA interference agent" as used interchangeably herein, refer to an agent that contains RNA nucleotides, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., knocks down or silences, the expression of HDAC6, SIRT2, PACS1, or PACS2 RNA in a cell, e.g., a cell within a subject, such as a mammalian subject.

In one aspect, an RNAi agent includes a single stranded RNAi that interacts with a target RNA sequence, e.g., an HDAC6, SIRT2, PACS1, or PACS2 RNA sequence, to direct the cleavage of the target RNA. Without wishing to be bound by theory it is believed that long double stranded RNA introduced into cells is broken down into double stranded short interfering RNAs (siRNAs) comprising a sense strand and an antisense strand by a Type III endonuclease known as Dicer. Dicer, a ribonuclease-III-like enzyme, processes these dsRNA into 19-23 base pair short interfering RNAs with characteristic two base 3' overhangs. These siRNAs are then incorporated into an RNA-induced silencing complex (RISC) where one or more helicases unwind the siRNA duplex, enabling the complementary antisense strand to guide target recognition. Upon binding to the appropriate target mRNA, one or more endonucleases within the RISC cleave the target to induce silencing. Thus, in one aspect an RNAi is a single stranded RNA (ssRNA) (the antisense strand of an siRNA duplex) generated within a cell and which promotes the formation of a RISC complex to effect silencing of the target gene. Accordingly, the term "siRNA" is also used herein to refer to an interfering RNA (IRNA).

In another aspect, the RNAi agent may be a single-stranded RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded RNAs are described in U.S. Pat. No. 8,101,348 and in Lima et al., (2012) Cell 150:883-894.

In another aspect, an "IRNA" or RNAi agent" for use in the compositions and methods described herein is a double stranded RNA and can be referred to herein as a "double stranded RNAi agent," "double stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, e.g., an HDAC6, SIRT2, PACS1, or PACS2 RNA. In some aspects, a double stranded RNA (dsRNA) triggers the degradation of a target RNA, e.g., an mRNA, through a post-transcriptional gene-silencing mechanism referred to herein as RNA interference or RNAi.

The majority of nucleotides of each strand of a dsRNA molecule may be ribonucleotides, but as described in detail herein, each or both strands can also include nucleotide analogs, where one or more non-ribonucleotides, e.g., a deoxyribonucleotide and/or a modified nucleotide. In addition, as used in this specification, an "RNAi agent" or "RNAi agent" may include ribonucleotides with chemical modifications; an RNAi agent may include substantial modifications at multiple nucleotides. As used herein, the term "modified nucleotide" refers to a nucleotide having, independently, a modified sugar moiety, a modified inter-nucleotide linkage, and/or modified nucleobase. Thus, the term modified nucleotide encompasses substitutions, additions or removal of, e.g., a functional group or atom, to inter-nucleoside linkages, sugar moieties, or nucleobases. The modifications suitable for use in the agents described herein include all types of modifications disclosed herein or known in the art. Any such modifications, as used in a siRNA type molecule, are encompassed by "RNAi agent" or "RNAi reagent" for the purposes of this disclosure.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some aspects, the hairpin loop can comprise at least 2, at least 3, at least 4, at least 5, at least 6, at least 7, at least 8, at least 9, at least 10, at least 20, at least 23, or more unpaired nucleotides. In some aspects, the hairpin loop can be 10 or fewer nucleotides. In some aspects, the hairpin loop can be 8 or fewer unpaired nucleotides. In some aspects, the hairpin loop can be 4-10 unpaired nucleotides. In some aspects, the hairpin loop can be 4-8 nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In one aspect, an RNAi agent is a dsRNA, each strand of which comprises 19-23 nucleotides, that interacts with a target RNA sequence, e.g., an HDAC6, SIRT2, PACS1, or PACS2 RNA, without wishing to be bound by theory, long double stranded RNA introduced into cells is broken down into siRNA by a Type III endonuclease known as Dicer. Dicer, a ribonuclease-Ill-like enzyme, processes the dsRNA into 19-23 base pair short interfering RNAs with characteristic two base 3' overhangs. The siRNAs are then incorporated into an RNA-induced silencing complex (RISC) where one or more helicases unwind the siRNA duplex, enabling the complementary antisense strand to guide target recognition. Upon binding to the appropriate target RNA, one or more endonucleases within the RISC cleave the target to induce silencing. In one aspect, an RNAi agent is a dsRNA of 24-30 nucleotides that interacts with a target RNA sequence, e.g., an HDAC6, SIRT2, PACS1, or PACS2 RNA sequence, to direct the cleavage of the target RNA.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary," and "substantially complementary" herein can be used with respect to the base matching between the sense strand and the antisense strand of a dsRNA, or between the antisense strand of an RNAi agent and a target sequence, as will be understood from the context of their use.

As used herein, a polynucleotide that is "substantially complementary to at least part of a messenger RNA (mRNA)" refers to a polynucleotide that is substantially complementary to a contiguous portion of the mRNA of interest (e.g., an HDAC6, SIRT2, PACS1, or PACS2 RNA).

Accordingly, in some aspects, the antisense strand polynucleotides disclosed herein are fully complementary to the target HDAC6, SIRT2, PACS1, or PACS2 RNA sequence. In other aspects, the antisense strand polynucleotides disclosed herein are substantially complementary to the target HDAC6, SIRT2, PACS1, or PACS2 RNA sequence and comprise a contiguous nucleotide sequence which has at least about 80% sequence identity to the nucleotide sequence of any of SEQ ID NOS: 2, 4, 6, or 8 (FIGS. 16A, 16B, 17, 18A, 18B, 19A, and 19B), or a fragment thereof, such as about 85%, about 86%, about 87%, about 88%, about 89%, about 90%, about 91%, about 92%, about 93%, about 94%, about 95%, about 96%, about 97%, about 98%, or about 99% complementary.

It is understood that the sequence of the HDAC6, SIRT2, PACS1, or PACS2 RNA must be sufficiently complementary to the antisense strand of the RNAi agent for the agent to be used in the indicated patient, e.g. human, mammalian, or vertebrate species.

The term "inhibiting," as used herein, is used interchangeably with "reducing," "silencing," "downregulating," "suppressing," "knocking down," and other similar terms, and includes any level of inhibition.

The phrase "knocking down or silencing of HDAC6, SIRT2, PACS1, or PACS2 RNA," as used herein, includes inhibition of expression of any HDAC6, SIRT2, PACS1, or PACS2 gene (such as, e.g., a mouse HDAC6, SIRT2, PACS1, or PACS2 gene, a rat HDAC6, SIRT2, PACS1, or PACS2 gene, a monkey HDAC6, SIRT2, PACS1, or PACS2 gene, or a human HDAC6, SIRT2, PACS1, or PACS2 gene) as well as variants or mutants of an HDAC6, SIRT2, PACS1, or PACS2 gene, in its production of HDAC6, SIRT2, PACS1, or PACS2 RNA, affecting the stability of HDAC6, SIRT2, PACS1, or PACS2 RNA, such as by antisense or RNAi technologies. "Knocking down or silencing of HDAC6, SIRT2, PACS1, or PACS2 RNA" includes any level of inhibition of an HDAC6, SIRT2, PACS1, or PACS2 RNA, e.g., at least partial suppression of the expression of an HDAC6, SIRT2, PACS1, or PACS2 RNA, such as an inhibition by at least about 20%. In certain aspects, inhibition is by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of an HDAC6, SIRT2, PACS1, or PACS2 RNA may be assessed based on the level of any variable associated with HDAC6, SIRT2, PACS1, or PACS2 RNA expression, e.g., HDAC6, SIRT2, PACS1, or PACS2 RNA level. The expression of an HDAC6, SIRT2, PACS1, or PACS2 RNA may also be assessed indirectly based on assay of physiological markers associated with decreased expression of the HDAC6, SIRT2, PACS1, or PACS2 RNA in a patient.

In one aspect, at least partial suppression of the expression of an HDAC6, SIRT2, PACS1, or PACS2 RNA, is assessed by a reduction of the amount of HDAC6, SIRT2, PACS1, or PACS2 RNA that can be isolated from or detected in a cell or group of cells, e.g., in a neuronal cell. As such, in aspects, HDAC6, SIRT2, PACS1, or PACS2 levels may be determined from a biopsy, or from a normal tissue sample obtained from a patient, for example, from a blood draw (see, e.g., Dan T. Vogl, et al. Ricolinostat, the First Selective Histone Deacetylase 6 Inhibitor, in Combination with Bortezomib and Dexamethasone for Relapsed or Refractory Multiple Myeloma, *Clin Cancer Res* Jul. 1 2017 (23) (13) 3307-3315). A reduction of the amount of HDAC6, SIRT2, PACS1, or PACS2 RNA in a cell or tissue in which an HDAC6, SIRT2, PACS1, or PACS2 gene is transcribed and which has been treated such that the expression of an HDAC6, SIRT2, PACS1, or PACS2 RNA is inhibited, may be determined as compared to a second cell or tissue substantially identical to the first cell or tissue but which has not been so treated (control cells), e.g., obtained and cultured from a biopsy. The degree of inhibition may be expressed in terms of:

$$\frac{(mRNA \text{ in control cells}) - (mRNA \text{ in treated cells})}{(mRNA \text{ in control cells})} \times 100\%)$$

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell. Further, an shRNA RNAi agent can be produced from a gene for expressing an shRNA, transferred by any suitable means, such as by recombinant vector such as a recombinant Adeno-associated virus (AAV) or retrovirus vector, or by gene editing, such as by CRISPR-Cas or TALENS methods, as are broadly-known. These technologies are broadly-known by those of ordinary skill and resources, such as suitable vectors and production systems are broadly-available, including from commercial sources.

Contacting a cell in vitro may be done, for example, by incubating the cell with the RNAi agent. Contacting a cell in vivo may be done, for example, by injecting the RNAi agent into or near the tissue where the cell is located, such as a tumor, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, which directs the RNAi agent to a site of interest, e.g., the liver. Combinations of in vitro and in vivo methods of contacting are also possible. For example, a cell may also be contacted in vitro with an RNAi agent and subsequently transplanted into a subject.

In one aspect, contacting a cell with an iRNA includes "introducing" or "delivering the iRNA into the cell" by facilitating or effecting uptake or absorption into the cell. Absorption or uptake of an iRNA can occur through unaided diffusive or active cellular processes, or by use of auxiliary agents or devices. Introducing an iRNA into a cell may be in vitro and/or in vivo. For example, for in vivo introduction, iRNA can be injected into a tissue site or administered systemically. In vitro introduction into a cell includes methods known in the art such as electroporation and lipofection. Further approaches are known in the art.

As used herein, and further to the discussion above regarding iRNA reagents, "agent" or "RNAi agent," when used in the context of an antisense, RNAi, or ribozyme, or other single-stranded or double-stranded RNA interfering nucleic acids, refers not only to RNA structures, but effective nucleic acid analog structures. In antisense and RNAi technologies, use of RNA poses significant delivery issues due to the lability of RNA molecules. As such, RNA is commonly chemically-modified to produce nucleic acid analogs, not only to enhance stability of the nucleic acid molecules, but often resulting in increased binding affinity, and with reduced toxicity. Such modifications are broadly-known to those of ordinary skill in the art, and are available commercially (see, e.g., Corey, D. R., Chemical modification: the key to clinical application of RNA interference? (2007) J Clin Invest. 117(12):3615-3622, also describing RNAi, and United States Patent Application Publication No. 2017/0081667, incorporated herein by reference for its technical disclosure). Non-limiting examples of modifications to the nucleic acid structure in nucleic acid analogs include: modifications to the phosphate linkage, such as phosphoramidates or phosphorothioates; sugar modification, such as 2'-O, 4'-C methylene bridged, locked nucleic acid (LNA), 2'-methoxy, 2'-O-methoxyethyl (MOE), 2'-fluoro, S-constrained-ethyl (cEt), and tricyclo-DNA (tc-DNA); and non-ribose structures, such as phosphorodiamidate morpholino (PMO) and peptide-nucleic acids (PNA).

In addition to those HDAC6-, SIRT2-, PACS1-, or PACS2-active RNAi agents described herein, antisense agents (ASOs), other RNAi agents, ribozyme agents, and other nucleic acid-based methods of reducing gene expression, can be designed and tested based on known sequences of HDAC6, SIRT2, PACS1, or PACS2 RNAs and gene structure (exemplary sequences are provided herein). Based on the present disclosure, one of ordinary skill can design, and/or produce an active agent capable of knocking down HDAC6, SIRT2, PACS1, or PACS2 expression. Of note, a number of publications describe algorithms for generating candidate iRNA sequences, and publicly-available software can be used to implement those algorithms. As such, typically, one only needs to enter an mRNA sequence into a calculator to produce candidate iRNAs.

As above, RNAi reagents, such as an siRNA, may have 100% sequence identity with a portion or fragment of any one or more of SEQ ID NOS: 2, 4, 6, or 8, or a sequence complementary thereto, or may include one or more additional nucleobases at their 3' or 5' end, or may include one or more substitutions that do not substantially interfere with the activity of the RNAi agent in knocking down or silencing HDAC6, SIRT2, PACS1, or PACS2 expression. Also, SEQ ID NOS: 2, 4, 6, or 8 are exemplary mRNAs of isoforms of HDAC6, SIRT2, PACS1, or PACS2. Alleles, mutations, or other variants or polymorphisms (e.g., single-nucleotide polymorphisms, SNPs) of HDAC6, SIRT2, PACS1, or PACS2 sequences are possible, and as such effective agents, such as RNAi and antisense agents may be substituted to accommodate those variants. Further, some sequence mismatches in RNAi agents are not only tolerated, but may be beneficial (see, e.g., Wu, H., et al. "Improved siRNA/shRNA Functionality by Mismatched Duplex" PLOS One. 2011; 6(12): e28580). As such, sequences having up to 90% or 95% (two or one mismatches, respectively) sequence identity with SEQ ID NOS: 4-8 are expected, in many circumstances, to be effective RNAi agents.

In aspects, a useful antisense oligonucleotide, e.g., a nucleic acid or nucleic acid analog, comprises a sequence having at least 90% sequence identity, at least 95% sequence identity, or 100% sequence identity with one of SEQ ID NOs: 2, 4, 6, or 8. In aspects, the antisense oligonucleotide is an LNA.

Example 1—PACS1

Figure 2:
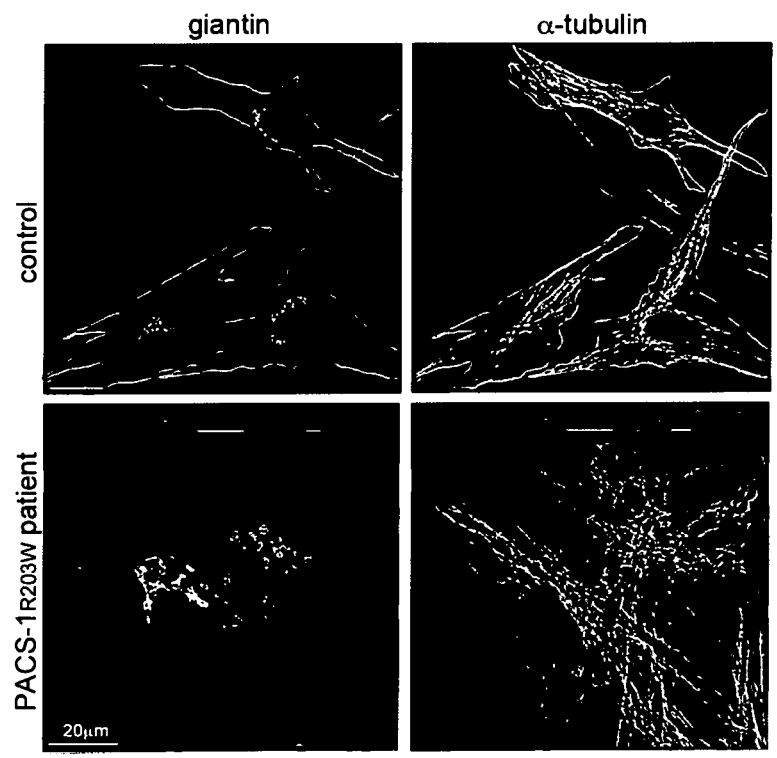
FIG. 2: The Golgi is dispersed in PACS1$^{R203W}$ patient fibroblasts. Control fibroblasts (Coriell #127160) and PACS1$^{R203W}$ fibroblasts (Coriell #127159) were analyzed by confocal microscopy. Giantin (left) and α-tubulin (right) are shown. Similar results were observed using a second patient line (Coriell #127161). Images are representative of 8 independent experiments.

To determine how the R203W mutation affects PACS1 functions, we obtained one control (parent) and two PACS1$^{R203W}$ patient-derived fibroblast lines (Coriell Institute, https://www.coriell.org). Our initial confocal analysis showed marked differences in Golgi positioning between control fibroblasts and the PACS1$^{R203W}$ cell lines (FIG. 2). In control fibroblasts, the Golgi ribbon characteristically concentrated in the paranuclear region. By contrast, in either patient cell line, the Golgi ribbon fragmented into ministacks, which dispersed throughout the cytoplasm.

We next asked how PACS1$^{R203W}$ might cause the Golgi to fragment and disperse. Golgi positioning is critically dependent on the dynein-dependent centripetal movement of Golgi stacks along microtubules towards the paranuclear centrosome, which functions as the principal microtubule organizing center (MTOC) (Yadav, S., and Linstedt, A. D. (2011). Golgi positioning. Cold Spring Harb Perspect Biol 3). We analyzed the microtubule staining patterns in the control and PACS1$^{R203W}$ fibroblasts (FIG. 2). Overlay of the Golgi and microtubule staining patterns in control fibroblasts showed that the Golgi ribbon concentrated at base of the microtubule network, which emanated from a single centrosome that was juxtaposed to the nucleus. By contrast, the staining pattern overlay in the PACS1$^{R203W}$ cells was strikingly different. The microtubules formed a complex network that appeared to emanate from multiple MTOCs. Indeed, the seemingly dispersed Golgi ministacks appeared to coalesce towards one or the other MTOC.

In FIG. 2: Control (Coriell 127160) and PACS1$^{R203W}$ patient (Coriell 127159) dermal fibroblasts grown on glass coverslips were fixed with 4% paraformaldehyde, permeabilized with 0.1% TX-100 and stained with antibodies that detect the Golgi marker Giantin (provided by A. Linstedt, CMU) and α-tubulin (Sigma 3878S) and then visualized with appropriate secondary antibodies (Thermo Fisher A11036 (giantin) and Thermo Fisher A1101 (α-tubulin). Images were captured on a Nikon A1R laser scanning confocal microscope.

Figure 3:
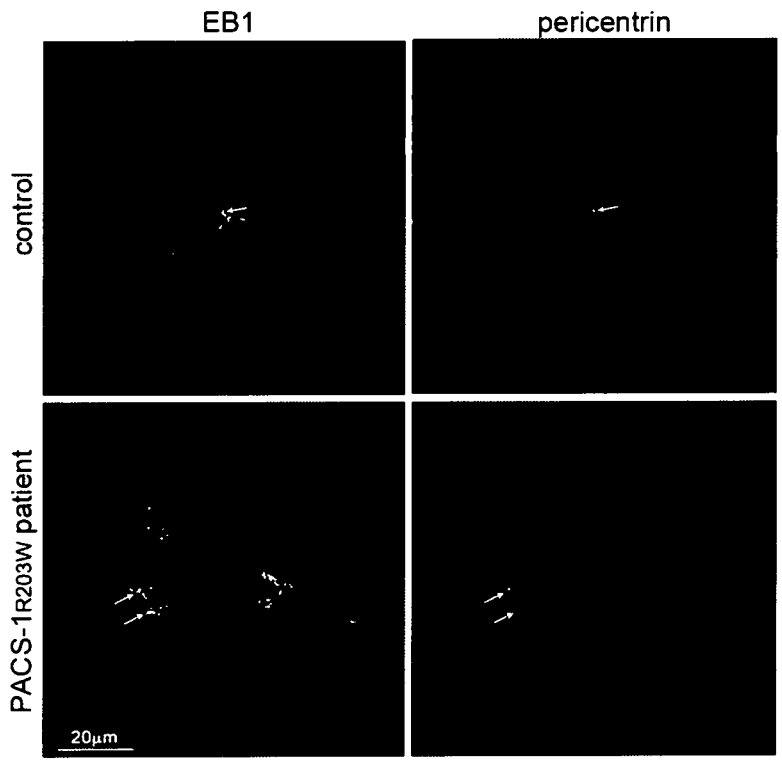
FIG. 3: PACS1$^{R203W}$ fibroblasts contain multiple MTOCs. Control fibroblasts (Coriell #127160) and PACS1$^{R203W}$ fibroblasts (Coriell #127159) were treated with 5 μM nocodazole for 10 hr. The nocodazole was washed out and the cells were fixed 3 min later. The microtubule associated protein EB1 (left) and the centrosome marker, pericentrin (right) are shown. Pericentrin-negative asters stained positively for giantin (data not shown). Images are representative of 3 independent experiments. Arrows, asters.

In many cell types the centrosome serves as the primary MTOC. However, under certain conditions, the Golgi and other structures function as alternative MTOCs. To test the possibility that PACS1$^{R203W}$ fibroblasts possess multiple MTOCs, we conducted a microtubule aster assay (FIG. 3). PACS1$^{R203W}$ and control fibroblasts were pre-treated with nocodazole to depolymerize microtubules. Following nocodazole washout, the cells were incubated in fresh media for 3 min to stimulate formation of microtubule asters, which were detected with an antibody against the microtubule plus-end tracking protein, EB1, and co-stained with antibodies against either the centrosome (pericentrin) or Golgi (giantin). Control fibroblasts contained a single paranuclear aster nucleated by the pericentrin-containing centrosome. By contrast, PACS1$^{R203W}$ cells frequently contained multiple asters, many of which were located in the cell periphery. While some asters where nucleated by centrosomes (pericentrin), other asters appeared be nucleated by Golgi (giantin) elements (FIG. 3 and data not shown). Together, these findings suggest that PACS1$^{R203W}$ disturbs centrosomal functions, including its role as the primary MTOC.

In FIG. 3: Control (Coriell 127160) and PACS1$^{R203W}$ patient (Coriell 127159) dermal fibroblasts were treated with 5 µM nocodazole for 10 hours. The nocodazole was washed out and the cells were fixed 3 min later. Cells were fixed and stained with antibodies to detect the microtubule associated protein EB1 (left, Fisher #610534) and and the centrosome marker, pericentrin (right, Abcam #4488). The cells were then processed for confocal microscopy as described for FIG. 2.

Figure 4:
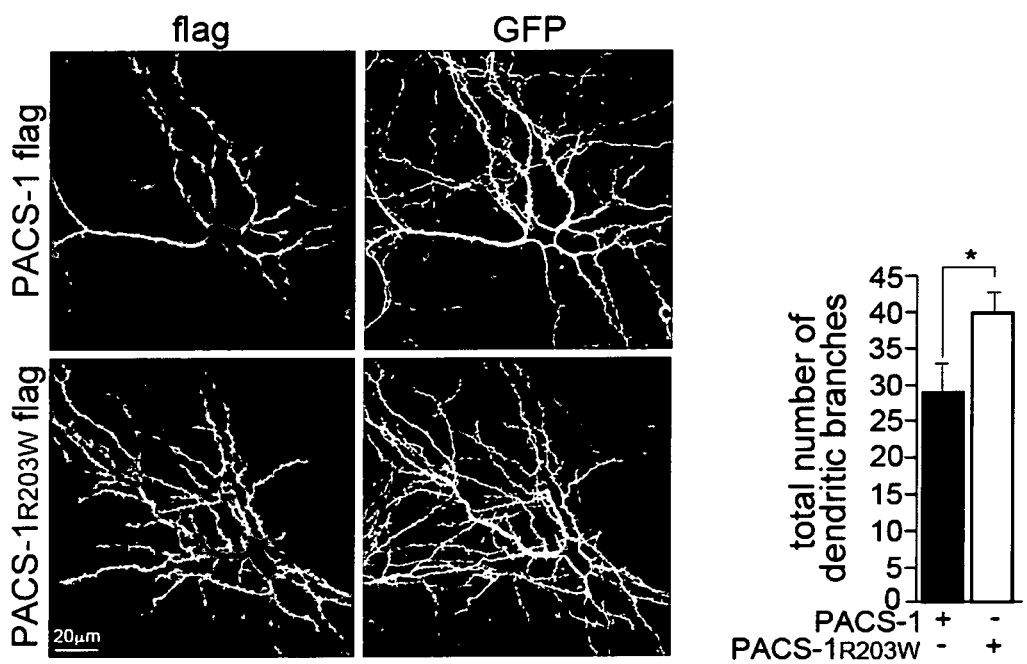
FIG. 4: PACS1$^{R203W}$ increases dendritic branching. Rat hippocampal neurons were co-transfected with plasmids expressing Flag-tagged PACS1 or PACS1$^{R203W}$ (left) and GFP (right). After 10 days, neurons were fixed, images captured, and dendritic length and branching measured using the simple neurite tracer plugin and Image J, and then quantified.

We then asked whether PACS1$^{R203W}$ might increase dendrite arborization in transfected primary rat hippocampal neurons. Morphometric analysis of the transfected cells revealed that neurons expressing PACS1$^{R203W}$ underwent increased dendritic branching and arborization (FIG. 4). This finding was consistent with our determination that PACS1$^{R203W}$ repositions Golgi elements that can form secondary MTOCs to increase dendritic branching. The dysregulated dendritic branching that is observed in several neurodevelopmental disorders further reinforces the potential importance of this finding (Kaufmann, W. E., and Moser, H. W. (2000). Dendritic anomalies in disorders associated with mental retardation. Cereb Cortex 10, 981-991).

In FIG. 4: Hippocampal neurons were dissected from Long-Evans rats. Dissociated hippocampal neurons were plated on acid washed 12 mm coverslips coated overnight with poly-D-lysine (HMW 20 μg/ml) and Laminin (3.4 μg/ml). Neurons were cultured in Neurobasal media (Invitrogen) supplemented with 2% B27 (Invitrogen), penicillin (100 U/ml) and streptomycin (100 mg/ml), and 2 mM glutamine. DNA transfections was done using the Lipofection method (Invitrogen: Lipofectamine 2000). Neurons were transfected with a total of 1 μg/well of DNA, including CMV-vGFP and flag-tagged PACS-1 or flag-tagged PACS-1 R203W. After 10 days in culture, neurons were fixed for 8 minutes at room temperature with a paraformaldehyde 4%, sucrose 4% solution (in PBS, pH 7.4), washed and incubated with the indicated antibodies overnight at 4C, and stained with secondary antibodies at room temperature for 2 hours. Antibodies were diluted in GDB buffer (0.1% gelatin; 0.3% TX-100; 15 mM phosphate buffer (pH 7.4); 250 mM NaCl). Rabbit polyclonal anti-FLAG (1:200, Sigma F7425), and mouse monoclonal anti-PSD95 (1:200, Thermo Fisher) were used. Alexa 555 and 647 (1:400) secondary antibodies were used to visualize primary antibodies. Coverslips were mounted on glass slides with Fluormount G (South Biotech) and imaged using a Nikon A1R laser scanning confocal microscope. For morphometric analysis, total number of dendritic branches was measured manually using Fiji (Image J). A maximum intensity projection from a z-stack acquisition was imported and manually traced using the Simple Neurite Tracer plugin, total number of dendritic branches was then computed. Total number of dendritic branches (or expressed as relative percentage to control condition) was taken as a representative parameter of dendritic complexity and neuronal arborization. For each experimental condition, at least 10 neurons from two different coverslips were analyzed.

Figure 5:
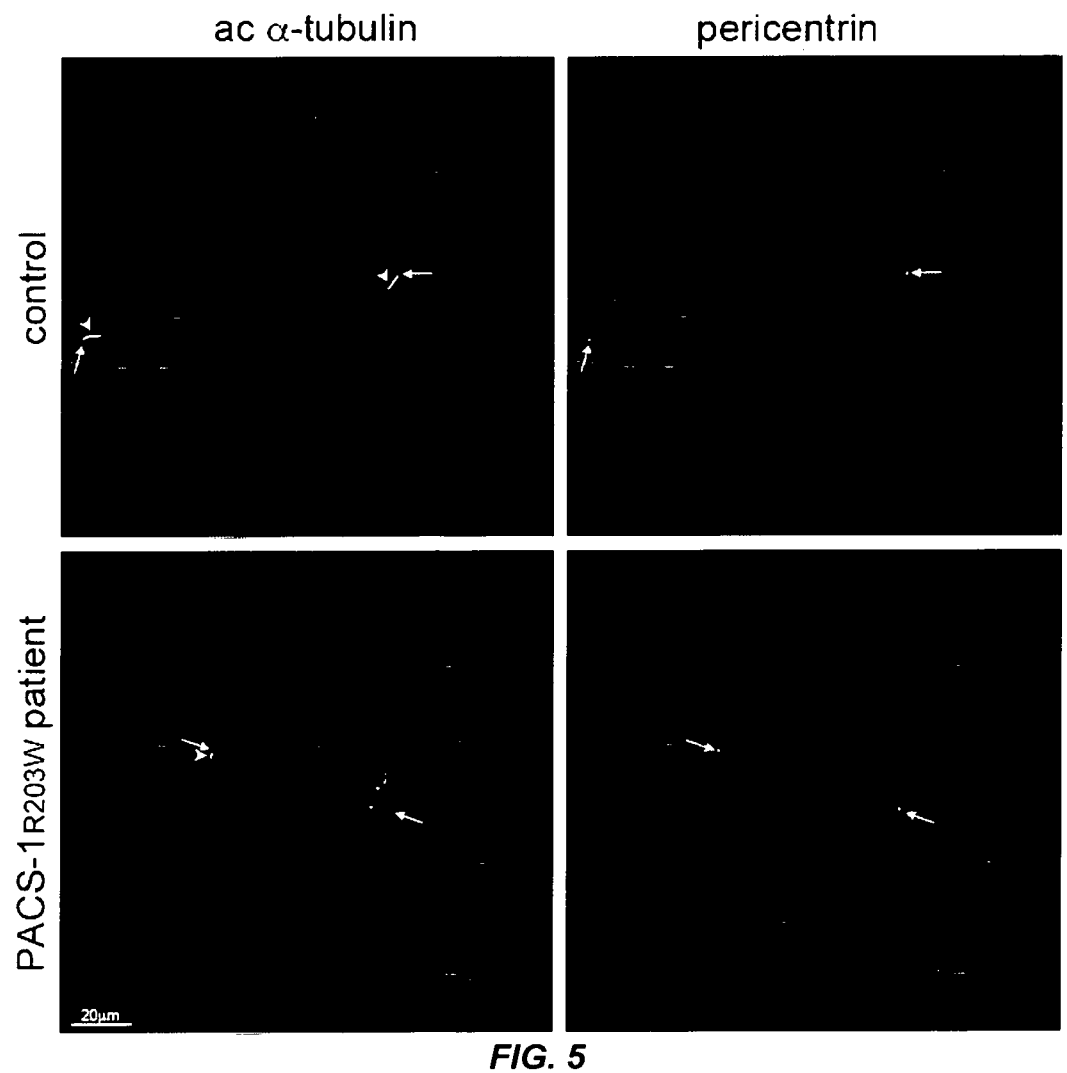
FIG. 5: PACS1$^{R203W}$ fibroblasts have blunted cilia. Control fibroblasts (Coriell #127160) and PACS1$^{R203W}$ fibroblasts (Coriell #127159) were serum starved overnight, fixed and processed for confocal microscopy. Acetylated α-tubulin (left), pericentrin (right). Images are representative of 3 independent experiments. Arrowheads, Ac(Lys$^{40}$)-α-tubulin; Arrows, pericentrin.

We then asked whether PACS1$^{R203W}$ affected expression of the primary cilium in patient fibroblasts. Following serum starvation, control fibroblasts contained a single primary cilium enriched with acetylated α-tubulin along the length of the axoneme and with pericentrin located at the base (FIG. 5). By contrast, the primary cilia in PACS1$^{R203W}$ fibroblasts were shorter, and, in some cells, absent. These findings raise the possibility that PACS1$^{R203W}$ may disturb cilia-dependent signaling pathways similar to those described for other neurodevelopmental disorders (Valente, E. M., Rosti, R. O., Gibbs, E., and Gleeson, J. G. (2014). Primary cilia in neurodevelopmental disorders. Nat Rev Neurol 10, 27-36).

In FIG. 5: Control (Coriell 127160) and PACS1$^{R203W}$ patient (Coriell 127159) dermal fibroblasts grown on glass coverslips were starved overnight to induce cell cycle arrest and cilia formation. The starved cells were fixed with 4% paraformaldehyde, permeabilized with 0.1% TX-100 and stained with antibodies that detect the acetylated (Lys$^{40}$) α-tubulin (Sigma T6793) and pericentrin (Abcam #4488).

Cells were visualized with appropriate secondary antibodies (Thermo Fisher A11036 (acetylated α-tubulin) and Thermo Fisher A11036 pericentrin)). Images were captured on a Nikon A1R laser scanning confocal microscope.

Our results suggest that the R203W mutation alters the interaction between PACS1 and one or more client proteins to dysregulate centrosomal/ciliary functions. Since the level of tubulin acetylation markedly affects cellular attributes, including Golgi positioning, dissolution of the ciliary axoneme and dendritic branching, we measured the extent of α-tubulin acetylation in PACS1$^{R203W}$ fibroblasts. Western blot analysis showed that the level of Ac(Lys$^{40}$)-α-tubulin was reduced in PACS1$^{R203W}$ fibroblasts compared to control fibroblasts (FIG. 6).

Figure 6:
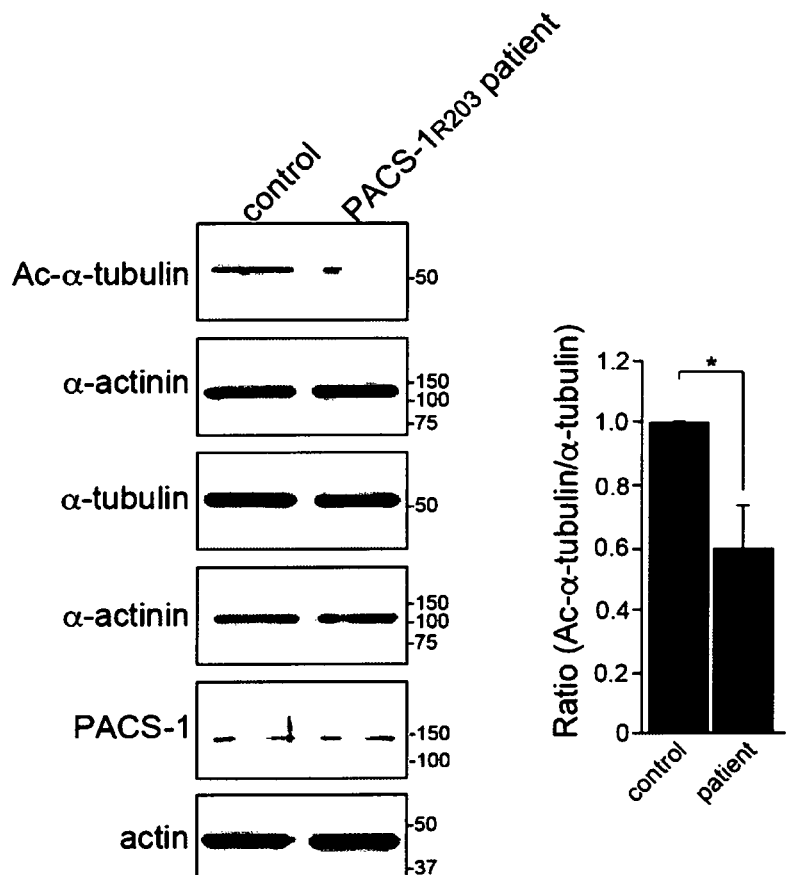
FIG. 6: α-tubulin is hypoacetylated in PACS1$^{R203W}$ patient cells. Lysates from control fibroblasts (Coriell #127160) or PACS1$^{R203W}$ fibroblasts (Coriell #127159) were analyzed for the indicated proteins by western blot. The amount of acetylated α-tubulin and total tubulin in each sample was normalized to total α-actinin (graph).

In FIG. 6: Parallel plates of Control (Coriell 127160) and PACS1$^{R203W}$ patient (Coriell 127159) dermal fibroblasts grown to near confluency were lysed in mRIPA (50 mM Tris pH 8.0, 150 mM NaCl, 1% NP-40, 1% sodium deoxycholate, 1 mM EDTA and protease inhibitors (0.5 mM PMSF, 0.1 μM each of aprotinin, pepstatin A and leupeptin). Cell lysates were separated on a 10% SDS polyacrylamide gel and analyzed by western blot using the following primary antibodies; α-tubulin (CST 3873S), Ac(Lys$^{40}$)-α-tubulin (CST 5334S), PACS-1 11703 ((Scott et al., 2006)), actin (Millipore MAB1501) and α-actinin (CST 3134S) followed by HRP-coupled secondary antibodies (goat anti-rabbit (Fisher OB4050-05) or goat anti-mouse (Fisher OB1010-05)). Western blots were developed with Pierce ECL Western Blotting Substrate (ThermoFisher), using the Protein Simple FluorChem E image acquisition system and signals were quantified using the AlphaView image analysis software package (ProteinSimple).

Figure 7:
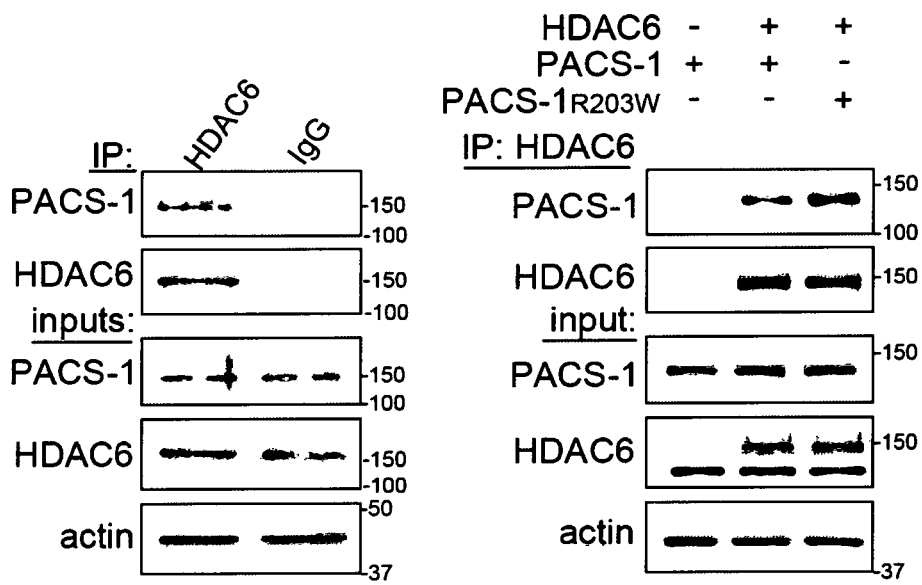
FIG. 7: HDAC6 preferentially interacts with PACS1 R203W. (Left): Endogenous HDAC6 was immunoprecipitated from control fibroblasts and co-precipitating PACS1 was detected by western blot. (Right): Plasmids expressing the indicated proteins were expressed in HCT116 cells. Flag proteins were immunoprecipitated and interacting HA proteins identified by western blot. Representative of 5 independent experiments.

We then asked whether endogenous PACS1 interacts with HDAC6. A co-immunoprecipitation assay revealed they interact (FIG. 7). In co-expression studies, we further determined that HDAC6 interacted to a greater extent with PACS1$^{R203W}$ than PACS1.

In FIG. 7: Left-Coriell 127160 dermal fibroblasts were lysed in AG buffer 50 mM Tris pH 7.9, 150 mM NaCl, 1% NP-40, 1 mM EDTA and 10% glycerol. The lysate was then incubated with anti-HDAC6 (CST 7558) or normal IgG control (CST 2729) overnight at 4° C. Antibodies were captured with protein A agarose and washed 3×in AG buffer. Bound proteins were eluted with SDS SB and analyzed by western blot as described in the methods for FIG. 6 using the following antibodies; HDAC6 (CST 7558), PACS-1 11703 (Scott et al., 2006) and actin (Millipore MAB1501). Right-Replicate plates of HCT116 cells were transfected with plasmids expressing Flag-tagged HDAC6, HA-tagged PACS1, HA-tagged PACS1$^{R203W}$ or pcDNA3 empty vector (to normalize the amount of input plasmid) using Lipofectamine 2000. After 24 hr, cells were lysed in GB buffer (50 mM Tris pH 7.4, 150 mM NaCl, 1% NP-40, 10% glycerol plus protease inhibitors). Flag-tagged HDAC6 was captured with anti-Flag coupled agarose beads (Sigma F7425) and washed 3×in GB buffer. Bound proteins were eluted with SDS SB and analyzed by western blot as described in the methods for FIG. 6 using the following antibodies; anti-Flag (Sigma 3165), anti-HA (CST 3724) and anti-actin (Millipore MAB1501).

Our results suggested that a PACS1$^{R203W}$-HDAC6 axis may contribute to PACS1 Syndrome by dysregulating Golgi positioning and primary cilium integrity. We tested this possibility using siRNA knockdown methods long established in our lab (Atkins, K. M., Thomas, L., Youker, R. T., Harriff, M. J., Pissani, F., You, H., and Thomas, G. (2008). HIV-1 Nef binds PACS-2 to assemble a multikinase cascade that triggers major histocompatibility complex class I (MHC-I) down-regulation: analysis using short interfering RNA and knock-out mice. J Biol Chem 283, 11772-11784). In support for our model, we found that siRNA knockdown of either PACS1 or HDAC6 restored both Golgi positioning and ciliary integrity in PACS1$^{R203W}$ fibroblasts. By contrast, in control fibroblasts the presence or absence of either PACS1 or HDAC6 had no effect on Golgi positioning (FIGS. 8A and 8B) or ciliary integrity (FIG. 9). These experiments suggest therapeutic antisense methods that target either PACS1 or HDAC6 can be used to treat PACS1 Syndrome.

Figure 8A:
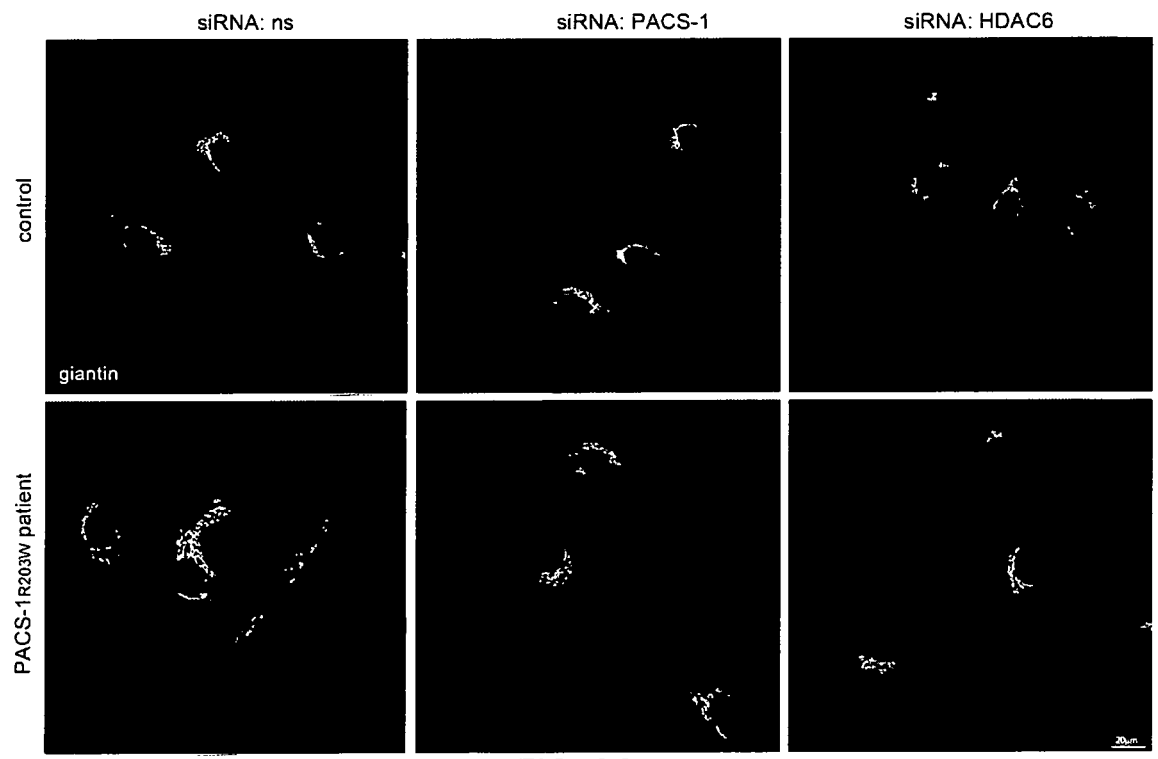
FIGS. 8A and 8B: siRNA knockdown of PACS1 or HDAC6 restores Golgi positioning in PACS1$^{R203W}$ fibroblasts.
Figure 8B:
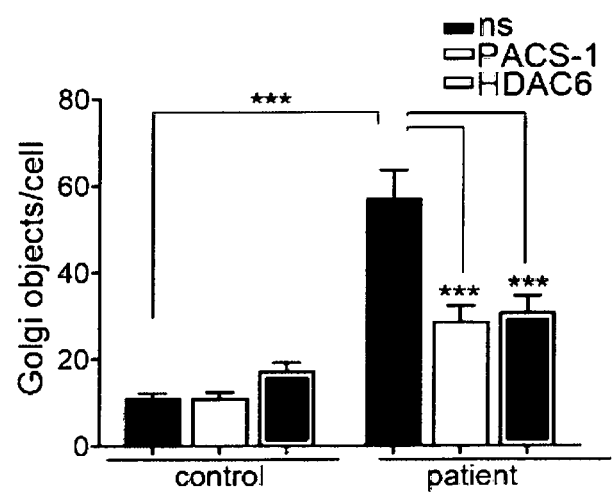
Figure 9:
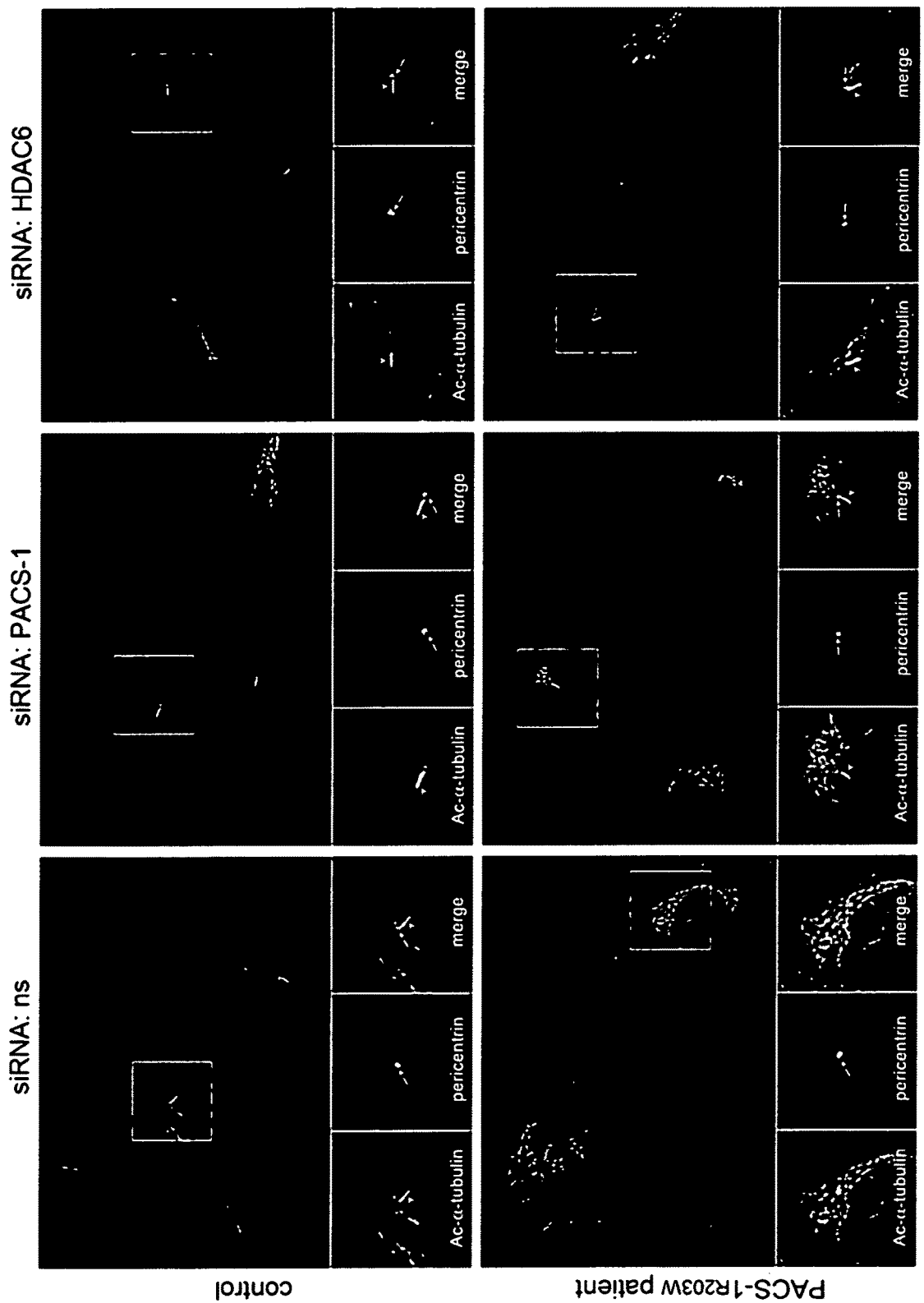
FIG. 9: siRNA knockdown of PACS1 or HDAC6 restores primary cilia in PACS1$^{R203W}$ fibroblasts. Control fibroblasts (Coriell #127160) and PACS1$^{R203W}$ fibroblasts (Coriell #127159) were treated with either a non-specific control siRNA or siRNAs specific for PACS1 or HDAC6. After 24 hours, cells were starved for an additional 24 hours to induce cilia formation. Cells were fixed with 4% paraformaldehyde, stained for pericentrin and acetylated α-tubulin and then processed for confocal microscopy. Boxed regions are enlarged and shown at the bottom of each panel. Arrowheads denote acetylated α-tubulin. Arrows denote pericentrin.

In FIGS. 8A, 8B, and 9: 5×10$^5$ control (Coriell 127160) or PACS1$^{R203W}$ patient (Coriell 127159) dermal fibroblasts were treated with either a non-specific control siRNA (Dharmacon sigenome D-001206-14-0020) or Dharmacon sigenome siRNAs specific for PACS1 (M-00697-0020) or HDAC6 (M-003499-00-0020) by nucleotransfection (Amaxa Kit V, program V-001). After 48 hours the cells were either fixed with 4% paraformaldehyde (FIGS. 8A and 8B) or starved for an additional 24 hours to induce primary cilia and then fixed (FIG. 9). The fixed cells were then processed for confocal microscopy using the methods described for FIGS. 2 (Golgi positioning) and 5 (cilia formation).

Figure 10A:
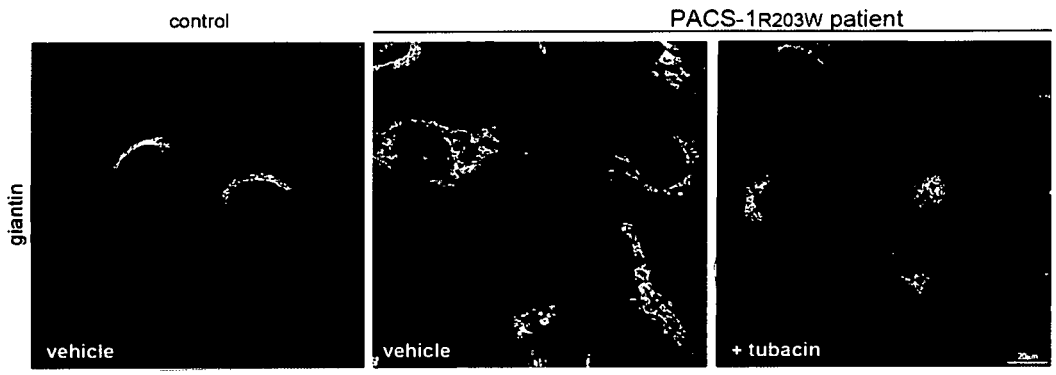
FIGS. 10A and 10B: HDAC6 inhibitors restore Golgi positioning in PACS1$^{R203W}$ patient fibroblasts. Control fibroblasts (Coriell #127160) and PACS1$^{R203W}$ fibroblasts (Coriell #127159, patient 1 and #127161, patient 2) were treated with 5 μM tubacin or vehicle alone (DMSO) for 4 hr. Cells were imaged by confocal microscopy to detect Giantin (FIG. 10A). The distance of the Golgi fragments from the center of the nucleus was quantified for each cell condition (Fiji, Image J).
Figure 10B:
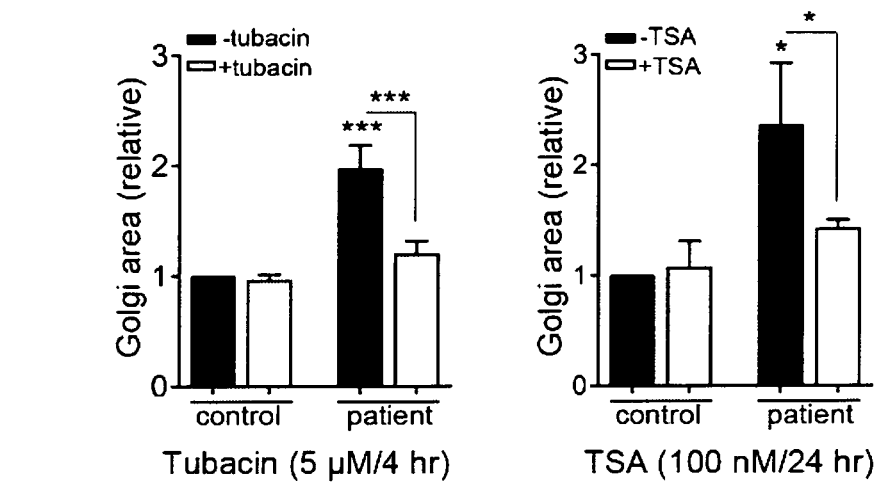
Figure 10B:
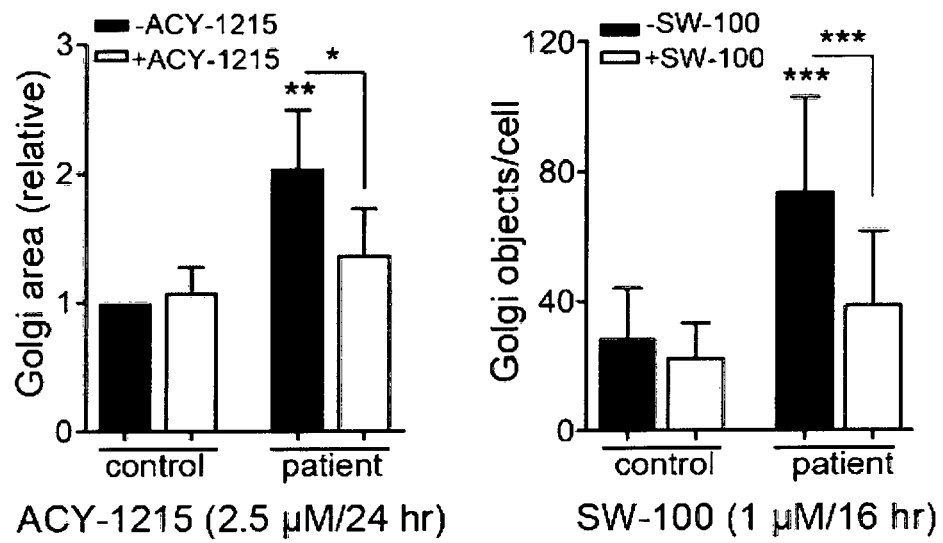

The unique structure of the HDAC6 catalytic domain has been leveraged to generate enzyme-selective inhibitors (Wang, X. X., et al. (2018). Eur J Med Chem 143, 1406-1418). We therefore asked whether treatment of PACS1$^{R203W}$ patient fibroblasts with HDAC6 inhibitors would rescue Golgi positioning. Indeed, we found that treatment of PACS1$^{R203W}$ fibroblasts with general HDAC inhibitor, TSA, as well as with multiple HDAC6-selective inhibitors, including tubacin, ACY-1215 and SW-100, rescued Golgi positioning in as little as 4 hours (FIGS. 10A and 10B). Together, our preliminary data suggest R203W is a gain-of-function mutation that dysregulates HDAC6 function that disrupts centrosomal/ciliary function and that this effect can be reversed by brain-penetrating, HDAC6-selective inhibitors.

In FIGS. 10A and 10B: Top) Control fibroblasts (Coriell #127160) and PACS1$^{R203W}$ fibroblasts (Coriell #127159, patient 1 and #127161, patient 2) were treated with 5 µM tubacin or vehicle (DMSO) for 4 hours. Cells were imaged by confocal microscopy to detect Giantin. (Bottom) The area of the Golgi region (giantin staining) was measured and normalized to the area of the nucleus in cells treated with vehicle alone or with Trichostatin A (TSA, Sigma T8552), tubacin (Caymen Chemical #13691), ACY1215 (MCE HY-16026) or SW-100 (MCE HY-115475).

Example 2—PACS2

Figure 11A:
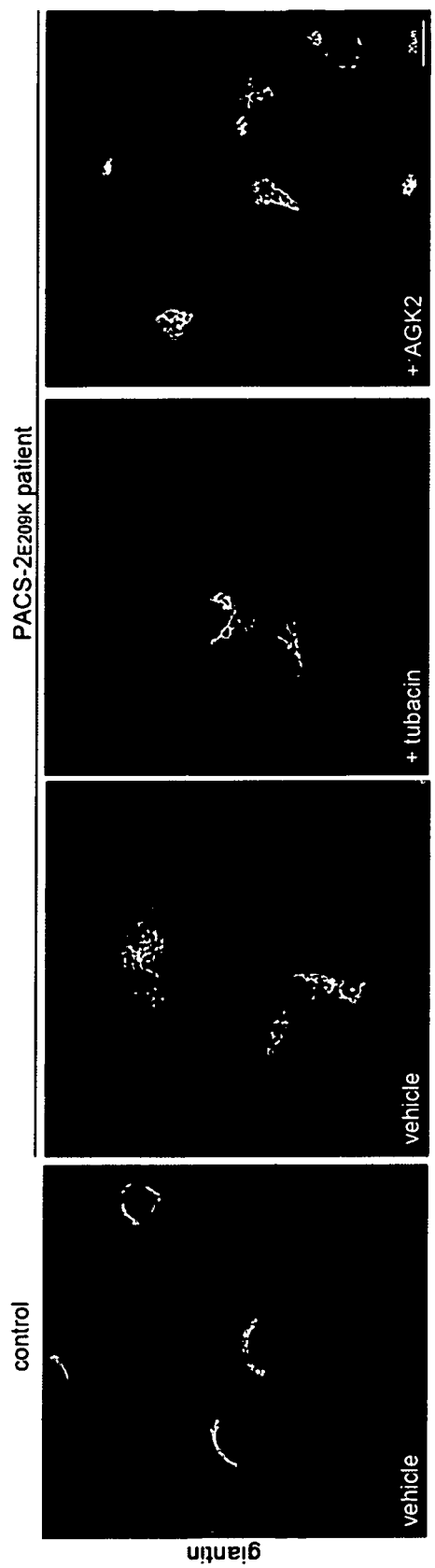
FIGS. 11A and 11B: A SIRT2 inhibitor restores Golgi positioning in PACS2$^{E209K}$ patient fibroblasts. Control fibroblasts (see also FIG. 8) and PACS2$^{E209K}$ fibroblasts (provided by H. Olson, Harvard) were treated with 5 μM tubacin (HDAC6 inhibitor), 10 μM AGK2 (SIRT2 inhibitor), 5 M tubacin+10 μM AGK2 or vehicle alone (DMSO) for 24 hr. Cells were imaged by confocal microscopy to detect Giantin. The number of dispersed Golgi mini stacks was quantified in at least 20 cells for each cell condition (Nikon Elements package). Data was analyzed using one-way Anova. Error bars represent SEM.
Figure 11B:
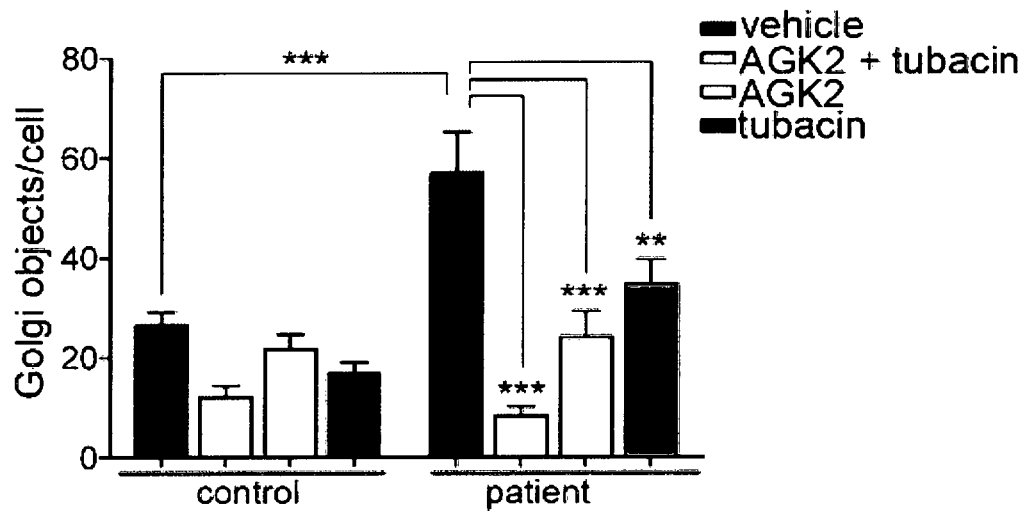

PACS2 Syndrome is caused by a Glu209->Lys mutation (Olson, H. E., Jean-Marcais, N., Yang, E., Heron, D., Tatton-Brown, K., van der Zwaag, P. A., Bijlsma, E. K., Krock, B. L., Backer, E., Kamsteeg, E. J., et al. (2018). A Recurrent De Novo PACS2 Heterozygous Missense Variant Causes Neonatal-Onset Developmental Epileptic Encephalopathy, Facial Dysmorphism, and Cerebellar Dysgenesis. Am J Hum Genet 102, 995-1007, and see FIG. 1). Based on our findings using PACS1 Syndrome cells, we asked whether fibroblasts from PACS2 Syndrome patients would similarly possess an altered Golgi structure. Confocal analysis showed that the PACS2$^{E209K}$ patient fibroblasts indeed displayed a dispersed Golgi and a disorganized microtubule cytoskeleton, very similar to that observed in PACS1$^{R203W}$ cells (FIGS. 11A and 11B). Surprisingly, however, HDAC6 inhibitors only partially restored Golgi positioning in the PACS2$^{E209K}$ cells.

Figure 12:
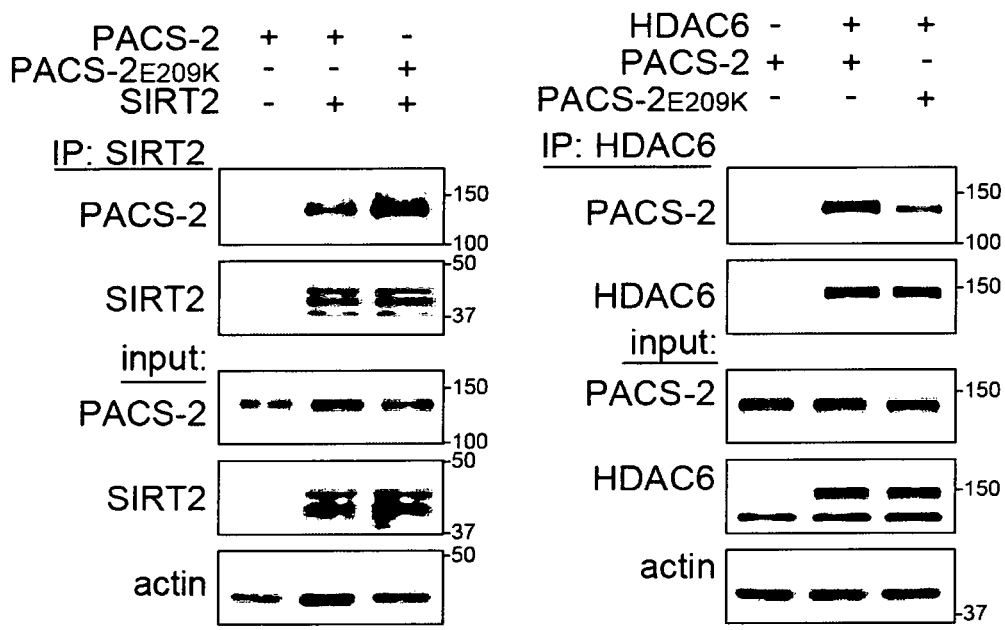
FIG. 12: SIRT2 preferentially interacts with PACS2$^{E209K}$. HCT116 cells were co-transfected with plasmids encoding Flag-tagged SIRT2 (left) or Flag-tagged HDAC6 (right) together with plasmids expressing HA-tagged PACS2 or PACS2$^{E209K}$ as indicated. Flag-tagged SIRT2 or HDAC6 were immunoprecipitated and interacting HA-tagged PACS2 or PACS2$^{E209K}$ were identified by western blot. Representative of 3 independent experiments.

The less effective ability of HDAC6 inhibitors to restore Golgi positioning in the PACS2$^{E209K}$ cells suggested another signaling pathway was preferentially activated by the PACS2 mutation to disturb Golgi and microtubule positioning. We then asked if PACS2$^{E209K}$ disturbed Golgi positioning by increasing SIRT2 activity. Co-immunoprecipitation experiments revealed that the E209K mutation increased the interaction between PACS2 and SIRT2 but decreased interaction with HDAC6 (FIG. 12). Confocal microscopy studies showed that the selective SIRT2 inhibitor, AGK2, restored Golgi positioning in PACS2$^{E209K}$ cells (FIGS. 11A and 11B).

In FIGS. 11A and 11B, (FIG. 11A) Control fibroblasts (Coriell #127160) and PACS2$^{E209K}$ fibroblasts (Olsen et al. Am J Hum Genet 102, 995-1007) were treated with vehicle (DMSO) alone (first two panels) or with either 5 µM tubacin (HDAC6 inhibitor), 10 µM AGK2 (SIRT2 inhibitor, Sigma) or 5 µM tubacin+10 µM AGK2 for 24 hours. Cells were imaged by confocal microscopy to detect Giantin. (FIG. 11B) The area of the Golgi region (giantin staining) was measured and normalized to the area of the nucleus in cells treated with vehicle alone or with the indicated inhibitors.

In FIG. 12: Replicate plates of HCT116 cells were transfected with plasmids expressing Flag-tagged SIRT2 (left) or Flag-tagged HDAC6 (right) together with HA-tagged PACS1, HA-tagged PACS1$^{R203W}$ or pcDNA3 empty vector (to normalize the amount of input plasmid) using Lipofectamine 2000. After 24 hr, cells were lysed in GB buffer (50 mM Tris pH 7.4, 150 mM NaCl, 1% NP-40, 10% glycerol plus protease inhibitors). Flag-tagged SIRT2 or HDAC6 were captured with anti-Flag coupled agarose (Sigma A2220) and the beads were washed 3×in GB buffer. Bound proteins were eluted with SDS SB and analyzed by western blot as described in the methods for FIG. 6 using the following antibodies; anti-Flag (Sigma F7425), anti-HA (CST 3724) and anti-actin (Millipore MAB1501).

Figure 13A:
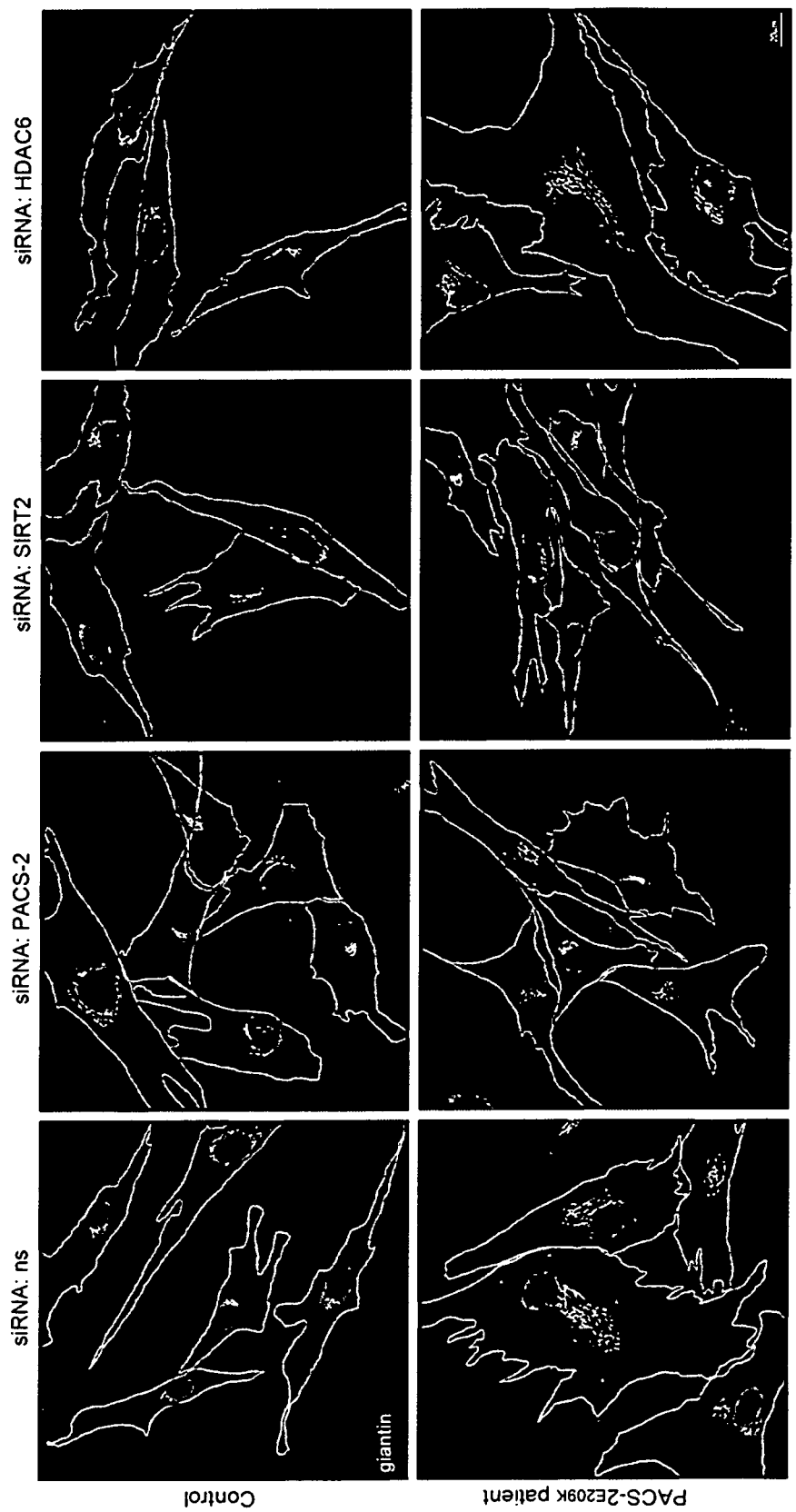
FIGS. 13A and 13B: siRNA knockdown of PACS2 or SIRT2 restores Golgi positioning in PACS2$^{E209K}$ fibroblasts.
Figure 13B:
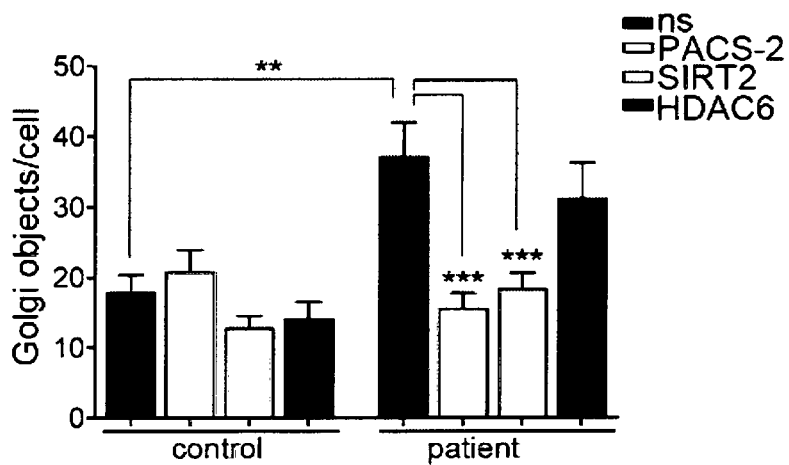

Our determination that Golgi positioning in PACS2 Syndrome fibroblasts was rescued to a greater extent with the SIRT2 inhibitor AGK2 than with the HDAC6 inhibitor tubacin (FIGS. 11A and 11B), together with the determination that SIRT2 interacted more with PACS2$^{E209K}$ than wild-type PACS2 (FIG. 12), led us to test this finding using genetic methods. We found that Golgi positioning in PACS2 Syndrome fibroblasts was rescued by siRNA knockdown of PACS2 or SIRT2 but not HDAC6 (FIGS. 13A and 13B). Together, our preliminary data suggest the E209K substitution is a gain-of-function mutation that dysregulates SIRT2 function to disrupt Golgi positioning and that this effect can be reversed by the neuroprotective SIRT2 inhibitor, AGK2 or by antisense methods.

For FIGS. 13A and 13B: 5×10$^5$ control (Coriell 127160) or PACS2$^{E209K}$ patient (Olson et al., 2018) dermal fibroblasts were treated with either a non-specific control siRNA (Dharmacon sigenome D-001206-14-0020) or Dharmacon sigenome siRNAs specific for PACS2 (M-022015-01-0020), SIRT2 (M-004826-02-0020) or HDAC6 (M-003499-00-0020) by nucleotransfection (Amaxa Kit V, program V-001). After 48 hours the cells were fixed with 4% paraformaldehyde and then processed for confocal microscopy using the methods described for FIG. 2.

Having described this invention, it will be understood to those of ordinary skill in the art that the same can be performed within a wide and equivalent range of conditions, formulations and other parameters without affecting the scope of the invention or any embodiment thereof.

The following numbered clauses describe various aspects or embodiments of the present invention:

Clause 1: A method of treating PACS1 Syndrome in a patient, comprising administering to the patient an amount of an HDAC6 inhibitor effective to treat PACS1 Syndrome in a patient, or knocking down PACS1 or HDAC6 expression in the patient.

Clause 2: The method of clause 1, comprising administering to the patient an amount of an HDAC6 inhibitor effective to treat PACS1 Syndrome in a patient.

Clause 3: The method of clause 2, wherein the HDAC6 inhibitor is a selective inhibitor of HDAC6.

Clause 4: The method of clause 2 or 3, wherein the selective inhibitor of HDAC6 is tubacin.

Clause 5: The method of clause 2 or 3, wherein the selective inhibitor of HDAC6 is tubastatin A.

Clause 6: The method of clause 2 or 3, wherein the selective inhibitor of HDAC6 is ACY-1215.

Clause 7: The method of clause 2 or 3, wherein the selective inhibitor of HDAC6 is SW-100.

Clause 8: The method of clause 1, comprising knocking down PACS1 or HDAC6 expression in the patient.

Clause 9: The method of clause 8, comprising knocking down HDAC6 expression in the patient.

Clause 10: The method of clause 8 or 9, wherein expression of PACS1 or HDAC6 is knocked down using an antisense or RNAi reagent, such as a siRNA, specific to a PACS1 or HDAC6 mRNA.

Clause 11: The method of any one of clauses 1-10, wherein the patient has a PACS1 (Arg203Trp) mutation.

Clause 12: The method of any one of clauses 1-11, wherein the patient is a human patient.

Clause 13: The method of any one of clauses 1-12, wherein the mutation in the PACS1 gene is PACS1$^{R203W}$ (e.g., SEQ ID NO: 5), such as c.607C>T (e.g., SEQ ID NO: 6).

Clause 14: A method of restoring Golgi morphology in a cell, such as a human cell, having a mutation in a PACS1 gene, such as PACS1 (Arg203Trp) (PACS1$^{R203W}$, (e.g., SEQ ID NO: 5) mutation, comprising administering to the patient an amount of an HDAC6 inhibitor effective to treat PACS1 Syndrome in a patient, or knocking down PACS1 or HDAC6 expression in the patient.

Clause 15: The method of clause 14, comprising administering to the patient an amount of an HDAC6 inhibitor effective to treat PACS1 Syndrome in a patient.

Clause 16: The method of clause 15, wherein the HDAC6 inhibitor is a selective inhibitor of HDAC6.

Clause 17: The method of clause 14 or 15, wherein the selective inhibitor of HDAC6 is tubacin.

Clause 18: The method of clause 14 or 15, wherein the selective inhibitor of HDAC6 is tubastatin A.

Clause 19: The method of clause 14 or 15, wherein the selective inhibitor of HDAC6 is ACY-1215.

Clause 20: The method of clause 14 or 15, wherein the selective inhibitor of HDAC6 is SW-100.

Clause 21: The method of clause 14, comprising knocking down PACS1 or HDAC6 expression in the patient.

Clause 22: The method of clause 21, comprising knocking down HDAC6 expression in the patient.

Clause 23: The method of clause 21 or 22, wherein expression of PACS1 or HDAC6 is knocked down using an antisense or RNAi reagent, such as a siRNA, specific to a PACS1 or HDAC6 mRNA.

Clause 24: The method of any one of clauses 14-23, wherein the cell has a PACS1 (Arg203Trp) mutation.

Clause 25: The method of any one of clauses 14-24, wherein the cell is a human cell.

Clause 26: The method of any one of clauses 14-25, wherein the mutation in the PACS1 gene is PACS1$^{R203W}$ (e.g., SEQ ID NO: 5), such as c.607C>T (e.g., SEQ ID NO: 6).

Clause 27: A method of treating PACS2 Syndrome in a patient, comprising administering to the patient an amount of a SIRT2 inhibitor effective to treat PACS2 Syndrome in a patient, or knocking down PACS2 or SIRT2 expression in the patient.

Clause 28: The method of clause 27, comprising administering to the patient an amount of a SIRT2 inhibitor effective to treat PACS2 Syndrome in a patient.

Clause 29: The method of clause 28, wherein the SIRT2 inhibitor is a selective inhibitor of SIRT2.

Clause 30: The method of clause 27 or 28 wherein the selective inhibitor of SIRT2 is AGK2.

Clause 31: The method of clause 27 or 28, wherein the selective inhibitor of SIRT2 is SirReal2, Tenovin-6, or TM.

Clause 32: The method of clause 27, comprising knocking down PACS2 or SIRT2 expression in the patient.

Clause 33: The method of clause 32, comprising knocking down SIRT2 expression in the patient.

Clause 34: The method of clause 32 or 33, wherein expression of PACS2 or SIRT2 is knocked down using an antisense or RNAi reagent, such as a siRNA, specific to a PACS2 or SIRT2 mRNA.

Clause 35: The method of any one of clauses 27-34, wherein the patient has a PACS2 (Glu209Lys) mutation.

Clause 36: The method of any one of clauses 27-35, wherein the patient is a human patient.

Clause 37: The method of any one of clauses 27-36, wherein the mutation in the PACS2 gene is PACS2$^{E209K}$ (e.g., SEQ ID NO: 7), such as c.625G>A (e.g., SEQ ID NO: 8).

Clause 38: A method of restoring Golgi morphology in a cell having a mutation in a PACS2 gene, such as a PACS2 (Glu209Lys) (e.g., PACS2E$^{209K}$, SEQ ID NO: 7) mutation, comprising administering to the patient an amount of a SIRT2 inhibitor effective to treat PACS2 Syndrome in a patient, or knocking down PACS2 or SIRT2 expression in the cell.

Clause 39: The method of clause 38, comprising administering to the patient an amount of a SIRT2 inhibitor effective to treat PACS2 Syndrome in a patient.

Clause 40: The method of clause 39, wherein the SIRT2 inhibitor is a selective inhibitor of SIRT2.

Clause 41: The method of clause 38 or 39, wherein the selective inhibitor of SIRT2 is AGK2.

Clause 42: The method of clause 38 or 39, wherein the selective inhibitor of SIRT2 is SirReal2, Tenovin-6, or TM.

Clause 43: The method of clause 38, comprising knocking down PACS2 or SIRT2 expression in the patient.

Clause 44: The method of clause 43, comprising knocking down SIRT2 expression in the patient.

Clause 45: The method of clause 43 or 44, wherein expression of PACS2 or SIRT2 is knocked down using an antisense or RNAi reagent, such as a siRNA, specific to a PACS2 or SIRT2 mRNA.

Clause 46: The method of any one of clauses 38-45, wherein the cell has a PACS2 (Glu209Lys) mutation.

Clause 47: The method of any one of clauses 38-46, wherein the cell is a human cell.

Clause 48: The method of any one of clauses 38-47, wherein the mutation in the PACS2 gene is PACS2$^{E209K}$ (e.g., SEQ ID NO: 7), such as c.625G>A (e.g., SEQ ID NO: 8).

We claim:

1. A method of treating PACS1 Syndrome in a patient or restoring Golgi morphology in a cell having a mutation in a PACS1 gene, comprising administering to the patient an amount of an HDAC6 inhibitor effective to treat PACS1 Syndrome in a patient, or knocking down PACS1 or HDAC6 expression in the patient.

2. The method of claim 1, comprising administering to the patient an amount of an HDAC6 inhibitor effective to treat PACS1 Syndrome in a patient.

3. The method of claim 2, wherein the HDAC6 inhibitor is a selective inhibitor of HDAC6.

4. The method of claim 3, wherein the selective inhibitor of HDAC6 is tubacin, tubastatin A, ACY-1215, or SW-100.

5. The method of claim 1, comprising knocking down PACS1 or HDAC6 expression in the patient.

6. The method of claim 5, wherein expression of PACS1 or HDAC6 is knocked down using an antisense or RNAi reagent specific to a PACS1 or HDAC6 mRNA.

7. The method of claim 1, wherein the patient or cell has a PACS1$^{R203W}$ mutation and/or the patient is a human patient.

8. The method of claim 1, for restoring Golgi morphology in a cell having a mutation in a PACS1 gene, comprising administering to the patient an amount of an HDAC6 inhibitor effective to treat PACS1 Syndrome in a patient, or knocking down PACS1 or HDAC6 expression in the patient.

9. A method of treating PACS2 Syndrome in a patient or restoring Golgi morphology in a cell having a mutation in a PACS2 gene, comprising administering to the patient an amount of a SIRT2 inhibitor effective to treat PACS2 Syndrome in a patient, or knocking down PACS2 or SIRT2 expression in the patient.

10. The method of claim 9, comprising administering to the patient an amount of a SIRT2 inhibitor effective to treat PACS2 Syndrome in a patient.

11. The method of claim 10, wherein the SIRT2 inhibitor is a selective inhibitor of SIRT2.

12. The method of claim 11, wherein the selective inhibitor of SIRT2 is AGK2, SirReal2, Tenovin-6, or TM.

13. The method of claim 9, comprising knocking down PACS2 or SIRT2 expression in the patient.

14. The method of claim 13, wherein expression of PACS2 or SIRT2 is knocked down using an antisense or RNAi reagent specific to a PACS2 or SIRT2 mRNA.

15. The method of claim 9, wherein the patient or cell has a PACS2$^{E209K}$ mutation, such as c.625G>A, and/or the patient is a human patient.

16. The method of claim 9, for restoring Golgi morphology in a cell having a mutation in a PACS2 gene, such as a PACS2 (Glu209Lys) (PACS2$^{E209K}$) mutation, comprising administering to the patient an amount of a SIRT2 inhibitor effective to treat PACS2 Syndrome in a patient, or knocking down PACS2 or SIRT2 expression in the cell.

17. The method of claim 1, for treating PACS1 Syndrome in a patient.

18. The method of claim 9, for treating PACS2 Syndrome in a patient.

19. The method of claim 6, wherein the antisense reagent or RNAi is siRNA.

20. The method of claim 7, wherein the $PACS1^{R203W}$ mutation is c.607C>T.

21. The method of claim 8, wherein the cell is a human cell.

22. The method of claim 8, wherein the mutation in the PACS1 gene is PACS1 (Arg203Trp) ($PACS1^{R203W}$).

23. The method of claim 14, wherein the antisense reagent or RNAi is siRNA.

24. The method of claim 15, wherein the $PACS2^{E209K}$ mutation, is c.625G>A.

25. The method of claim 16, wherein the mutation in the PACS2 gene is PACS2 (Glu209Lys) ($PACS2^{E209K}$).

* * * * *

UNITED STATES PATENT AND TRADEMARK OFFICE
CERTIFICATE OF CORRECTION

PATENT NO. : 12,161,639 B2
APPLICATION NO. : 17/260713
DATED : December 10, 2024
INVENTOR(S) : Gary Thomas Page 1 of 1

It is certified that error appears in the above-identified patent and that said Letters Patent is hereby corrected as shown below:

In the Claims

Column 58, Line 60, Claim 15, delete "mutation, such as c.625G>A, and/or" and insert -- mutation and/or --

Column 58, Lines 63-64, Claim 16, delete "gene, such as a PACS2 (Glu209Lys) (PACS2$^{E209K}$) mutation, comprising" and insert -- gene, comprising --

Column 59, Line 15, Claim 24, delete "PACS2$^{E209K}$" and insert -- PACS2$^{E209K}$ --

Signed and Sealed this
Fourth Day of March, 2025

Coke Morgan Stewart
*Acting Director of the United States Patent and Trademark Office*

SEQUENCE LISTING

<160> NUMBER OF SEQ ID NOS: 9

<210> SEQ ID NO 1
<211> LENGTH: 1229
<212> TYPE: PRT
<213> ORGANISM: Homo sapiens

<400> SEQUENCE: 1

```
Met Ser Gly Ala Asn Arg Gly Arg Gly Gln Ala Ser Ser Thr Met Thr
1               5                   10                  15

Ser Thr Gly Gln Asp Ser Thr Thr Arg Gln Arg Arg Ser Arg Gln
            20                  25                  30

Asn Pro Gln Ser Pro Pro Gln Asp Ser Ser Val Thr Ser Lys Arg Asn
                35                  40                  45

Ile Lys Lys Gly Ala Val Pro Arg Ser Ile Pro Asn Leu Ala Glu Val
        50                  55                  60

Lys Lys Lys Gly Lys Met Lys Lys Leu Gly Gln Ala Met Glu Glu Asp
65                  70                  75                  80

Leu Ile Val Gly Leu Gln Gly Met Asp Leu Asn Leu Glu Ala Glu Ala
                85                  90                  95

Leu Ala Gly Thr Gly Leu Val Leu Asp Glu Gln Leu Asn Glu Phe His
            100                 105                 110

Cys Leu Trp Asp Asp Ser Phe Pro Glu Gly Pro Glu Arg Leu His Ala
        115                 120                 125

Ile Lys Glu Gln Leu Ile Gln Glu Gly Leu Leu Asp Arg Cys Val Ser
    130                 135                 140

Phe Gln Ala Arg Phe Ala Glu Lys Glu Leu Met Leu Val His Ser
145                 150                 155                 160

Leu Glu Tyr Ile Asp Leu Met Glu Thr Thr Gln Tyr Met Asn Glu Gly
                165                 170                 175

Glu Leu Arg Val Leu Ala Asp Thr Tyr Asp Ser Val Tyr Leu His Pro
            180                 185                 190

Asn Ser Tyr Ser Cys Ala Cys Leu Ala Ser Gly Ser Val Leu Arg Leu
        195                 200                 205

Val Asp Ala Val Leu Gly Ala Glu Ile Arg Asn Gly Met Ala Ile Ile
    210                 215                 220

Arg Pro Pro Gly His His Ala Gln His Ser Leu Met Asp Gly Tyr Cys
225                 230                 235                 240

Met Phe Asn His Val Ala Val Ala Ala Arg Tyr Ala Gln Gln Lys His
                245                 250                 255

Arg Ile Arg Arg Val Leu Ile Val Asp Trp Asp Val His His Gly Gln
            260                 265                 270

Gly Thr Gln Phe Thr Phe Asp Gln Asp Pro Ser Val Leu Tyr Phe Ser
        275                 280                 285

Ile His Arg Tyr Glu Gln Gly Arg Phe Trp Pro His Leu Lys Ala Ser
    290                 295                 300

Asn Trp Ser Thr Thr Gly Phe Gly Gln Gly Gln Gly Tyr Thr Ile Asn
305                 310                 315                 320

Val Pro Trp Asn Gln Val Gly Met Arg Asp Ala Asp Tyr Ile Ala Ala
                325                 330                 335

Phe Leu His Val Leu Leu Pro Val Ala Leu Glu Phe Gln Pro Gln Leu
            340                 345                 350

Val Leu Val Ala Ala Gly Phe Asp Ala Leu Gln Gly Asp Pro Lys Gly
        355                 360                 365
```

```
Glu Met Ala Ala Thr Pro Ala Gly Phe Ala Gln Leu Thr His Leu Leu
370                 375                 380

Met Gly Leu Ala Gly Gly Lys Leu Ile Leu Ser Leu Glu Gly Gly Tyr
385                 390                 395                 400

Asn Leu Arg Ala Leu Ala Glu Gly Val Ser Ala Ser Leu His Thr Leu
            405                 410                 415

Leu Gly Asp Pro Cys Pro Met Leu Glu Ser Pro Gly Ala Pro Cys Arg
            420                 425                 430

Ser Ala Gln Ala Ser Val Ser Cys Ala Leu Glu Ala Leu Glu Pro Phe
            435                 440                 445

Trp Glu Val Leu Val Arg Ser Thr Glu Thr Val Glu Arg Asp Asn Met
450                 455                 460

Glu Glu Asp Asn Val Glu Glu Ser Glu Glu Gly Pro Trp Glu Pro
465                 470                 475                 480

Pro Val Leu Pro Ile Leu Thr Trp Pro Val Leu Gln Ser Arg Thr Gly
            485                 490                 495

Leu Val Tyr Asp Gln Asn Met Met Asn His Cys Asn Leu Trp Asp Ser
            500                 505                 510

His His Pro Glu Val Pro Gln Arg Ile Leu Arg Ile Met Cys Arg Leu
            515                 520                 525

Glu Glu Leu Gly Leu Ala Gly Arg Cys Leu Thr Leu Thr Pro Arg Pro
530                 535                 540

Ala Thr Glu Ala Glu Leu Leu Thr Cys His Ser Ala Glu Tyr Val Gly
545                 550                 555                 560

His Leu Arg Ala Thr Glu Lys Met Lys Thr Arg Glu Leu His Arg Glu
            565                 570                 575

Ser Ser Asn Phe Asp Ser Ile Tyr Ile Cys Pro Ser Thr Phe Ala Cys
            580                 585                 590

Ala Gln Leu Ala Thr Gly Ala Ala Cys Arg Leu Val Glu Ala Val Leu
            595                 600                 605

Ser Gly Glu Val Leu Asn Gly Ala Ala Val Val Arg Pro Pro Gly His
610                 615                 620

His Ala Glu Gln Asp Ala Ala Cys Gly Phe Cys Phe Phe Asn Ser Val
625                 630                 635                 640

Ala Val Ala Ala Arg His Ala Gln Thr Ile Ser Gly His Ala Leu Arg
            645                 650                 655

Ile Leu Ile Val Asp Trp Asp Val His His Gly Asn Gly Thr Gln His
            660                 665                 670

Met Phe Glu Asp Asp Pro Ser Val Leu Tyr Val Ser Leu His Arg Tyr
            675                 680                 685

Asp His Gly Thr Phe Phe Pro Met Gly Asp Glu Gly Ala Ser Ser Gln
            690                 695                 700

Ile Gly Arg Ala Ala Gly Thr Gly Phe Thr Val Asn Val Ala Trp Asn
705                 710                 715                 720

Gly Pro Arg Met Gly Asp Ala Asp Tyr Leu Ala Ala Trp His Arg Leu
            725                 730                 735

Val Leu Pro Ile Ala Tyr Glu Phe Asn Pro Glu Leu Val Leu Val Ser
            740                 745                 750

Ala Gly Phe Asp Ala Ala Arg Gly Asp Pro Leu Gly Gly Cys Gln Val
            755                 760                 765

Ser Pro Glu Gly Tyr Ala His Leu Thr His Leu Leu Met Gly Leu Ala
            770                 775                 780

Ser Gly Arg Ile Ile Leu Ile Leu Glu Gly Gly Tyr Asn Leu Thr Ser
```

-continued

```
            785                 790                 795                 800
        Ile Ser Glu Ser Met Ala Ala Cys Thr Arg Ser Leu Leu Gly Asp Pro
                        805                 810                 815

Pro Pro Leu Leu Thr Leu Pro Arg Pro Pro Leu Ser Gly Ala Leu Ala
                        820                 825                 830

Ser Ile Thr Glu Thr Ile Gln Val His Arg Arg Tyr Trp Arg Ser Leu
                        835                 840                 845

Arg Val Met Lys Val Glu Asp Arg Gly Pro Ser Ser Ser Lys Leu
                        850                 855                 860

Val Thr Lys Lys Ala Pro Gln Pro Ala Lys Pro Arg Leu Ala Glu Arg
        865                 870                 875                 880

Met Thr Thr Arg Glu Lys Lys Val Leu Glu Ala Gly Met Gly Lys Val
                        885                 890                 895

Thr Ser Ala Ser Phe Gly Glu Glu Ser Thr Pro Gly Gln Thr Asn Ser
                        900                 905                 910

Glu Thr Ala Val Val Ala Leu Thr Gln Asp Gln Pro Ser Glu Ala Ala
                        915                 920                 925

Thr Gly Gly Ala Thr Leu Ala Gln Thr Ile Ser Glu Ala Ala Ile Gly
                        930                 935                 940

Gly Ala Met Leu Gly Gln Thr Thr Ser Glu Glu Ala Val Gly Gly Ala
        945                 950                 955                 960

Thr Pro Asp Gln Thr Thr Ser Glu Glu Thr Val Gly Gly Ala Ile Leu
                        965                 970                 975

Asp Gln Thr Thr Ser Glu Asp Ala Val Gly Gly Ala Thr Leu Gly Gln
                        980                 985                 990

Thr Thr Ser Glu Glu Ala Val Gly Gly Ala Thr Leu Ala Gln Thr Thr
                        995                 1000                1005

Ser Glu Ala Ala Met Glu Gly Ala Thr Leu Asp Gln Thr Thr Ser
                    1010                1015                1020

Glu Glu Ala Pro Gly Gly Thr Glu Leu Ile Gln Thr Pro Leu Ala
                    1025                1030                1035

Ser Ser Thr Asp His Gln Thr Pro Pro Thr Ser Pro Val Gln Gly
                    1040                1045                1050

Thr Thr Pro Gln Ile Ser Pro Ser Thr Leu Ile Gly Ser Leu Arg
                    1055                1060                1065

Thr Leu Glu Leu Gly Ser Glu Ser Gln Gly Ala Ser Glu Ser Gln
                    1070                1075                1080

Ala Pro Gly Glu Glu Asn Leu Leu Gly Glu Ala Gly Gly Gln
                    1085                1090                1095

Asp Met Ala Asp Ser Met Leu Met Gln Gly Ser Arg Gly Leu Thr
                    1100                1105                1110

Asp Gln Ala Ile Phe Tyr Ala Val Thr Pro Leu Pro Trp Cys Pro
                    1115                1120                1125

His Leu Val Ala Val Cys Pro Ile Pro Ala Ala Gly Leu Asp Val
                    1130                1135                1140

Thr Gln Pro Cys Gly Asp Cys Gly Thr Ile Gln Glu Asn Trp Val
                    1145                1150                1155

Cys Leu Ser Cys Tyr Gln Val Tyr Cys Gly Arg Tyr Ile Asn Gly
                    1160                1165                1170

His Met Leu Gln His His Gly Asn Ser Gly His Pro Leu Val Leu
                    1175                1180                1185

Ser Tyr Ile Asp Leu Ser Ala Trp Cys Tyr Tyr Cys Gln Ala Tyr
                    1190                1195                1200
```

| Val | His | His | Gln | Ala | Leu | Leu | Asp | Val | Lys | Asn | Ile | Ala | His | Gln |
|---|---|---|---|---|---|---|---|---|---|---|---|---|---|---|
| 1205 | | | | | 1210 | | | | 1215 | | | | | |

| Asn | Lys | Phe | Gly | Glu | Asp | Met | Pro | His | Pro | His |
|---|---|---|---|---|---|---|---|---|---|---|
| 1220 | | | | | 1225 | | | | | |

<210> SEQ ID NO 2
<211> LENGTH: 4147
<212> TYPE: DNA
<213> ORGANISM: Homo sapiens

<400> SEQUENCE: 2

| | |
|---|---|
| cacggcgcgt cgcgcgggaa gtcgcgggga aaaggtcgcc agaaacttgg tggagcgagc | 60 |
| caagggcgga gtttgagaaa ggggctgcgt ccaatgagtg gagcgaaccg cggcaggggc | 120 |
| caagcctcct caactatgac ctcaaccggc aggattccca ccacaaccag gcagcgaaga | 180 |
| agtaggcaga accccccagtc gcccccctcag gactccagtg tcacttcgaa gcgaaatatt | 240 |
| aaaaagggag ccgttccccg ctctatcccc aatctagcgg aggtaaagaa gaaaggcaaa | 300 |
| atgaagaagc tcggccaagc aatggaagaa gacctaatcg tgggactgca agggatggat | 360 |
| ctgaaccttg aggctgaagc actggctggc actggcttgg tgttggatga gcagttaaat | 420 |
| gaattccatt gcctctggga tgacagcttc ccggaaggcc ctgagcggct ccatgccatc | 480 |
| aaggagcaac tgatccagga gggcctccta gatcgctgcg tgtcctttca ggcccggttt | 540 |
| gctgaaaagg aagagctgat gttggttcac agcctagaat atattgatct gatggaaaca | 600 |
| acccagtaca tgaatgaggg agaactccgt gtcctagcag acacctacga ctcagtttat | 660 |
| ctgcatccga actcatactc ctgtgcctgc ctggcctcag gctctgtcct caggctggtg | 720 |
| gatgcggtcc tgggggctga gatccggaat ggcatggcca tcattaggcc tcctggacat | 780 |
| cacgcccagc acagtcttat ggatggctat tgcatgttca ccacgtggc cgtgtggcagcc | 840 |
| cgctatgctc aacagaaaca ccgcatccgg agggtcctta cgtagattg ggatgtgcac | 900 |
| cacggtcaag aacacagtt caccttcgac caggacccca gtgtcctcta tttctccatc | 960 |
| caccgctacg agcagggtag gttctggccc cacctgaagg cctctaactg gtccaccaca | 1020 |
| ggtttcggcc aaggccaagg ataccatc aatgtgcctt ggaaccaggt ggggatgcgg | 1080 |
| gatgctgact acattgctgc tttcctgcac gtcctgctgc cagtcgccct cgagttccag | 1140 |
| cctcagctgg tcctggtggc tgctggattt gatgccctgc aaggggaccc caagggtgag | 1200 |
| atggccgcca ctccggcagg gttcgcccag ctaacccacc tgctcatggg tctggcagga | 1260 |
| ggcaagctga tcctgtctct ggagggtggc tacaacctcc gcgccctggc tgaaggcgtc | 1320 |
| agtgcttcgc tccacaccct tctgggagac ccttgcccca tgctggagtc acctggtgcc | 1380 |
| ccctgccgga gtgcccaggc ttcagtttcc tgtgctctgg aagcccttga gcccttctgg | 1440 |
| gaggttcttg tgagatcaac tgagaccgtg gagagggaca catggagga ggacaatgta | 1500 |
| gaggagagcg aggaggaagg accctgggag ccccctgtgc tcccaatcct gacatggcca | 1560 |
| gtgctacagt ctcgcacagg gctggtctat gaccaaaata tgatgaatca ctgcaacttg | 1620 |
| tgggacagcc accaccctga ggtacccag cgcatcttgc ggatcatgtg ccgtctggag | 1680 |
| gagctgggcc ttgccgggcg ctgcctcacc ctgacaccgc ccctgccac agaggctgag | 1740 |
| ctgctcacct gtcacagtgc tgagtacgtg gtcatctcc gggccacaga gaaaatgaaa | 1800 |
| acccgggagc tgcaccgtga gagttccaac tttgactcca tctatatctg ccccagtacc | 1860 |
| ttcgcctgtg cacagcttgc cactggcgct gcctgccgcc tggtgaggc tgtgctctca | 1920 |

```
ggagaggttc tgaatggtgc tgctgtggtg cgtcccccag gacaccacgc agagcaggat   1980
gcagcttgcg gttttttgctt tttcaactct gtggctgtgg ctgctcgcca tgcccagact   2040
atcagtgggc atgccctacg gatcctgatt gtggattggg atgtccacca cggtaatgga   2100
actcagcaca tgtttgagga tgaccccagt gtgctatatg tgtccctgca ccgctatgat   2160
catggcacct tcttccccat gggggatgag ggtgccagca gccagatcgg ccgggctgcg   2220
ggcacaggct tcaccgtcaa cgtggcatgg aacgggcccc gcatgggtga tgctgactac   2280
ctagctgcct ggcatcgcct ggtgcttccc attgcctacg agtttaaccc agaactggtg   2340
ctggtctcag ctggctttga tgctgcacgg ggggatccgc tggggggctg ccaggtgtca   2400
cctgagggtt atgcccacct cacccacctg ctgatgggcc ttgccagtgg ccgcattatc   2460
cttatcctag agggtggcta taacctgaca tccatctcag agtccatggc tgcctgcact   2520
cgctccctcc ttggagaccc accaccccctg ctgaccctgc cacggccccc actatcaggg   2580
gccctggcct caatcactga gaccatccaa gtccatcgca gatactggcg cagcttacgg   2640
gtcatgaagg tagaagacag agaaggaccc tccagttcta agttggtcac caagaaggca   2700
ccccaaccag ccaaacctag gttagctgag cggatgacca cacgagaaaa gaaggttctg   2760
gaagcaggca tggggaaagt caccctcggca tcatttgggg aagagtccac tccaggccag   2820
actaactcag agacagctgt ggtggccctc actcaggacc agccctcaga ggcagccaca   2880
gggggagcca ctctggccca gaccatttct gaggcagcca ttgggggagc catgctgggc   2940
cagaccacct cagaggaggc tgtcggggga gccactccgg accagaccac ctcagaggag   3000
actgtgggag gagccattct ggaccagacc acctcagagg atgctgttgg gggagccacg   3060
ctgggccaga ctacctcaga ggaggctgta ggaggagcta cactggccca gaccacctcg   3120
gaggcagcca tggagggagc cacactggac cagactacgt cagaggaggc tccagggggc   3180
accgagctga tccaaactcc tctagcctcg agcacagacc accagacccc cccaacctca   3240
cctgtgcagg gaactacacc ccagatatct cccagtacac tgattgggag tctcaggacc   3300
ttggagctag gcagcgaatc tcagggggcc tcagaatctc aggccccagg agaggagaac   3360
ctactaggag aggcagctgg aggtcaggac atggctgatt cgatgctgat gcagggatct   3420 agggggcctca ctgatcaggc catatttttat gctgtgacac cactgccctg gtgtccccat   3480
ttggtggcag tatgccccat acctgcagca ggcctagacg tgacccaacc ttgtggggac   3540
tgtggaacaa tccaagagaa ttgggtgtgt ctctcttgct atcaggtcta ctgtggtcgt   3600
tacatcaatg ccacatgct ccaacaccat ggaaattctg gacacccgct ggtcctcagc   3660
tacatcgacc tgtcagcctg gtgttactac tgtcaggcct atgtccacca ccaggctctc   3720
ctagatgtga agaacatcgc ccaccagaac aagtttgggg aggatatgcc ccacccacac   3780 taagcccag aatacggtcc ctcttcacct tctgaggccc acgatagacc agctgtagct   3840
cattccagcc tgtaccttgg atgagggta gcctcccact gcatcccatc ctgaatatcc   3900
tttgcaactc cccaagagtg cttatttaag tgttaatact tttaagagaa ctgcgacgat   3960
taattgtgga tctccccctg cccattgcct gcttgagggg caccactact ccagcccaga   4020
aggaaagggg ggcagctcag tggccccaag agggagctga tatcatgagg ataacattgg   4080
cgggagggga gttaactggc aggcatggca aggttgcata tgtaataaag tacaagctgt   4140
taaaaaa                                                            4147

<210> SEQ ID NO 3
<211> LENGTH: 389
```

<212> TYPE: PRT
<213> ORGANISM: Homo sapiens

<400> SEQUENCE: 3

Met Ala Glu Pro Asp Pro Ser His Pro Leu Glu Thr Gln Ala Gly Lys
1               5                   10                  15

Val Gln Glu Ala Gln Asp Ser Asp Ser Glu Gly Gly Ala Ala
            20                  25                  30

Gly Gly Glu Ala Asp Met Asp Phe Leu Arg Asn Leu Phe Ser Gln Thr
        35                  40                  45

Leu Ser Leu Gly Ser Gln Lys Glu Arg Leu Leu Asp Glu Leu Thr Leu
    50                  55                  60

Glu Gly Val Ala Arg Tyr Met Gln Ser Glu Arg Cys Arg Arg Val Ile
65                  70                  75                  80

Cys Leu Val Gly Ala Gly Ile Ser Thr Ser Ala Gly Ile Pro Asp Phe
                85                  90                  95

Arg Ser Pro Ser Thr Gly Leu Tyr Asp Asn Leu Glu Lys Tyr His Leu
            100                 105                 110

Pro Tyr Pro Glu Ala Ile Phe Glu Ile Ser Tyr Phe Lys Lys His Pro
        115                 120                 125

Glu Pro Phe Phe Ala Leu Ala Lys Glu Leu Tyr Pro Gly Gln Phe Lys
    130                 135                 140

Pro Thr Ile Cys His Tyr Phe Met Arg Leu Leu Lys Asp Lys Gly Leu
145                 150                 155                 160

Leu Leu Arg Cys Tyr Thr Gln Asn Ile Asp Thr Leu Glu Arg Ile Ala
                165                 170                 175

Gly Leu Glu Gln Glu Asp Leu Val Glu Ala His Gly Thr Phe Tyr Thr
            180                 185                 190

Ser His Cys Val Ser Ala Ser Cys Arg His Glu Tyr Pro Leu Ser Trp
        195                 200                 205

Met Lys Glu Lys Ile Phe Ser Glu Val Thr Pro Lys Cys Glu Asp Cys
    210                 215                 220

Gln Ser Leu Val Lys Pro Asp Ile Val Phe Phe Gly Glu Ser Leu Pro
225                 230                 235                 240

Ala Arg Phe Phe Ser Cys Met Gln Ser Asp Phe Leu Lys Val Asp Leu
                245                 250                 255

Leu Leu Val Met Gly Thr Ser Leu Gln Val Gln Pro Phe Ala Ser Leu
            260                 265                 270

Ile Ser Lys Ala Pro Leu Ser Thr Pro Arg Leu Leu Ile Asn Lys Glu
        275                 280                 285

Lys Ala Gly Gln Ser Asp Pro Phe Leu Gly Met Ile Met Gly Leu Gly
    290                 295                 300

Gly Gly Met Asp Phe Asp Ser Lys Lys Ala Tyr Arg Asp Val Ala Trp
305                 310                 315                 320

Leu Gly Glu Cys Asp Gln Gly Cys Leu Ala Leu Ala Glu Leu Leu Gly
                325                 330                 335

Trp Lys Lys Glu Leu Glu Asp Leu Val Arg Arg Glu His Ala Ser Ile
            340                 345                 350

Asp Ala Gln Ser Gly Ala Gly Val Pro Asn Pro Ser Thr Ser Ala Ser
        355                 360                 365

Pro Lys Lys Ser Pro Pro Ala Lys Asp Glu Ala Arg Thr Thr Glu
    370                 375                 380

Arg Glu Lys Pro Gln
385

<210> SEQ ID NO 4
<211> LENGTH: 1862
<212> TYPE: DNA
<213> ORGANISM: Homo sapiens

<400> SEQUENCE: 4

```
agtcggtgac aggacagagc agtcggtgac gggacacagt ggttggtgac gggacagagc     60
ggtcggtgac agcctcaagg gcttcagcac cgcgcccatg gcagagccag accccctctca   120
ccctctggag acccaggcag ggaaggtgca ggaggctcag gactcagatt cagactctga    180
gggaggagcc gctggtggag aagcagacat ggacttcctg cggaacttat tctcccagac    240
gctcagcctg ggcagccaga aggagcgtct gctggacgag ctgaccttgg aagggggtggc   300
ccggtacatg cagagcgaac gctgtcgcag agtcatctgt ttggtgggag ctggaatctc    360
cacatccgca ggcatccccg actttcgctc tccatccacc ggcctctatg caacctaga    420
gaagtaccat cttccctacc cagaggccat ctttgagatc agctatttca gaaacatcc    480
ggaaccctt tcgccctcg ccaaggaact ctatcctggg cagttcaagc caaccatctg     540
tcactacttc atgcgcctgc tgaaggacaa ggggctactc ctgcgctgct acacgcagaa   600
catagatacc ctggagcgaa tagccgggct ggaacaggag gacttggtgg aggcgcacgg   660
caccttctac acatcacact gcgtcagcgc cagctgccgg cacgaatacc cgctaagctg   720
gatgaaagag aagatcttct ctgaggtgac gcccaagtgt gaagactgtc agagcctggt   780
gaagcctgat atcgtctttt tggtgagag cctcccagcg cgtttcttct cctgtatgca    840
gtcagacttc ctgaaggtgg acctcctcct ggtcatgggt acctccttgc aggtgcagcc   900
ctttgcctcc ctcatcagca aggcaccct ctccacccct cgcctgctca tcaacaagga   960
gaaagctggc cagtcggacc ctttcctggg gatgattatg ggcctcggag gaggcatgga  1020
ctttgactcc aagaaggcct acagggacgt ggcctggctg ggtgaatgcg accagggctg  1080
cctggcccctt gctgagctcc ttggatggaa gaaggagctg gaggaccttg tccggaggga  1140
gcacgccagc atagatgccc agtcgggggc gggggtcccc aacccccagca cttcagcttc  1200
ccccaagaag tccccgccac ctgccaagga cgaggccagg acaacagaga gggagaaacc  1260
ccagtgacag ctgcatctcc caggcgggat gccgagctcc tcagggacag ctgagcccca  1320
accgggcctg gccccctctt aaccagcagt tcttgtctgg ggagctcaga acatccccca  1380
atctcttaca gctccctccc caaaactggg gtcccagcaa ccctggcccc caaccccagc  1440
aaatctctaa cacctcctag aggccaaggc ttaaacaggc atctctacca gccccactgt  1500
ctctaaccac tcctgggcta aggagtaacc tccctcatct ctaactgccc ccacggggcc  1560
agggctaccc cagaactttt aactcttcca ggacagggag cttcgggccc ccactctgtc  1620
tcctgccccc gggggcctgt ggctaagtaa accataccta acctacccca gtgtgggtgt  1680
gggcctctga atataaccca cacccagcgt aggggagtc tgagccggga gggctcccga   1740
gtctctgcct tcagctccca aagtgggtgg tgggccccct tcacgtggga cccacttccc  1800
atgctggatg ggcagaagac attgcttatt ggagacaaat taaaaacaaa aacaactaac  1860
aa                                                                 1862
```

<210> SEQ ID NO 5
<211> LENGTH: 963
<212> TYPE: PRT
<213> ORGANISM: Homo sapiens

<400> SEQUENCE: 5

Met Ala Glu Arg Gly Gly Ala Gly Gly Pro Gly Gly Ala Gly Gly
1               5                   10                  15

Gly Ser Gly Gln Arg Gly Ser Gly Val Ala Gln Ser Pro Gln Gln Pro
            20                  25                  30

Pro Pro Gln Gln Gln Gln Gln Pro Pro Gln Gln Pro Thr Pro Pro
                35                  40                  45

Lys Leu Ala Gln Ala Thr Ser Ser Ser Ser Thr Ser Ala Ala Ala
    50                  55                  60

Ala Ser Ser Ser Ser Ser Thr Ser Thr Ser Met Ala Val Ala Val
65                  70                  75                  80

Ala Ser Gly Ser Ala Pro Pro Gly Gly Pro Gly Pro Gly Arg Thr Pro
                85                  90                  95

Ala Pro Val Gln Met Asn Leu Tyr Ala Thr Trp Glu Val Asp Arg Ser
            100                 105                 110

Ser Ser Ser Cys Val Pro Arg Leu Phe Ser Leu Thr Leu Lys Lys Leu
            115                 120                 125

Val Met Leu Lys Glu Met Asp Lys Asp Leu Asn Ser Val Ile Ala
    130                 135                 140

Val Lys Leu Gln Gly Ser Lys Arg Ile Leu Arg Ser Asn Glu Ile Val
145                 150                 155                 160

Leu Pro Ala Ser Gly Leu Val Glu Thr Glu Leu Gln Leu Thr Phe Ser
                165                 170                 175

Leu Gln Tyr Pro His Phe Leu Lys Arg Asp Ala Asn Lys Leu Gln Ile
            180                 185                 190

Met Leu Gln Arg Arg Lys Arg Tyr Lys Asn Arg Thr Ile Leu Gly Tyr
            195                 200                 205

Lys Thr Leu Ala Val Gly Leu Ile Asn Met Ala Glu Val Met Gln His
210                 215                 220

Pro Asn Glu Gly Ala Leu Val Leu Gly Leu His Ser Asn Val Lys Asp
225                 230                 235                 240

Val Ser Val Pro Val Ala Glu Ile Lys Ile Tyr Ser Leu Ser Ser Gln
                245                 250                 255

Pro Ile Asp His Glu Gly Ile Lys Ser Lys Leu Ser Asp Arg Ser Pro
            260                 265                 270

Asp Ile Asp Asn Tyr Ser Glu Glu Glu Glu Ser Phe Ser Ser Glu
            275                 280                 285

Gln Glu Gly Ser Asp Asp Pro Leu His Gly Gln Asp Leu Phe Tyr Glu
            290                 295                 300

Asp Glu Asp Leu Arg Lys Val Lys Lys Thr Arg Arg Lys Leu Thr Ser
305                 310                 315                 320

Thr Ser Ala Ile Thr Arg Gln Pro Asn Ile Lys Gln Lys Phe Val Ala
                325                 330                 335

Leu Leu Lys Arg Phe Lys Val Ser Asp Glu Val Gly Phe Gly Leu Glu
            340                 345                 350

His Val Ser Arg Glu Gln Ile Arg Glu Val Glu Glu Asp Leu Asp Glu
            355                 360                 365

Leu Tyr Asp Ser Leu Glu Met Tyr Asn Pro Ser Asp Ser Gly Pro Glu
    370                 375                 380

Met Glu Glu Thr Glu Ser Ile Leu Ser Thr Pro Lys Pro Lys Leu Lys
385                 390                 395                 400

Pro Phe Phe Glu Gly Met Ser Gln Ser Ser Ser Gln Thr Glu Ile Gly
                405                 410                 415

```
Ser Leu Asn Ser Lys Gly Ser Leu Gly Lys Asp Thr Ser Pro Met
            420                 425                 430

Glu Leu Ala Ala Leu Glu Lys Ile Lys Ser Thr Trp Ile Lys Asn Gln
            435                 440                 445

Asp Asp Ser Leu Thr Glu Thr Asp Thr Leu Glu Ile Thr Asp Gln Asp
            450                 455                 460

Met Phe Gly Asp Ala Ser Thr Ser Leu Val Val Pro Glu Lys Val Lys
465                 470                 475                 480

Thr Pro Met Lys Ser Ser Lys Thr Asp Leu Gln Gly Ser Ala Ser Pro
                485                 490                 495

Ser Lys Val Glu Gly Val His Thr Pro Arg Gln Lys Arg Ser Thr Pro
            500                 505                 510

Leu Lys Glu Arg Gln Leu Ser Lys Pro Leu Ser Glu Arg Thr Asn Ser
            515                 520                 525

Ser Asp Ser Glu Arg Ser Pro Asp Leu Gly His Ser Thr Gln Ile Pro
            530                 535                 540

Arg Lys Val Val Tyr Asp Gln Leu Asn Gln Ile Leu Val Ser Asp Ala
545                 550                 555                 560

Ala Leu Pro Glu Asn Val Ile Leu Val Asn Thr Thr Asp Trp Gln Gly
                565                 570                 575

Gln Tyr Val Ala Glu Leu Leu Gln Asp Gln Arg Lys Pro Val Val Cys
            580                 585                 590

Thr Cys Ser Thr Val Glu Val Gln Ala Val Leu Ser Ala Leu Leu Thr
            595                 600                 605

Arg Ile Gln Arg Tyr Cys Asn Cys Asn Ser Ser Met Pro Arg Pro Val
610                 615                 620

Lys Val Ala Ala Val Gly Gly Gln Ser Tyr Leu Ser Ser Ile Leu Arg
625                 630                 635                 640

Phe Phe Val Lys Ser Leu Ala Asn Lys Thr Ser Asp Trp Leu Gly Tyr
                645                 650                 655

Met Arg Phe Leu Ile Ile Pro Leu Gly Ser His Pro Val Ala Lys Tyr
            660                 665                 670

Leu Gly Ser Val Asp Ser Lys Tyr Ser Ser Phe Leu Asp Ser Gly
            675                 680                 685

Trp Arg Asp Leu Phe Ser Arg Ser Glu Pro Pro Val Ser Glu Gln Leu
690                 695                 700

Asp Val Ala Gly Arg Val Met Gln Tyr Val Asn Gly Ala Ala Thr Thr
705                 710                 715                 720

His Gln Leu Pro Val Ala Glu Ala Met Leu Thr Cys Arg His Lys Phe
                725                 730                 735

Pro Asp Glu Asp Ser Tyr Gln Lys Phe Ile Pro Phe Ile Gly Val Val
            740                 745                 750

Lys Val Gly Leu Val Glu Asp Ser Pro Ser Thr Ala Gly Asp Gly Asp
            755                 760                 765

Asp Ser Pro Val Val Ser Leu Thr Val Pro Ser Thr Ser Pro Pro Ser
            770                 775                 780

Ser Ser Gly Leu Ser Arg Asp Ala Thr Ala Thr Pro Pro Ser Ser Pro
785                 790                 795                 800

Ser Met Ser Ser Ala Leu Ala Ile Val Gly Ser Pro Asn Ser Pro Tyr
                805                 810                 815

Gly Asp Val Ile Gly Leu Gln Val Asp Tyr Trp Leu Gly His Pro Gly
            820                 825                 830
```

```
Glu Arg Arg Arg Glu Gly Asp Lys Arg Asp Ala Ser Ser Lys Asn Thr
                835                 840                 845

Leu Lys Ser Val Phe Arg Ser Val Gln Val Ser Arg Leu Pro His Ser
    850                 855                 860

Gly Glu Ala Gln Leu Ser Gly Thr Met Ala Met Thr Val Val Thr Lys
865                 870                 875                 880

Glu Lys Asn Lys Lys Val Pro Thr Ile Phe Leu Ser Lys Lys Pro Arg
                885                 890                 895

Glu Lys Glu Val Asp Ser Lys Ser Gln Val Ile Glu Gly Ile Ser Arg
                900                 905                 910

Leu Ile Cys Ser Ala Lys Gln Gln Thr Met Leu Arg Val Ser Ile
    915                 920                 925

Asp Gly Val Glu Trp Ser Asp Ile Lys Phe Phe Gln Leu Ala Ala Gln
930                 935                 940

Trp Pro Thr His Val Lys His Phe Pro Val Gly Leu Phe Ser Gly Ser
945                 950                 955                 960

Lys Ala Thr

<210> SEQ ID NO 6
<211> LENGTH: 4571
<212> TYPE: DNA
<213> ORGANISM: Homo sapiens

<400> SEQUENCE: 6
acccgtgtcg gcctcgcgag ccgcaacagg cagcggcggt cgagcgcgag gcccgcgcgc      60
ccagaggccc cgcgcgtgcg tgcagctcgc tggctgctcg cgctcgggca ggcgggctga     120
ggaggctgcc gcgccccgc cgccgccgcc gcggggaag cctgggagcc agatcggcgt       180
cgcctcggcc tccgtaaccc ccgcctagcc gggccatggc ggaacgcgga ggggcgggcg     240
gtggtcccgg aggcgccggg ggcggcagcg gccagcgggg atccggggtc gcccagtccc     300
ctcagcagcc gccgccgcag cagcagcagc agcagccgcc gcagcagccg acgcccccca     360
agctggccca ggccaccctcg tcgtcctcgt ccacctcggc ggcggctgcc tcctcctcgt     420
cctcgtctac ctccacctcc atggccgtgg cggtggcctc gggctccgcg cctcccggtg     480
gcccggggcc aggccgcacc cccgccccgg tgcagatgaa cctgtacgcc acctgggagg     540
tggaccggag ctcgtccagc tgcgtgccta ggctattcag cttgaccctg aagaaactcg     600
tcatgctaaa agaaatggac aaagatctta actcagtggt catcgctgtg aagctgcagg     660
gttcaaaaag aattcttcgc tccaacgaga tcgtccttcc agctagtgga ctggtggaaa     720
cagagctcca attaaccttc tcccttcagt accctcattt ccttaagcga gatgccaaca     780
agctgcagat catgctgcaa aggagaaaac gttacaagaa tcggaccatc ttgggctata     840
agaccttggc cgtgggactc atcaacatgg cagaggtgat gcagcatcct aatgaaggcg     900
cactggtgct tggcctacac agcaacgtga aggatgtctc tgtgcctgtg cagaaataa     960 agatctactc cctgtccagc caacccattg accatgaagg aatcaaatcc aagctttctg    1020
atcgttctcc tgatattgac aattattctg aggaagagga agagagtttc tcatcagaac    1080
aggaaggcag tgatgatcca ttgcatgggc aggacttgtt ctacgaagac gaagatctcc    1140
ggaaagtgaa gaagacccgg aggaaactaa cctcaacctc tgccatcaca aggcaaccta    1200
acatcaaaca gaagtttgtg gccctcctga gcggttttaa agtttcagat gaggtgggct    1260
ttgggctgga gcatgtgtcc cgcgagcaga tccgggaagt ggaagaggac ttggatgaat    1320
tgtatgacag tctggagatg tacaacccca gcgacagtgg ccctgagatg gaggagacag    1380
```

```
aaagcatcct cagcacgcca aagcccaagc tcaagccttt ctttgagggg atgtcgcagt    1440
ccagctccca gacggagatt ggcagcctca acagcaaagg cagcctcgga aaagacacca    1500
ccagccctat ggaattggct gctctagaaa aaattaaatc tacttggatt aaaaaccaag    1560
atgacagctt gactgaaaca gacactctgg aaatcactga ccaggacatg tttggagatg    1620
ccagcacgag tctggttgtg ccggagaaag tcaaaactcc catgaagtcc agtaaaacgg    1680
atctccaggg ctctgcctcc cccagcaaag tggaggggt gcacacaccc cggcagaaga    1740
ggagcacgcc cctgaaggag cggcagctct ccaagcccct aagtgagagg accaacagtt    1800
ccgacagcga gcgctcccca gatctgggcc acagcacgca gattccaaga aaggtggtgt    1860
atgaccagct caatcagatc ctggtgtcag atgcagccct cccagaaaat gtcattctgg    1920
tgaacaccac tgactggcag ggccagtatg tggctgagct gctccaggac cagcggaagc    1980
ctgtggtgtg cacctgctcc accgtggagg tccaggccgt gctgtccgcc ctgctcaccc    2040
ggatccagcg ctactgcaac tgcaactctt ccatgccgag gccagtgaag gtggctgctg    2100
tgggaggcca gagctacctg agctccatcc tcaggttctt tgtcaagtcc ctggccaaca    2160
agacctccga ctggcttggc tacatgcgct tcctcatcat cccctcggt tctcaccctg    2220 tggccaaata cttggggtca gtcgacagta aatacagtag ttccttcctg gattctggtt    2280
ggagagatct gttcagtcgc tcggagccac cagtgtcaga gcaactggac gtggcagggc    2340
gggtgatgca gtacgtcaac ggggcagcca cgacacacca gcttcccgtg ccgaagcca    2400 tgctgacttg ccggcataag ttccctgatg aagactccta tcagaagttt attcccttca    2460
ttggcgtggt gaaggtgggt ctggttgaag actctccctc cacagcaggc gatggggacg    2520
attctcctgt ggtcagcctt actgtgccct ccacatcacc ccctccagc tcgggcctga    2580 gccgagacgc cacggccacc cctccctcct ccccatctat gagcagcgcc ctggccatcg    2640
tggggagccc taatagccca tatggggacg tgattggcct ccaggtggac tactggctgg    2700
gccaccccgg ggagcggagg agggaaggcg acaagaggga cgccagctcg aagaacaccc    2760
tcaagagtgt cttccgctca gtgcaggtgt cccgcctgcc catagtggg gaggcccagc    2820 tttctggcac catggccatg actgtggtca ccaaagaaaa gaacaagaaa gttcccacca    2880
tcttcctgag caagaaaccc cgagaaaagg aggtggattc taagagccag gtcattgaag    2940
gcatcagccg cctcatctgc tcagccaagc agcagcagac tatgctgaga gtgtccatcg    3000
atggggtcga gtggagtgac atcaagttct tccagctggc agcccagtgg cccacccatg    3060
tcaagcactt tccagtggga ctcttcagtg cagcaaggc cacctgaggc cctgtctccc    3120
agccactttc cctcctggca ctgccaccag cctcaccgcc tgcgggcagg gggaggccag    3180
caggcccggg cccagcaccc cttccctggc accaggtct gcctctcact cgcccaggtc    3240
ccgaaggaca ctgccacagg gacgccttcc ctcccctccc ctccagccca ccctgcaca    3300 gccccctcct cttcccgctt ttccccttct ccttcctgct ccaggcccaa ggcgtgttgg    3360
ttttgccttc tggtgcccat agtcccctgg actgagtccc ccaggccttc cttcacccga    3420
cttccaaact cttccttgtg gtatcagttt ccttctcgga aatgagaaag ctggaatcct    3480
ggtccccagc aggagagcct agtcctcccc cagcccctcc agccaccagg gtgtcctcta    3540
ggatgcagct gccagatcca ctcactctgc tgcctccagc aggacccaag gccactttca    3600
actcttatgg ggttctccac ctgccccaga gcttctcaag ggagggtaag ggggcaccct    3660
gagcccacag gaccccatct tcacagctca caggggcagg aggcagctcc cctgcctcca    3720
```

```
ggaccctgtt gctatggtga cacagcgttt ctaggacaga ggggcctccc agtctccccc    3780
caccacccgt gcacgacttc ctcaccaccc ccaggttccc tgcagatgtc gtgtgtgtcc    3840
tgagtgtttc tttggttctt tgcacgccaa gtctcttggt tgtaccatgt gacacaccct    3900
gtgcactggt cgctgtcttc gtggcttcca cccttgttaa tgatgctcct gcctctgcct    3960
cccagcccct cacccagcac agctctgcct ggacttggag agatgggagg cagaccccca    4020
ccaccataca tgctgtctgt ggcccctcag acattctgtt tcatctccca ttcatctccc    4080
tcctcccacc gtgtcagttt ttctgccttt ccctgctctg ttcttccccc tccttaggcc    4140
ccagcctggg cccagaccca tcctcccagc caggtttccc tccagcaggc tccttccctc    4200
cctgtcacct ccctctcacc aacccggggt ctgagcccct cattcctgac cgtccgtgtt    4260
ctcaggagtg gttgaggaca cagggcccca gcccagccct ctgcaccccc agcccggcc     4320 atctgcgccc cacagcccct ttggagcttt tctcttgtcc tctcactcct tcccagaagt    4380
ttttgcacag aacttcattt tgaaagtgtt tttctcattc tccataccte ccccaagctc    4440 tcctccagcc cttcccaggg ctcagccctg ctgtcctgag cgtctcctgg gccagagaga    4500
ggagatgggg gtgggaggga ctgagttgat gttgggtttt tcattcaata aattggtgat    4560
ttcttaccga c                                                         4571
```

<210> SEQ ID NO 7
<211> LENGTH: 889
<212> TYPE: PRT
<213> ORGANISM: Homo sapiens

<400> SEQUENCE: 7

```
Met Ala Glu Arg Gly Arg Leu Gly Leu Pro Gly Ala Pro Gly Ala Leu
1               5                   10                  15

Asn Thr Pro Val Pro Met Asn Leu Phe Ala Thr Trp Glu Val Asp Gly
            20                  25                  30

Ser Ser Pro Ser Cys Val Pro Arg Leu Cys Ser Leu Thr Leu Lys Lys
        35                  40                  45

Leu Val Val Phe Lys Glu Leu Glu Lys Glu Leu Ile Ser Val Val Ile
    50                  55                  60

Ala Val Lys Met Gln Gly Ser Lys Arg Ile Leu Arg Ser His Glu Ile
65                  70                  75                  80

Val Leu Pro Pro Ser Gly Gln Val Glu Thr Asp Leu Ala Leu Thr Phe
                85                  90                  95

Ser Leu Gln Tyr Pro His Phe Leu Lys Arg Glu Gly Asn Lys Leu Gln
            100                 105                 110

Ile Met Leu Gln Arg Arg Lys Arg Tyr Lys Asn Arg Thr Ile Leu Gly
        115                 120                 125

Tyr Lys Thr Leu Ala Ala Gly Ser Ile Ser Met Ala Glu Val Met Gln
    130                 135                 140

His Pro Ser Glu Gly Gly Gln Val Leu Ser Leu Cys Ser Ser Ile Lys
145                 150                 155                 160

Glu Ala Pro Val Lys Ala Ala Glu Ile Trp Ile Ala Ser Leu Ser Ser
                165                 170                 175

Gln Pro Ile Asp His Glu Asp Ser Thr Met Gln Ala Gly Pro Lys Ala
            180                 185                 190

Lys Ser Thr Asp Asn Tyr Ser Glu Glu Tyr Glu Ser Phe Ser Ser
        195                 200                 205

Glu Gln Glu Ala Ser Asp Asp Ala Val Gln Gly Gln Asp Leu Asp Glu
    210                 215                 220
```

```
Asp Asp Phe Asp Val Gly Lys Pro Lys Gln Arg Arg Ser Ile Val
225                 230                 235                 240

Arg Thr Thr Ser Met Thr Arg Gln Gln Asn Phe Lys Gln Lys Val Val
                245                 250                 255

Ala Leu Leu Arg Arg Phe Lys Val Ser Asp Glu Val Leu Asp Ser Glu
            260                 265                 270

Gln Asp Pro Ala Glu His Ile Pro Glu Ala Glu Glu Asp Leu Asp Leu
        275                 280                 285

Leu Tyr Asp Thr Leu Asp Met Glu His Pro Ser Asp Ser Gly Pro Asp
    290                 295                 300

Met Glu Asp Asp Asp Ser Val Leu Ser Thr Pro Lys Pro Lys Leu Arg
305                 310                 315                 320

Pro Tyr Phe Glu Gly Leu Ser His Ser Ser Gln Thr Glu Ile Gly
                325                 330                 335

Ser Ile His Ser Ala Arg Ser His Lys Glu Pro Pro Ser Pro Ala Asp
            340                 345                 350

Val Pro Glu Lys Thr Arg Ser Leu Gly Gly Arg Gln Pro Ser Asp Ser
        355                 360                 365

Val Ser Asp Thr Val Ala Leu Gly Val Pro Gly Pro Arg Glu His Pro
370                 375                 380

Gly Gln Pro Glu Asp Ser Pro Glu Ala Glu Ala Ser Thr Leu Asp Val
385                 390                 395                 400

Phe Thr Glu Arg Leu Pro Pro Ser Gly Arg Ile Thr Lys Thr Glu Ser
                405                 410                 415

Leu Val Ile Pro Ser Thr Arg Ser Glu Gly Lys Gln Ala Gly Arg Arg
            420                 425                 430

Gly Arg Ser Thr Ser Leu Lys Glu Arg Gln Ala Ala Arg Pro Gln Asn
        435                 440                 445

Glu Arg Ala Asn Ser Leu Asp Asn Glu Arg Cys Pro Asp Ala Arg Ser
    450                 455                 460

Gln Leu Gln Ile Pro Arg Lys Thr Val Tyr Asp Gln Leu Asn His Ile
465                 470                 475                 480

Leu Ile Ser Asp Asp Gln Leu Pro Glu Asn Ile Ile Leu Val Asn Thr
                485                 490                 495

Ser Asp Trp Gln Gly Gln Phe Leu Ser Asp Val Leu Gln Arg His Thr
            500                 505                 510

Leu Pro Val Val Cys Thr Cys Ser Pro Ala Asp Val Gln Ala Ala Phe
        515                 520                 525

Ser Thr Ile Val Ser Arg Ile Gln Arg Tyr Cys Asn Cys Asn Ser Gln
    530                 535                 540

Pro Pro Thr Pro Val Lys Ile Ala Val Ala Gly Ala Gln His Tyr Leu
545                 550                 555                 560

Ser Ala Ile Leu Arg Leu Phe Val Glu Gln Leu Ser His Lys Thr Pro
                565                 570                 575

Asp Trp Leu Gly Tyr Met Arg Phe Leu Val Ile Pro Leu Gly Ser His
            580                 585                 590

Pro Val Ala Arg Tyr Leu Gly Ser Val Asp Tyr Arg Tyr Asn Asn Phe
        595                 600                 605

Phe Gln Asp Leu Ala Trp Arg Asp Leu Phe Asn Lys Leu Glu Ala Gln
    610                 615                 620

Ser Ala Val Gln Asp Thr Pro Asp Ile Val Ser Arg Ile Thr Gln Tyr
625                 630                 635                 640
```

Ile Ala Gly Ala Asn Cys Ala His Gln Leu Pro Ile Ala Glu Ala Met
            645                 650                 655

Leu Thr Tyr Lys Gln Lys Ser Pro Asp Glu Glu Ser Ser Gln Lys Phe
        660                 665                 670

Ile Pro Phe Val Gly Val Val Lys Val Gly Ile Val Glu Pro Ser Ser
    675                 680                 685

Ala Thr Ser Gly Asp Ser Asp Asp Ala Ala Pro Ser Gly Ser Gly Thr
690                 695                 700

Leu Ser Ser Thr Pro Pro Ser Ala Ser Pro Ala Ala Lys Glu Ala Ser
705                 710                 715                 720

Pro Thr Pro Pro Ser Ser Pro Ser Val Ser Gly Gly Leu Ser Ser Pro
                725                 730                 735

Ser Gln Gly Val Gly Ala Glu Leu Met Gly Leu Gln Val Asp Tyr Trp
            740                 745                 750

Thr Ala Ala Gln Pro Ala Asp Arg Lys Arg Asp Ala Glu Lys Lys Asp
        755                 760                 765

Leu Pro Val Thr Lys Asn Thr Leu Lys Cys Thr Phe Arg Ser Leu Gln
    770                 775                 780

Val Ser Arg Leu Pro Ser Ser Gly Glu Ala Ala Thr Pro Thr Met
785                 790                 795                 800

Ser Met Thr Val Val Thr Lys Glu Lys Asn Lys Lys Val Met Phe Leu
                805                 810                 815

Pro Lys Lys Ala Lys Asp Lys Asp Val Glu Ser Lys Ser Gln Cys Ile
            820                 825                 830

Glu Gly Ile Ser Arg Leu Ile Cys Thr Ala Arg Gln Gln Gln Asn Met
        835                 840                 845

Leu Arg Val Leu Ile Asp Gly Val Glu Cys Ser Asp Val Lys Phe Phe
    850                 855                 860

Gln Leu Ala Ala Gln Trp Ser Ser His Val Lys His Phe Pro Ile Cys
865                 870                 875                 880

Ile Phe Gly His Ser Lys Ala Thr Phe
                885

<210> SEQ ID NO 8
<211> LENGTH: 6361
<212> TYPE: DNA
<213> ORGANISM: Homo sapiens

<400> SEQUENCE: 8

```
gcagctcgtc gccgcccgcg ggcctgtccg acgccggggc ccggcccgtc ccctccgccg      60
cccggcagcc atgtgaccgc gccgccgccc tccgcgcgcc cggcccgccc gccgcgcgtc     120
cgcggcccgg ccgcagcccc aggccgccga gggagcggcg gggccggcgc catggccgag     180
cgaggccgcc tcggcctccc cggcgcgccc ggcgcgctca acacgcccgt gcccatgaac     240
ctgttcgcca cctgggaggt ggacggctcc agcccagct gcgtgcccag gttgtgcagc     300
ctgactctga gaagctggt ggtcttcaag gagctggaga aggagctgat ctccgtggtg     360
atcgctgtca agatgcaggg ctccaaacga atcctgcggt cccatgagat tgtgctgccc     420
cccagtggac aagtggagac agacctggcc ctgaccttct ccttgcagta tcctcacttc     480
ttgaagaggg aaggcaacaa gcttcagatc atgctgcagc cagaaagcg ctacaagaac     540
agaaccatcc tgggctacaa gacgctggcc gcgggctcca tcagcatggc tgaggtgatg     600
caacacccgt ctgaaggtgg ccaggtgctg agcctctgca gcagcatcaa ggaggccccc     660
gtcaaggcgg ccgagatctg gatcgcctcc ctgtccagcc agcccattga ccacgaagac     720
```

```
agcaccatgc aggccggccc caaggccaag tccacggata actactccga ggaggagtat    780
gagagcttct cctccgagca ggaggccagt gacgacgccg tgcaggggca ggacttggac    840
gaggacgact ttgacgtggg gaagccgaag aagcagcgga gatcgattgt aagaacgacg    900
tccatgacca ggcaacagaa cttcaagcag aaagtggtag cgctgctgcg gaggttcaaa    960
gtgtccgacg aggtcctgga ctcggagcag gaccctgcgg agcacatccc cgaggcagag   1020
gaggacctgg acctcctgta tgacaccctg gacatggagc ccccagcga cagcggcccc   1080
gacatggagg atgacgacag cgtcctcagc accccaagc cgaagctgcg gccatacttt   1140
gaaggcctgt cgcactcgag ctcgcagacg gagattggga gcatccacag cgcccgcagc   1200
cacaaggagc ccccaagccc ggctgacgtg cccgagaaga cgcggtccct gggaggcagg   1260
cagccgagcg acagtgtctc tgacacggtg gccctcggtg tgccaggccc gagggagcac   1320
cctggacagc ctgaggacag ccccgaggct gaggcctcca ccctggatgt gttcacggag   1380
aggctgccgc ccagcgggag gatcaccaag acagagtccc ttgtcatccc ctccaccagg   1440
tccgagggga agcaggctgg ccgacggggc cggagcacat ccttgaagga gcggcaggca   1500
gcacggcccc agaatgagcg ggccaacagc ctggacaacg agcgctgccc ggacgcccgg   1560
agccagctac aggtgcagct gcagatcccc aggaagactg tgtatgacca gctcaaccac   1620
atcctcatct ccgatgacca gcttcccgaa aacatcatcc ttgtcaacac ctcggactgg   1680
caggggcagt tcctctccga cgtcctgcag aggcacacgc tccccgtggt gtgcacgtgc   1740
tctcctgcgg acgtccaggc ggccttcagc accatcgtct cacgataca gagatactgc   1800
aactgcaatt cccagccccc gaccccgtg aagatcgccg tggcgggagc gcagcattac   1860
ctcagtgcca tcctgcggct ctttgtggag cagctgtccc acaagacacc cgactggctc   1920
ggctacatgc gcttcctggt catcccactg gctcccacc ccgtggccag gtacctaggc   1980
tccgtggact accgctacaa caacttcttc caggacctgg cctggagaga cctgttcaac   2040
aagctggagg cccagagtgc ggtacaggac acgccagaca ttgtgtcacg catcacgcag   2100
tacatcgcag gggccaactg tgcccaccag ctccccatcg cagaggccat gctgacctac   2160
aagcagaaga ggaaaaagca ttttcatttt gactttaccc taagccctga cgaagagtcc   2220
tcccaaaagt tcattccctt tgtcggggtt gtgaaggttg aattgtgga gccatcctcg   2280
gccacatcag gcgactcgga cgacgcggcc ccctcgggct ctggcacgct ctcctccacc   2340
ccgccgtccg catctcctgc ggccaaggag gcctcaccca cccgccctc ctccccgtcg   2400
gtgagcggag gcctgtcctc ccccagccag ggtgtcggcg ccgagctgat ggggctgcag   2460
gtggactact ggacggcagc acagcctgcg gacaggaaga gggacgccga aagaaggac   2520
ctgcctgtca ccaaaaacac gctcaagtgc actttccggt ccctccaggt cagcaggctg   2580
cccagcagcg gcgaggctgc agccacgccc accatgtcca tgaccgtggt caccaaggag   2640
aagaacaaga aggtgatgtt tctgcccaag aaagcgaagg acaaggacgt ggagtctaag   2700
agccagtgca ttgagggcat cagccggctc atctgcactg ccaggcagca gcagaacatg   2760
ctgcgggtcc tcatcgacgg cgtggagtgc agcgacgtca agttcttcca gctggccgcg   2820
cagtggtcct cgcacgtgaa gcacttcccc atctgcatct tcggacactc caaggccacc   2880
ttctagcccc acccaccagg gggcccacct cctgccccat gctgtgaggg gcccagctgc   2940
atttctgtta acatttcagt ttactacaga gacagacgct taaaacacaa agagaaacag   3000
tcttaagtat gaatgtgctc acaacgtgga aactaacggg ggagctcctg ccaggagccg   3060
```

```
aataactgct ctgcttatta acccgaacgt tcggcccggg gctgggaagc cagaaggacg    3120
atgctgagcc atggatcgcg gaaggcgtcc tctggcctca ggagccaccc agagcctcac    3180
aggctgagtt cttgcctctg tgtcctgtcc ttcctggaag tcaggactct gcttcctcag    3240
ggagcccggg gaaggcggag ctcagtggcc acaggccgag ggccatgggg ccgctcagtc    3300
ccgttggggt tgtcctgagt tgagcctggg ggggccgtcc tgcccgccta agagatgccc    3360
ccagcaccgc acactcgtgg ttcccaataa actcctgcct cgcggcggag ttttatagca    3420
gcagatattt ttaatgcttt tcaatacatg ttctaatgta gctgccaaac atgttgctct    3480
tctgaagtcc ccctgggct gggcagagcc agcagagcct gccccacttt ccccagcccc     3540
tgccccaccc cgcctcacac cttccccact ctcaggctgt tcttgaaaca ccatgaggct    3600
tctgcgtgta gtccctgccc caaacttagc aagcacaggg gcctccacag cccaggtggc    3660
cccagaaaat gttccagagc ccagcttggt acatagtgag atgctgctgg ggttggcctg    3720
aggtgggggc cacttcctcc accccagtgg gtatgtctga ggtcagccat ggggatatct    3780
gggttgagat tcaggttttg gtgaatatgg ggcaggcgtc cagatgtgtt tgtgtcacct    3840
gctgcaacgc tgtagccaat gaagattcca gcgggatggc ctgaccagcg gggccggcac    3900
tttggagccg tgggtgcagc caggtacccc gtgcagggcc tgggaggctc tccaggccac    3960
agtcctcaga gcgtgttggg tcccatgttg tgtgtgggtt ccatgccctc cacacagcag    4020
gagagggctt ccctgaccac acctgccccc tcagtcctgc ttctcccag taagcctgca     4080
ctgtggggtc tccataggag gagctgggga agctggggcc ctcccagggg tcctgatcga    4140
ccctgggggc tcttggcctg gtttcgtaag atggagcact gcaaaaggcc atgctcagaa    4200
agcaaacgca gggcagggtg ggcctcgagc cggggctgga ggggtctcca cccttgctgg    4260
cctgagagat ggcccacatt tcttacttgt gaccgccctg ctcttcctgg ccgccccccc    4320
caggtggctg aacagggtga ttttgttgtg gtgaggggcc aggatgtggc ctggtgtgca    4380
gcctcagctc cctgggttca ggcctcagag gtagcctgtg tgcaggaggc agagcccag    4440
cccctcccag ccagagcccc tccacaccag ggactcctcc ttcacctggg accaggagcc    4500
tgggcacac cccagggtgg gggagagggt aggaaggtct cccattgaat cctggcttca    4560
ggctctgccc cgagaagtgt ctgcggtgag ggtgtgagcc ccgggctgat ggcctctgac    4620
cccggcaaca ggtgggaccc tgactgactc gttcagctgc ccccaagctg ggctgcagag    4680
catctgtttt tctgctctcc agtttctttt cttttttttt ttttttttt ttgagatgga    4740
gtcttgctct gttgcccagg ctggagtgca gtggcatgat ctcagctcac tgcagcctcc    4800
gtctcccagg ttcaagcagt tctcctgcct cagcctcccg agtagctggg attacaggcg    4860
tgtgccacca cacctggcta ttttttttgt attttagta gagatggggt tttgccatgt     4920
tggccaggct ggtcttgaac tcctgacctc aagtgatcca cccgcctcgg cctcccaaag    4980
tgctgggatt acaggcgtga gtcaccgcgt cctgcctgct cttcctgttt ctttcccaag    5040
ggtcacactc agtagggaga tgaaggtgga aacatccttg ctgtggcttt ctggcctcag    5100
agcaggtttt agaggaaggg gccacaggct gcctagtgca tcctggctgt gggcagcccc    5160
tttcctggag ccctcctgcc tacccgtac ctcccatctg gctgcacagc tccatcctta     5220
gccacgcaag gggagaacat gggcagagtc tccatccagc agctgggggt tctggtggca    5280
ctccctgtgc ccctgctgct gctggctgt gggtctgccc tgcacccagg agccccacgg     5340
tccatccccc acaccatgcc cagcaccagg gaggttgggg agacaagacc tgggccatgc    5400
cagccctctg tgcctcggtt tcccactgg ttacacagga tggtcgcatt ttccctgcct     5460
```

```
acctcacaga gctgttctga gggtgcatgg aggagcactc tgtcccacca aggacaacta    5520
gaaaccaaag ccatctgaca gccagtgcgg taagggcggg ggatgtgtgt gtgaggtgtg    5580
cacacccccc gagaacctgg ccctggactg gcctcacagg acaggaggca gccccttgta    5640
gagctagggc tcagccccat cagtctcaaa ggttaagcca ccagtcacca ccgaggcacc    5700
cctcaggcct ggtggccact gtccactatt acgtagacag accccaccct cacccaggcc    5760
agctgtgggc cagtcccgcc ctgcaatctg gtctgctgcc ttcctcttcc atgttggtcc    5820
ccttggccac tgtctctggg catgcaagcc agtgtcctgg ttcagtgcct cggccagagc    5880
tggggcagga gaggggcctc tgggtgagag ctggggtgt ctctgcaggg tactggcagc    5940
cttgccacac tgtcctcatt cccagatgga aagacctgag tgcctctcgc cttcctccgg    6000
gaatgaattc ctcatgaaaa tgaccaggcc acttcttccg agggccaggc cgccccctcc    6060
ccgagacctg tcctgccgtc cgcgggtgtg tggcctgtag gggactgaga gctgggcttg    6120
ctgggcacct ctggaatctg accctgtggg ccaaagaagc accactgtag tttctgcaga    6180
cccccatgcg gttcattgtg cattgtttgg tttctaggat gtatgtgttg ctagtttttt    6240
ttaatgaaac cctggattaa tgtaaatagc ttttggga acggattcta atgtcacgta     6300
tgtgaccgtg tggactattt caaggtgctg atgcaacact aataaacctg gaggggccgg    6360
c                                                                   6361
```

<210> SEQ ID NO 9
<211> LENGTH: 25
<212> TYPE: RNA
<213> ORGANISM: Artificial Sequence
<220> FEATURE:
<223> OTHER INFORMATION: HDAC6 siRNA

<400> SEQUENCE: 9
gcugcaccgu gagaguucca acuuu                                         25